US012613237B2

(12) United States Patent
Hughes et al.

(10) Patent No.: US 12,613,237 B2
(45) Date of Patent: Apr. 28, 2026

(54) BIOSENSORS FOR DETECTING ARRESTIN SIGNALING

(71) Applicant: MONTANA MOLECULAR, LLC, Bozeman, MT (US)

(72) Inventors: Thomas Hughes, Bozeman, MT (US); Paul Tewson, Bozeman, MT (US)

(73) Assignee: Montana Molecular, LLC, Bozeman, MT (US)

( * ) Notice: Subject to any disclaimer, the term of this patent is extended or adjusted under 35 U.S.C. 154(b) by 1355 days.

(21) Appl. No.: 17/262,782

(22) PCT Filed: Jul. 30, 2019

(86) PCT No.: PCT/US2019/044165
§ 371 (c)(1),
(2) Date: Jan. 25, 2021

(87) PCT Pub. No.: WO2020/028381
PCT Pub. Date: Feb. 6, 2020

(65) Prior Publication Data
US 2021/0247384 A1     Aug. 12, 2021

Related U.S. Application Data

(60) Provisional application No. 62/712,176, filed on Jul. 30, 2018.

(51) Int. Cl.
| *G01N 33/50* | (2006.01) |
| *C07K 14/47* | (2006.01) |
| *G01N 33/58* | (2006.01) |
| *G01N 33/68* | (2006.01) |

(52) U.S. Cl.
CPC ..... *G01N 33/5041* (2013.01); *C07K 14/4702* (2013.01); *G01N 33/582* (2013.01); *G01N 33/6872* (2013.01); *C07K 2319/60* (2013.01); *G01N 2333/726* (2013.01)

(58) Field of Classification Search
CPC ......... C07K 2319/60; G01N 2333/726; G01N 33/542
See application file for complete search history.

(56) References Cited

U.S. PATENT DOCUMENTS

| | | | |
|---|---|---|---|
| 5,891,646 A | 4/1999 | Barak et al. | |
| 7,138,240 B2 | 11/2006 | Barak et al. | |
| 8,574,865 B2 | 11/2013 | Wright et al. | |
| 9,388,449 B2 | 7/2016 | Wehrman et al. | |
| 9,547,017 B2 | 1/2017 | Hughes et al. | |
| 2006/0078498 A1 | 4/2006 | Buckholz et al. | |
| 2010/0120063 A1 | 5/2010 | Bassoni et al. | |
| 2011/0275134 A1* | 11/2011 | Bouvier | G01N 33/582 |
| | | | 530/402 |
| 2013/0298263 A1 | 11/2013 | Iwawaki et al. | |
| 2013/0344530 A1 | 12/2013 | Oyadomari | |

| | | | |
|---|---|---|---|
| 2015/0037812 A1 | 2/2015 | Schreiter et al. | |
| 2016/0274109 A1 | 9/2016 | Hughes et al. | |
| 2017/0115315 A1 | 4/2017 | Schreiter et al. | |

FOREIGN PATENT DOCUMENTS

| | | |
|---|---|---|
| CN | 101333555 B | 3/2012 |
| CN | 107043783 A | 8/2017 |

OTHER PUBLICATIONS

Clark et al., Chapter 15.5, Ribosomes and Protein Synthesis. Biology 2e (published Mar. 28, 2018), OpenStax, https://openstax.org/books/biology-2e/pages/15-5-ribosomes-and-protein-synthesis [retrieved Nov. 22, 2024] (Year: 2018).*

Smith et al., Biased signalling: from simple switches to allosteric microprocessors. Nature Reviews Drug Discovery (2018), 17: 243-260 (Year: 2018).*

Breton et al., Multiplexing of Multicolor Bioluminescence Resonance Energy Transfer. Biophysical Journal (2010), 99: 4037-4046 (Year: 2010).*

Nasu et al., Structure-and mechanism-guided design of single fluorescent protein-based biosensors. Nature Chemical Biology (2021), 17: 509-518 (Year: 2021).*

Violin et al., G-protein-coupled receptor kinase specificity for B-arrestin recruitment to the B2-adrenergic receptor revealed by fluorescence resonance energy transfer. The Journal of Biological Chemistry (2006), 281: 20577-20588 (Year: 2006).*

Barak et al., "A beta-arrestin/green fluorescent protein biosensor for detecting G protein-coupled receptor activation." J Biol Chem. 1997;272(44):27497-500.

Tanida-Miyake et al., "Optimization of mNeonGreen for *Homo sapiens* increases its fluorescent intensity in mammalian cells." PLoS One. 2018;13(1):e0191108.

Extended European Search Report mailed May 11, 2022 in corresponding European Patent Application No. 19843390.6.

Kenakin, "Biased signalling and allosteric machines: new vistas and challenges for drug discovery." Br J Pharmacol. 2012;165(6):1659-1669.

DeWire et al., "A G protein-biased ligand at the ?-opioid receptor is potently analgesic with reduced gastrointestinal and respiratory dysfunction compared with morphine." J Pharmacol Exp Ther. 2013;344(3):708-17.

Flores-Otero et al., "Ligand-specific endocytic dwell times control functional selectivity of the cannabinoid receptor 1." Nat Commun. 2014;5:4589.

Masri et al., "Antagonism of dopamine D2 receptor/beta-arrestin 2 interaction is a common property of clinically effective antipsychotics." Proc Natl Acad Sci U S A 2008;105(36):13656-61.

(Continued)

*Primary Examiner* — Catherine Konopka
(74) *Attorney, Agent, or Firm* — Dechert LLP

(57)                ABSTRACT

Disclosed herein are nucleic acids comprising fluorescent reporter constructs for detecting changes in the arrestin cellular signaling changes in a cell. Also provided are methods for detecting cellular arrestin signaling changes in cells, as well as vectors and cells comprising nucleic acids comprising reporter constructs for detecting cellular arrestin signaling changes in a cell.

10 Claims, 9 Drawing Sheets

Specification includes a Sequence Listing.

(56) References Cited

OTHER PUBLICATIONS

Scheerer et al., "Structural mechanism of arrestin activation." Curr OpinStruct Biol. 2017:45:160-169.

Shcherbakova et al., "Bright monomeric near-infrared fluorescent proteins as tags and biosensors for multiscale imaging." Nat Commun. 2016;7:12405.

Day et al., "The fluorescent protein palette: tools for cellular imaging." Chem Soc Rev. 2009;38(10):2887-921.

Rodriguez et al., "Construction of Stable Fluorescent Reporter Plasmids for Use in *Staphylococcus aureus*." Front Microbiol. 2017;8:2491.

Bajar et al., "A Guide to Fluorescent Protein FRET Pairs." Sensors. 2016;16(9):1488.

Storace et al., "Toward better genetically encoded sensors of membrane potential." Trends Neurosci. 2016;39 (5):277-289.

Tewson et al., "New DAG and cAMP Sensors Optimized for Live-Cell Assays in Automated Laboratories." J Biomol Screen. 2016:21(3):298-305.

Akerboom et al., "Genetically encoded calcium indicators for multi-color neural activity imaging and combination with optogenetics." Front Mol Neurosci. 2013;6:2.

Zhao et al., "An expanded palette of genetically encoded $Ca^2$? indicators." Science. 2011;333(6051):1888-91.

Nikolaev et al., "Fluorescent sensors for rapid monitoring of intracellular cGMP." Nat Methods. 2006;3(1):23-5.

Okumuto et al., "Detection of glutamate release from neurons by genetically encoded surface-displayed FRET nanosensors." Proc Natl Acad Sci U S A. 2005;102(24):8740-8745.

Bermejo et al., "Dynamic analysis of cytosolic glucose and ATP levels in yeast using optical sensors." Biochem J. 2010;432(2):399-406.

Lager et al., "Conversion of a putative Agrobacterium sugar-binding protein into a FRET sensor with high selectivity for sucrose." J Biol Chem. 2006;281(41):30875-83.

Bilan et al., "Genetically encoded fluorescent indicator for imaging NAD(+)/NADH ratio changes in different cellular compartments." Biochim Biophys Acta. 2014:1840(3):951-7.

Hung et al., "Imaging cytosolic NADH-NAD(+) redox state with a genetically encoded fluorescent biosensor." Cell Metab. 2011:14(4):545-54.

Dittmer et al., "Genetically Encoded Sensors to Elucidate Spatial Distribution of Cellular Zinc." J Biol Chem. 2009;284 (24):16289-97.

Berg et al., "A genetically encoded fluorescent reporter of ATP/ADP ratio." Nat Methods, 2009;6(2):161-6.

Kaper et al., "Nanosensor Detection of an Immunoregulatory Tryptophan Influx/Kynurenine Efflux Cycle." PLoS Biol. 2007;5(1 0):e257.

Lindenburg et al., "MagFRET: The First Genetically Encoded Fluorescent Mg2+Sensor," PLoS One. 2013;8 (12)e82009.

Sprang et al.. "Cell Signaling: Structural Origins of Receptor Bias." Science. 2012;335(6072):1055-6.

Van der Lee et al., "Pharmacological characterization of receptor redistribution and beta-arrestin recruitment assays for the cannabinoid receptor 1," J Biomol Screen. 2009;14(7):811-23.

Szymczak et al., "Correction of multi-gene deficiency in vivo using a single 'self-cleaving' 2A peptide-based retroviral vector." Nat Biotechnol. 2004:22(5):589-94.

Bilan et al., "HyPer-3: a genetically encoded H(2)O(2) probe with improved performance for ratiometric and fluorescence lifetime imaging." ACS Chem Biol. 2013;8(3):535-42.

Oakley et al., "The ligand-independent translocation assay: an enabling technology for screening orphan G protein-coupled receptors by arrestin recruitment." Methods Enzymol. 2006;414:50-63.

International Search Report and Written Opinion relating to International Application No. PCT/US2019/044165 dated Dec. 4, 2019.

Pongo abelii mRNA; cDNA DKFZp468L2113 (from clone DKFZp468L2113), GenBank: CR858205.1 (2008).

* cited by examiner

Arrestin

Linker

Linker for
circular
permutation circularly permuted
mNeonGreen cpmNeonGreen | Linker | Arrestin

| mNeonGreen portion 1 | Linker 1 | Arrestin | Linker 2 | mNeonGreen Portion 2 |
|---|---|---|---|---|

| cpmNeonGreen-Arrestin fusion protein | | | | | | | | |
|---|---|---|---|---|---|---|---|---|
| Construct Name | Plasmid SEQ ID NO | Coding Sequence SEQ ID NO | | cpmNeonGreen SEQ ID NO | | Linker Sequence | | Beta-Arrestin-2 SEQ ID NO |
| -- | Nucleic Acid | Nucleic Acid | Amino Acid | Nucleic Acid | Amino Acid | Nucleic Acid | Amino Acid | Nucleic Acid | Amino Acid |
| BArr 1A | 1 | 2 | 3 | 4 | 5 | GGT / GGC / GGA / GGG | Gly | 6 | 7 |

FIG. 3A

| Arrestin-cpmNeonGreen fusion proteins | | | | | | | | |
|---|---|---|---|---|---|---|---|---|
| Construct Name | Plasmid SEQ ID NO | Construct SEQ ID NO | | Beta-Arrestin-2 SEQ ID NO | | Linker Sequence | | cpmNeonGreen SEQ ID NO |
| -- | Nucleic Acid | Nucleic Acid | Amino Acid | Nucleic Acid | Amino Acid | Nucleic Acid | Amino Acid | Nucleic Acid | Amino Acid |
| BArr 3D | 8 | 9 | 10 | 11 | 12 | ccctcgcat | Pro-Ser-His | 13 | 14 |
| BArr 3F | 15 | 16 | 17 | 18 | 19 | ccctcgcat | Pro-Ser-His | 20 | 21 |

FIG. 3B

| mNeonGreen Part 1-Arrestin-mNeonGreen Part2 | | | |
|---|---|---|---|
| | Plasmid SEQ ID NO | Construct SEQ ID NO | |
| Construct Name | Nucleic Acid | Nucleic Acid | Amino Acid |
| BArr4A | 22 | 23 | 24 |
| BArr5A | 31 | 32 | 33 |
| BArr6B | 40 | 41 | 42 |
| BArr L1-3B8 | 51 | 52 | 53 |

FIG. 3C mNeonGreen Part 1-Arrestin-mNeonGreen Part2

| Construct Name | mNeonGreen Part 1 SEQ ID NO | | 1st Linker Sequence SEQ ID NO | | Beta-Arrestin-2 SEQ ID NO | | 2nd Linker Sequence SEQ ID NO | | mNeonGreen Part 2 SEQ ID NO | |
|---|---|---|---|---|---|---|---|---|---|---|
| | Nucleic Acid | Amino Acid | Nucleic Acid | Amino Acid | Nucleic Acid | Amino Acid | Nucleic Acid | Amino Acid | Nucleic Acid | Amino Acid |
| BArr4A | 25 | 26 | GGT / GGC / GGA / GGG | Gly | 27 | 28 | No linker | No linker | 29 | 30 |
| BArr5A | 34 | 35 | atgcgcggaggg | Met-Arg-Gly | 36 | 37 | aatgtt | Asn-Val | 38 | 39 |
| BArr6B | 43 | 44 | 45 | 46 | 47 | 48 | aatgtt | Asn-Val | 49 | 50 |
| BArr L1-3B8 | 54 | 55 | 56 | 57 | 58 | 59 | aatgtt | Asn-Val | 60 | 61 |

FIG. 3D

SEQUENCE LISTING

```
<160> NUMBER OF SEQ ID NOS: 61

<210> SEQ ID NO 1
<211> LENGTH: 7100
<212> TYPE: DNA
<213> ORGANISM: Artificial Sequence
<220> FEATURE:
<223> OTHER INFORMATION: BArr 1A plasmid
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1936)..(2664)
<223> OTHER INFORMATION: cpmNeonGreen
<220> FEATURE:
<221> NAME/KEY: misc_feature
<222> LOCATION: (2665)..(2667)
<223> OTHER INFORMATION: linker
<220> FEATURE:
<221> NAME/KEY: misc_feature
<222> LOCATION: (2665)..(3888)
<223> OTHER INFORMATION: B-arrestin
<220> FEATURE:
<221> NAME/KEY: misc_feature
<222> LOCATION: (2665)..(3888)
<223> OTHER INFORMATION: bGH poly(A)signal
<220> FEATURE:
<221> NAME/KEY: misc_feature
<222> LOCATION: (4849)..(5437)
<223> OTHER INFORMATION: ori
<220> FEATURE:
<221> NAME/KEY: misc_feature
<222> LOCATION: (5980)..(6795)
<223> OTHER INFORMATION: KanR

<400> SEQUENCE: 1
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg ggtgaaatac cgcacagatg cgtaaggaga aaataccgca tcagattggc      240
tattggccat tgcatacgtt gtatccatat cataatatgt acatttatat tggctcatgt      300
ccaacattac cgccatgttg acattgatta ttgactagtt attaatagta atcaattacg      360
gggtcattag ttcatagccc atatatggag ttccgcgtta cataacttac ggtaaatggc      420
ccgcctggct gaccgcccaa cgaccccgc ccattgacgt caataatgac gtatgttccc      480
atagtaacgc caatagggac tttccattga cgtcaatggg tggagtattt acggtaaact      540
gcccacttgg cagtacatca agtgtatcat atgccaagta cgccccctat tgacgtcaat      600
gacggtaaat ggcccgcctg gcattatgcc cagtacatga ccttatggga ctttcctact      660
tggcagtaca tctacgtatt agtcatcgct attaccatgg tgatgcggtt ttggcagtac      720
atcaatgggc gtggatagcg gtttgactca cggggatttc caagtctcca ccccattgac      780
gtcaatggga gtttgttttg gcaccaaaat caacgggact ttccaaaatg tcgtaacaac      840
```

-continued

```
tccgccccat tgacgcaaat gggcggtagg cgtgtacggt gggaggtcta tataagcaga    900
gctcgtttag tgaaccgtca gatcgcctgg agacgccatc cacgctgttt tgacctccat    960
agaagacacc gggaccgatc cagcctccgc ggccgggaac ggtgcattgg aacgcggatt   1020
ccccgtgcca agagtgacgt aagtaccgcc tatagactct ataggcacac ccctttggct   1080
cttatgcatg ctatactgtt tttggcttgg ggcctataca cccccgcttc cttatgctat   1140
aggtgatggt atagcttagc ctataggtgt gggttattga ccattattga ccactcccct   1200
attggtgacg atactttcca ttactaatcc ataacatggc tctttgccac aactatctct   1260
attggctata tgccaatact ctgtccttca gagactgaca cggactctgt atttttacag   1320
gatggggtcc catttattat ttacaaattc acatatacaa caacgccgtc ccccgtgccc   1380
gcagttttta ttaaacatag cgtgggatct ccacgcgaat ctcgggtacg tgttccggac   1440
atgggctctt ctccggtagc ggcggagctt ccacatccga gccctggtcc catgcctcca   1500
gcggctcatg gtcgctcggc agctccttgc tcctaacagt ggaggccaga cttaggcaca   1560
gcacaatgcc caccaccacc agtgtgccgc acaaggccgt ggcggtaggg tatgtgtctg   1620
aaaatgagcg tggagattgg gctcgcacgg ctgacgcaga tggaagactt aaggcagcgg   1680
cagaagaaga tgcaggcagc tgagttgttg tattctgata agagtcagag gtaactcccg   1740
ttgcggtgct gttaacggtg gagggcagtg tagtctgagc agtactcgtt gctgccgcgc   1800
gcgccaccag acataatagc tgacagacta acagactgtt cctttccatg ggtctttct   1860 gcagtcaccg tcgtcgacac gtgtgatcag atatacgact cactataggg agacccaagc   1920
tggctagcgt ttaccatgtc gaagaagact taccccaacg acaaaaccat catcagtacc   1980
tttaagtgga gttacaccac tggaaatggc aagcgctacc ggagcactgc gcggaccacc   2040
tacacctttg ccaagccaat ggcggctaac tatctgaaga accagccgat gtacgtgttc   2100
cgtaagacgg agctcaagca ctccaagacc gagctcaact tcaaggagtg gcaaaaggcc   2160
tttaccgatg tgatgggcat ggacgagctg tacaagggcg gtaccggagg gagcatggtg   2220
agcaagggcg aggaggataa catggcctct ctcccagcga cacatgagtt acacatcttt   2280
ggctccatca acggtgtgga ctttgacatg gtgggtcagg gcaccggcaa tccaaatgat   2340
ggttatgagg agttaaacct gaagtccacc aagggtgacc tccagttctc ccctggatt    2400 ctggtccctc atatcgggta tggcttccat cagtacctgc cctaccctga cgggatgtcg   2460
cctttccagg ccgccatggt agatggctcc ggataccaag tccatcgcac aatgcagttt   2520
gaagatggtg cctcccttac tgttaactac cgctacacct acgagggaag ccacatcaaa   2580
ggagaggccc aggtgaaggg gactggtttc cctgctgacg tcctgtgat gaccaactcg   2640 ctgaccgctg cggactggtg cagggggag aaacccggga ccagggtctt caagaagtcg   2700
agccctaact gcaagctcac cgtgtacttg ggcaagcggg acttcgtaga tcacctggac   2760
aaagtggacc ctgtagatgg cgtggtgctt gtggaccctg actacctgaa ggaccgcaaa   2820
gtgtttgtga ccctcacctg cgccttccgc tatggccgtg aagacctgga tgtgctgggc   2880
ttgtccttcc gcaaagacct gttcatcgcc acctaccagg ccttccccccc ggtgcccaac   2940 ccaccccggc cccccacccg cctgcaggac cggctgctga ggaagctggg ccagcatgcc   3000 cacccctct tcttcaccat accccagaat cttccatgct ccgtcacact gcagccaggc   3060
ccagaggata caggaaaggc ctgcggcgta gactttgaga ttcgagcctt ctgtgctaaa   3120
tcactagaag agaaaagcca caaaaggaac tctgtgcggc tggtgatccg aaaggtgcag   3180
```

-continued

```
ttcgccccgg agaaacccgg cccccagcct tcagccgaaa ccacacgcca cttcctcatg   3240
tctgaccggt ccctgcacct cgaggcttcc ctggacaagg agctgtacta ccatggggag   3300
cccctcaatg taaatgtcca cgtcaccaac aactccacca agaccgtcaa gaagatcaaa   3360
gtctctgtga gacagtacgc cgacatctgc ctcttcagca ccgcccagta caagtgtcct   3420
gtggctcaac tcgaacaaga tgaccaggta tctcccagct ccacattctg taaggtgtac   3480
accataaccc cactgctcag cgacaaccgg gagaagcggg gtctcgccct ggatgggaaa   3540
ctcaagcacg aggacaccaa cctggcttcc agcaccatcg tgaaggaggg tgccaacaag   3600
gaggtgctgg gaatcctggt gtcctacagg gtcaaggtga agctggtggt gtctcgaggc   3660
ggggatgtct ctgtggagct gccttttgtt cttatgcacc ccaagcccca cgaccacatc   3720
cccctcccca gacccagtc agccgctccg gagacagatg tccctgtgga caccaacctc   3780
attgaatttg ataccaacta tgccacagat gatgacattg tgtttgagga ctttgcccgg   3840
cttcggctga aggggatgaa ggatgacgac tatgatgatc aactctgcta gcgcgccctc   3900
gactgtgcct tctagttgcc agccatcgt atcgcggccg ctctagacca ggcgcctgga   3960
tccagatcac ttctggctaa taaaagatca gagctctaga gatctgtgtg ttggtttttt   4020
gtggatctgc tgtgccttct agttgccagc catctgttgt ttgcccctcc cccgtgcctt   4080
ccttgaccct ggaaggtgcc actcccactg tcctttccta ataaaatgag gaaattgcat   4140
cgcattgtct gagtaggtgt cattctattc tggggggtgg ggtggggcag cacagcaagg   4200
gggaggattg ggaagacaat agcaggcatg ctggggatgc ggtgggctct atgggtacct   4260
ctctctctct ctctctctct ctctctctct ctctctctcg gtacctctct ctctctctct   4320
ctctctctct ctctctctct ctctcggtac caggtgctga agaattgacc cggttcctcc   4380
tgggccagaa agaagcaggc acatcccctt ctctgtgaca cacccgtcc acgcccctgg   4440 ttcttagttc cagccccact cataggacac tcatagctca ggagggctcc gccttcaatc   4500
ccacccgcta aagtacttgg agcggtctct ccctccctca tcagcccacc aaaccaaacc   4560
tagcctccaa gagtgggaag aaattaaagc aagataggct attaagtgca gagggagaga   4620
aaatgcctcc aacatgtgag gaagtaatga gagaaatcat agaatttctt ccgcttcctc   4680
gctcactgac tcgctgcgct cggtcgttcg ctgcggcga gcggtatcag ctcactcaaa   4740
ggcggtaata cggttatcca cagaatcagg ggataacgca ggaaagaaca tgtgagcaaa   4800
aggccagcaa aaggccagga accgtaaaaa ggccgcgttg ctggcgtttt tccataggct   4860
ccgcccccct gacgagcatc acaaaaatcg acgctcaagt cagaggtggc gaaacccgac   4920
aggactataa agataccagg cgtttccccc tggaagctcc ctcgtgcgct ctcctgttcc   4980
gaccctgccg cttaccggat acctgtccgc ctttctccct tcgggaagcg tggcgctttc   5040
tcaatgctca cgctgtaggt atctcagttc ggtgtaggtc gttcgctcca agctgggctg   5100
tgtgcacgaa ccccccgttc agcccgaccg ctgcgcctta ccggtaact atcgtcttga   5160 gtccaacccg gtaagacacg acttatcgcc actggcagca gccactggta acaggattag   5220
cagagcgagg tatgtaggcg gtgctacaga gttcttgaag tggtggccta actacggcta   5280
cactagaagg acagtatttg gtatctgcgc tctgctgaag ccagttacct tcggaaaaag   5340
agttggtagc tcttgatccg gcaaacaaac caccgctggt agcggtggtt tttttgtttg   5400
caagcagcag attacgcgca gaaaaaaagg atctcaagaa gatcctttga tcttttctac   5460
ggggtctgac gctcagtgga acgaaaactc acgttaaggg attttggtca tgagattatc   5520
aaaaaggatc ttcacctaga tccttttaaa ttaaaaatga agttttaaat caatctaaag   5580
```

-continued

```
tatatatgag taaacttggt ctgacagtta ccaatgctta atcagtgagg cacctatctc      5640
agcgatctgt ctatttcgtt catccatagt tgcctgactc cggggggggg gggcgctgag      5700
gtctgcctcg tgaagaaggt gttgctgact cataccaggc ctgaatcgcc ccatcatcca      5760
gccagaaagt gagggagcca cggttgatga gagctttgtt gtaggtggac cagttggtga      5820
ttttgaactt ttgctttgcc acggaacggt ctgcgttgtc gggaagatgc gtgatctgat      5880
ccttcaactc agcaaaagtt cgatttattc aacaaagccg ccgtcccgtc aagtcagcgt      5940
aatgctctgc cagtgttaca accaattaac caattctgat tagaaaaact catcgagcat      6000
caaatgaaac tgcaatttat tcatatcagg attatcaata ccatattttt gaaaaagccg      6060
tttctgtaat gaaggagaaa actcaccgag gcagttccat aggatggcaa gatcctggta      6120
tcggtctgcg attccgactc gtccaacatc aatacaacct attaatttcc cctcgtcaaa      6180
aataaggtta tcaagtgaga atcaccatg agtgacgact gaatccggtg agaatggcaa       6240
aagcttatgc atttctttcc agacttgttc aacaggccag ccattacgct cgtcatcaaa      6300
atcactcgca tcaaccaaac cgttattcat tcgtgattgc gcctgagcga gacgaaatac      6360
gcgatcgctg ttaaaaggac aattacaaac aggaatcgaa tgcaaccggc gcaggaacac      6420
tgccagcgca tcaacaatat tttcacctga atcaggatat tcttctaata cctggaatgc      6480
tgttttcccg gggatcgcag tggtgagtaa ccatgcatca tcaggagtac ggataaaatg      6540
cttgatggtc ggaagaggca taaattccgt cagccagttt agtctgacca tctcatctgt      6600
aacatcattg gcaacgctac ctttgccatg tttcagaaac aactctggcg catcgggctt      6660
cccatacaat cgatagattg tcgcacctga ttgcccgaca ttatcgcgag cccatttata      6720
cccatataaa tcagcatcca tgttggaatt taatcgcggc ctcgagcaag acgtttcccg      6780
ttgaatatgg ctcataacac cccttgtatt actgtttatg taagcagaca gttttattgt      6840
tcatgatgat atattttat cttgtgcaat gtaacatcag agattttgag acacaacgtg       6900
gctttccccc ccccccatt attgaagcat ttatcagggt tattgtctca tgagcggata       6960
catatttgaa tgtatttaga aaaataaaca aataggggtt ccgcgcacat ttccccgaaa      7020
agtgccacct gacgtctaag aaaccattat tatcatgaca ttaacctata aaaataggcg      7080
tatcacgagg ccctttcgtc                                                  7100
```

<210> SEQ ID NO 2
<211> LENGTH: 1953
<212> TYPE: DNA
<213> ORGANISM: Artificial Sequence
<220> FEATURE:
<223> OTHER INFORMATION: BArr 1A coding sequence
<220> FEATURE:
<221> NAME/KEY: misc_feature
<222> LOCATION: (1)..(729)
<223> OTHER INFORMATION: cpmNeonGreen
<220> FEATURE:
<221> NAME/KEY: misc_feature
<222> LOCATION: (730)..(1953)
<223> OTHER INFORMATION: B-arrestin
<220> FEATURE:
<221> NAME/KEY: misc_feature
<222> LOCATION: (730)..(732)
<223> OTHER INFORMATION: linker

<400> SEQUENCE: 2

```
atgtcgaaga agacttaccc caacgacaaa accatcatca gtaccttaa gtggagttac       60 accactggaa atggcaagcg ctaccggagc actgcgcgga ccacctacac ctttgccaag      120
```

```
ccaatggcgg ctaactatct gaagaaccag ccgatgtacg tgttccgtaa gacggagctc        180
aagcactcca agaccgagct caacttcaag gagtggcaaa aggcctttac cgatgtgatg        240
ggcatggacg agctgtacaa gggcggtacc ggagggagca tggtgagcaa gggcgaggag        300
gataacatgg cctctctccc agcgacacat gagttacaca tctttggctc catcaacggt        360
gtggactttg acatggtggg tcagggcacc ggcaatccaa atgatggtta tgaggagtta        420
aacctgaagt ccaccaaggg tgacctccag ttctccccct ggattctggt ccctcatatc        480
gggtatggct ccatcagta cctgccctac cctgacggga tgtcgccttt ccaggccgcc        540
atggtagatg gctccggata ccaagtccat cgcacaatgc agtttgaaga tggtgcctcc        600
cttactgtta actaccgcta cacctacgag ggaagccaca tcaaaggaga ggcccaggtg        660
aaggggactg gtttccctgc tgacggtcct gtgatgacca actcgctgac cgctgcggac        720
tggtgcaggg gggagaaacc cgggaccagg gtcttcaaga agtcgagccc taactgcaag        780
ctcaccgtgt acttgggcaa gcgggacttc gtagatcacc tggacaaagt ggaccctgta        840
gatggcgtgg tgcttgtgga ccctgactac ctgaaggacc gcaaagtgtt tgtgaccctc        900
acctgcgcct ccgctatgg ccgtgaagac ctggatgtgc tgggcttgtc cttccgcaaa        960
gacctgttca tcgccaccta ccaggccttc cccccggtgc ccaacccacc ccggcccccc       1020
acccgcctgc aggaccggct gctgaggaag ctgggccagc atgcccaccc cttcttcttc       1080
accatacccc agaatcttcc atgctccgtc acactgcagc caggcccaga ggatacagga       1140
aaggcctgcg gcgtagactt tgagattcga gccttctgtg ctaaatcact agaagagaaa       1200
agccacaaaa ggaactctgt gcggctggtg atccgaaagg tgcagttcgc cccggagaaa       1260 cccggcccc agccttcagc cgaaaccaca cgccacttcc tcatgtctga ccggtccctg       1320
cacctcgagg cttccctgga caaggagctg tactaccatg gggagcccct caatgtaaat       1380
gtccacgtca ccaacaactc caccaagacc gtcaagaaga tcaaagtctc tgtgagacag       1440
tacgccgaca tctgcctctt cagcaccgcc cagtacaagt gtcctgtggc tcaactcgaa       1500
caagatgacc aggtatctcc cagctccaca ttctgtaagg tgtacaccat aaccccactg       1560
ctcagcgaca accgggagaa gcggggtctc gccctggatg ggaaactcaa gcacgaggac       1620
accaacctgg cttccagcac catcgtgaag gagggtgcca acaaggaggt gctgggaatc       1680
ctggtgtcct acagggtcaa ggtgaagctg gtggtgtctc gaggcgggga tgtctctgtg       1740
gagctgcctt ttgttcttat gcaccccaag ccccacgacc acatccccct ccccagaccc       1800
cagtcagccg ctccggagac agatgtccct gtggacacca acctcattga atttgatacc       1860
aactatgcca cagatgatga cattgtgttt gaggactttg cccggcttcg gctgaagggg       1920
atgaaggatg acgactatga tgatcaactc tgc                                    1953
```

<210> SEQ ID NO 3
<211> LENGTH: 651
<212> TYPE: PRT
<213> ORGANISM: Artificial Sequence
<220> FEATURE:
<223> OTHER INFORMATION: BArr 1A coding sequence
<220> FEATURE:
<221> NAME/KEY: SITE
<222> LOCATION: (1)..(243)
<223> OTHER INFORMATION: cpmNeonGreen
<220> FEATURE:
<221> NAME/KEY: SITE
<222> LOCATION: (244)..(651)
<223> OTHER INFORMATION: B-arrestin
<220> FEATURE:
<221> NAME/KEY: SITE

```
<222> LOCATION: (244)..(244)
<223> OTHER INFORMATION: linker

<400> SEQUENCE: 3

Met Ser Lys Lys Thr Tyr Pro Asn Asp Lys Thr Ile Ile Ser Thr Phe
1               5                   10                  15

Lys Trp Ser Tyr Thr Thr Gly Asn Gly Lys Arg Tyr Arg Ser Thr Ala
                20                  25                  30

Arg Thr Thr Tyr Thr Phe Ala Lys Pro Met Ala Ala Asn Tyr Leu Lys
            35                  40                  45

Asn Gln Pro Met Tyr Val Phe Arg Lys Thr Glu Leu Lys His Ser Lys
        50                  55                  60

Thr Glu Leu Asn Phe Lys Glu Trp Gln Lys Ala Phe Thr Asp Val Met
65                  70                  75                  80

Gly Met Asp Glu Leu Tyr Lys Gly Gly Thr Gly Gly Ser Met Val Ser
                85                  90                  95

Lys Gly Glu Glu Asp Asn Met Ala Ser Leu Pro Ala Thr His Glu Leu
            100                 105                 110

His Ile Phe Gly Ser Ile Asn Gly Val Asp Phe Asp Met Val Gly Gln
        115                 120                 125

Gly Thr Gly Asn Pro Asn Asp Gly Tyr Glu Glu Leu Asn Leu Lys Ser
    130                 135                 140

Thr Lys Gly Asp Leu Gln Phe Ser Pro Trp Ile Leu Val Pro His Ile
145                 150                 155                 160

Gly Tyr Gly Phe His Gln Tyr Leu Pro Tyr Pro Asp Gly Met Ser Pro
                165                 170                 175

Phe Gln Ala Ala Met Val Asp Gly Ser Gly Tyr Gln Val His Arg Thr
            180                 185                 190

Met Gln Phe Glu Asp Gly Ala Ser Leu Thr Val Asn Tyr Arg Tyr Thr
        195                 200                 205

Tyr Glu Gly Ser His Ile Lys Gly Glu Ala Gln Val Lys Gly Thr Gly
    210                 215                 220

Phe Pro Ala Asp Gly Pro Val Met Thr Asn Ser Leu Thr Ala Ala Asp
225                 230                 235                 240

Trp Cys Arg Gly Glu Lys Pro Gly Thr Arg Val Phe Lys Lys Ser Ser
                245                 250                 255

Pro Asn Cys Lys Leu Thr Val Tyr Leu Gly Lys Arg Asp Phe Val Asp
            260                 265                 270

His Leu Asp Lys Val Asp Pro Val Asp Gly Val Val Leu Val Asp Pro
        275                 280                 285

Asp Tyr Leu Lys Asp Arg Lys Val Phe Val Thr Leu Thr Cys Ala Phe
    290                 295                 300

Arg Tyr Gly Arg Glu Asp Leu Asp Val Leu Gly Leu Ser Phe Arg Lys
305                 310                 315                 320

Asp Leu Phe Ile Ala Thr Tyr Gln Ala Phe Pro Pro Val Pro Asn Pro
                325                 330                 335

Pro Arg Pro Pro Thr Arg Leu Gln Asp Arg Leu Leu Arg Lys Leu Gly
            340                 345                 350

Gln His Ala His Pro Phe Phe Phe Thr Ile Pro Gln Asn Leu Pro Cys
        355                 360                 365

Ser Val Thr Leu Gln Pro Gly Pro Glu Asp Thr Gly Lys Ala Cys Gly
    370                 375                 380

Val Asp Phe Glu Ile Arg Ala Phe Cys Ala Lys Ser Leu Glu Glu Lys
385                 390                 395                 400
```

```
Ser His Lys Arg Asn Ser Val Arg Leu Val Ile Arg Lys Val Gln Phe
            405                 410                 415

Ala Pro Glu Lys Pro Gly Pro Gln Pro Ser Ala Glu Thr Thr Arg His
            420                 425                 430

Phe Leu Met Ser Asp Arg Ser Leu His Leu Glu Ala Ser Leu Asp Lys
        435                 440                 445

Glu Leu Tyr Tyr His Gly Glu Pro Leu Asn Val Asn Val His Val Thr
    450                 455                 460

Asn Asn Ser Thr Lys Thr Val Lys Lys Ile Lys Val Ser Val Arg Gln
465                 470                 475                 480

Tyr Ala Asp Ile Cys Leu Phe Ser Thr Ala Gln Tyr Lys Cys Pro Val
                485                 490                 495

Ala Gln Leu Glu Gln Asp Asp Gln Val Ser Pro Ser Ser Thr Phe Cys
            500                 505                 510

Lys Val Tyr Thr Ile Thr Pro Leu Leu Ser Asp Asn Arg Glu Lys Arg
            515                 520                 525

Gly Leu Ala Leu Asp Gly Lys Leu Lys His Glu Asp Thr Asn Leu Ala
    530                 535                 540

Ser Ser Thr Ile Val Lys Glu Gly Ala Asn Lys Glu Val Leu Gly Ile
545                 550                 555                 560

Leu Val Ser Tyr Arg Val Lys Val Lys Leu Val Val Ser Arg Gly Gly
                565                 570                 575

Asp Val Ser Val Glu Leu Pro Phe Val Leu Met His Pro Lys Pro His
            580                 585                 590

Asp His Ile Pro Leu Pro Arg Pro Gln Ser Ala Ala Pro Glu Thr Asp
            595                 600                 605

Val Pro Val Asp Thr Asn Leu Ile Glu Phe Asp Thr Asn Tyr Ala Thr
    610                 615                 620

Asp Asp Asp Ile Val Phe Glu Asp Phe Ala Arg Leu Arg Leu Lys Gly
625                 630                 635                 640

Met Lys Asp Asp Asp Tyr Asp Asp Gln Leu Cys
                645                 650
```

```
<210> SEQ ID NO 4
<211> LENGTH: 729
<212> TYPE: DNA
<213> ORGANISM: Artificial Sequence
<220> FEATURE:
<223> OTHER INFORMATION: BArr 1A -cpmNeonGreen
<220> FEATURE:
<221> NAME/KEY: misc_feature
<222> LOCATION: (1)..(729)
<223> OTHER INFORMATION: cpmNeonGreen

<400> SEQUENCE: 4
atgtcgaaga agacttaccc caacgacaaa accatcatca gtacctttaa gtggagttac      60
accactggaa atggcaagcg ctaccggagc actgcgcgga ccacctacac ctttgccaag     120
ccaatggcgg ctaactatct gaagaaccag ccgatgtacg tgttccgtaa gacggagctc     180
aagcactcca agaccgagct caacttcaag gagtggcaaa aggcctttac cgatgtgatg     240
ggcatggacg agctgtacaa gggcggtacc ggagggagtc tggtgagcaa gggcgaggag     300
gataacatgg cctctctccc agcgacacat gagttacaca tctttggctc catcaacggt     360
gtggactttg acatggtggg tcagggcacc ggcaatccaa atgatggtta tgaggagtta     420
aacctgaagt ccaccaaggg tgacctccag ttctcccccct ggattctggt ccctcatatc     480
```

-continued

```
gggtatggct tccatcagta cctgccctac cctgacggga tgtcgccttt ccaggccgcc      540
atggtagatg ctccggata ccaagtccat cgcacaatgc agtttgaaga tggtgcctcc      600
cttactgtta actaccgcta cacctacgag ggaagccaca tcaaaggaga ggcccaggtg      660
aaggggactg gtttccctgc tgacggtcct gtgatgacca actcgctgac cgctgcggac      720
tggtgcagg                                                              729
```

```
<210> SEQ ID NO 5
<211> LENGTH: 243
<212> TYPE: PRT
<213> ORGANISM: Artificial Sequence
<220> FEATURE:
<223> OTHER INFORMATION: BArr 1A - cpmNeonGreen

<400> SEQUENCE: 5

Met Ser Lys Lys Thr Tyr Pro Asn Asp Lys Thr Ile Ile Ser Thr Phe
1               5                   10                  15

Lys Trp Ser Tyr Thr Thr Gly Asn Gly Lys Arg Tyr Arg Ser Thr Ala
            20                  25                  30

Arg Thr Thr Tyr Thr Phe Ala Lys Pro Met Ala Ala Asn Tyr Leu Lys
        35                  40                  45

Asn Gln Pro Met Tyr Val Phe Arg Lys Thr Glu Leu Lys His Ser Lys
    50                  55                  60

Thr Glu Leu Asn Phe Lys Glu Trp Gln Lys Ala Phe Thr Asp Val Met
65                  70                  75                  80

Gly Met Asp Glu Leu Tyr Lys Gly Gly Thr Gly Gly Ser Met Val Ser
                85                  90                  95

Lys Gly Glu Glu Asp Asn Met Ala Ser Leu Pro Ala Thr His Glu Leu
            100                 105                 110

His Ile Phe Gly Ser Ile Asn Gly Val Asp Phe Asp Met Val Gly Gln
            115                 120                 125

Gly Thr Gly Asn Pro Asn Asp Gly Tyr Glu Glu Leu Asn Leu Lys Ser
        130                 135                 140

Thr Lys Gly Asp Leu Gln Phe Ser Pro Trp Ile Leu Val Pro His Ile
145                 150                 155                 160

Gly Tyr Gly Phe His Gln Tyr Leu Pro Tyr Pro Asp Gly Met Ser Pro
                165                 170                 175

Phe Gln Ala Ala Met Val Asp Gly Ser Gly Tyr Gln Val His Arg Thr
            180                 185                 190

Met Gln Phe Glu Asp Gly Ala Ser Leu Thr Val Asn Tyr Arg Tyr Thr
            195                 200                 205

Tyr Glu Gly Ser His Ile Lys Gly Glu Ala Gln Val Lys Gly Thr Gly
        210                 215                 220

Phe Pro Ala Asp Gly Pro Val Met Thr Asn Ser Leu Thr Ala Ala Asp
225                 230                 235                 240

Trp Cys Arg
```

```
<210> SEQ ID NO 6
<211> LENGTH: 1224
<212> TYPE: DNA
<213> ORGANISM: Artificial Sequence
<220> FEATURE:
<223> OTHER INFORMATION: BArr 1A - Beta-arrestin-2

<400> SEQUENCE: 6
ggggagaaac ccgggaccag ggtcttcaag aagtcgagcc ctaactgcaa gctcaccgtg      60
```

-continued

| | |
|---|---|
| tacttgggca agcgggactt cgtagatcac ctggacaaag tggaccctgt agatggcgtg | 120 |
| gtgcttgtgg accctgacta cctgaaggac cgcaaagtgt ttgtgaccct cacctgcgcc | 180 |
| ttccgctatg gccgtgaaga cctggatgtg ctgggcttgt ccttccgcaa agacctgttc | 240 |
| atcgccacct accaggcctt cccccggtg cccaacccac ccggcccc cacccgcctg | 300 |
| caggaccggc tgctgaggaa gctgggccag catgcccacc ccttcttctt caccataccc | 360 |
| cagaatcttc catgctccgt cacactgcag ccaggcccag aggatacagg aaaggcctgc | 420 |
| ggcgtagact ttgagattcg agccttctgt gctaaatcac tagaagagaa aagccacaaa | 480 |
| aggaactctg tgcggctggt gatccgaaag gtgcagttcg ccccggagaa acccggcccc | 540 |
| cagccttcag ccgaaaccac acgccacttc ctcatgtctg accggtccct gcacctcgag | 600 |
| gcttccctgg acaaggagct gtactaccat ggggagcccc tcaatgtaaa tgtccacgtc | 660 |
| accaacaact ccaccaagac cgtcaagaag atcaaagtct ctgtgagaca gtacgccgac | 720 |
| atctgcctct tcagcaccgc ccagtacaag tgtcctgtgg ctcaactcga acaagatgac | 780 |
| caggtatctc ccagctccac attctgtaag gtgtacacca taaccccact gctcagcgac | 840 |
| aaccgggaga gcgggggtct cgccctggat gggaaactca gcacgaggta caccaacctg | 900 |
| gcttccagca ccatcgtgaa ggaggtgcc aacaaggagg tgctgggaat cctggtgtcc | 960 |
| tacaggtca aggtgaagct ggtggtgtct cgaggcgggg atgtctctgt ggagctgcct | 1020 |
| tttgttctta tgcaccccaa gcccacgac cacatccccc tccccagacc ccagtcagcc | 1080 |
| gctccggaga cagatgtccc tgtggacacc aacctcattg aatttgatac caactatgcc | 1140 |
| acagatgatg acattgtgtt tgaggactt gcccggcttc ggctgaaggg gatgaaggat | 1200 |
| gacgactatg atgatcaact ctgc | 1224 |

```
<210> SEQ ID NO 7
<211> LENGTH: 408
<212> TYPE: PRT
<213> ORGANISM: Artificial Sequence
<220> FEATURE:
<223> OTHER INFORMATION: BArr 1A - Beta-arrestin-2
<220> FEATURE:
<221> NAME/KEY: SITE
<222> LOCATION: (1)..(408)
<223> OTHER INFORMATION: Beta-arrestin-2

<400> SEQUENCE: 7
```

```
Met Glu Lys Pro Gly Thr Arg Val Phe Lys Lys Ser Ser Pro Asn Cys
1               5                   10                  15

Lys Leu Thr Val Tyr Leu Gly Lys Arg Asp Phe Val Asp His Leu Asp
            20                  25                  30

Lys Val Asp Pro Val Asp Gly Val Val Leu Val Asp Pro Asp Tyr Leu
        35                  40                  45

Lys Asp Arg Lys Val Phe Val Thr Leu Thr Cys Ala Phe Arg Tyr Gly
    50                  55                  60

Arg Glu Asp Leu Asp Val Leu Gly Leu Ser Phe Arg Lys Asp Leu Phe
65                  70                  75                  80

Ile Ala Thr Tyr Gln Ala Phe Pro Pro Val Pro Asn Pro Pro Arg Pro
                85                  90                  95

Pro Thr Arg Leu Gln Asp Arg Leu Leu Arg Lys Leu Gly Gln His Ala
            100                 105                 110

His Pro Phe Phe Phe Thr Ile Pro Gln Asn Leu Pro Cys Ser Val Thr
        115                 120                 125

Leu Gln Pro Gly Pro Glu Asp Thr Gly Lys Ala Cys Gly Val Asp Phe
```

```
        130             135             140

Glu Ile Arg Ala Phe Cys Ala Lys Ser Leu Glu Glu Lys Ser His Lys
145             150             155             160

Arg Asn Ser Val Arg Leu Val Ile Arg Lys Val Gln Phe Ala Pro Glu
                165             170             175

Lys Pro Gly Pro Gln Pro Ser Ala Glu Thr Thr Arg His Phe Leu Met
            180             185             190

Ser Asp Arg Ser Leu His Leu Glu Ala Ser Leu Asp Lys Glu Leu Tyr
            195             200             205

Tyr His Gly Glu Pro Leu Asn Val Asn Val His Val Thr Asn Asn Ser
        210             215             220

Thr Lys Thr Val Lys Lys Ile Lys Val Ser Val Arg Gln Tyr Ala Asp
225             230             235             240

Ile Cys Leu Phe Ser Thr Ala Gln Tyr Lys Cys Pro Val Ala Gln Leu
                245             250             255

Glu Gln Asp Asp Gln Val Ser Pro Ser Ser Thr Phe Cys Lys Val Tyr
            260             265             270

Thr Ile Thr Pro Leu Leu Ser Asp Asn Arg Glu Lys Arg Gly Leu Ala
            275             280             285

Leu Asp Gly Lys Leu Lys His Glu Asp Thr Asn Leu Ala Ser Ser Thr
        290             295             300

Ile Val Lys Glu Gly Ala Asn Lys Glu Val Leu Gly Ile Leu Val Ser
305             310             315             320

Tyr Arg Val Lys Val Lys Leu Val Val Ser Arg Gly Gly Asp Val Ser
            325             330             335

Val Glu Leu Pro Phe Val Leu Met His Pro Lys Pro His Asp His Ile
            340             345             350

Pro Leu Pro Arg Pro Gln Ser Ala Ala Pro Glu Thr Asp Val Pro Val
            355             360             365

Asp Thr Asn Leu Ile Glu Phe Asp Thr Asn Tyr Ala Thr Asp Asp Asp
        370             375             380

Ile Val Phe Glu Asp Phe Ala Arg Leu Arg Leu Lys Gly Met Lys Asp
385             390             395             400

Asp Asp Tyr Asp Asp Gln Leu Cys
            405
```

```
<210> SEQ ID NO 8
<211> LENGTH: 7100
<212> TYPE: DNA
<213> ORGANISM: Artificial Sequence
<220> FEATURE:
<223> OTHER INFORMATION: BArr 3D plasmid
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1039)..(1864)
<223> OTHER INFORMATION: CMV intron A
<220> FEATURE:
<221> NAME/KEY: misc_feature
<222> LOCATION: (1936)..(3162)
<223> OTHER INFORMATION: B-arrestin
<220> FEATURE:
<221> NAME/KEY: misc_feature
<222> LOCATION: (3163)..(3171)
```

-continued

```
<223> OTHER INFORMATION: linker
<220> FEATURE:
<221> NAME/KEY: misc_feature
<222> LOCATION: (3172)..(3888)
<223> OTHER INFORMATION: cpmNeon
<220> FEATURE:
<221> NAME/KEY: misc_feature
<222> LOCATION: (4030)..(4254)
<223> OTHER INFORMATION: bGH poly(A) signal
<220> FEATURE:
<221> NAME/KEY: misc_feature
<222> LOCATION: (4849)..(5437)
<223> OTHER INFORMATION: ori
<220> FEATURE:
<221> NAME/KEY: misc_feature
<222> LOCATION: (5980)..(6795)
<223> OTHER INFORMATION: KanR

<400> SEQUENCE: 8
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg ggtgaaatac cgcacagatg cgtaaggaga aaataccgca tcagattggc     240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca gagtgacgt aagtaccgcc tatagactct ataggcacac ccctttggct    1080
cttatgcatg ctatactgtt tttggcttgg ggcctataca ccccgcttc cttatgctat    1140 aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt attttttacag    1320 gatggggtcc catttattat ttacaaattc acatatacaa caacgccgtc ccccgtgccc    1380
gcagttttta ttaaacatag cgtgggatct ccacgcgaat ctcgggtacg tgttccggac    1440
atgggctctt ctccggtagc ggcggagctt ccacatccga gccctggtcc catgcctcca    1500
gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgc ctgacgcaga tggaagactt aaggcagcgg    1680
cagaagaaga tgcaggcagc tgagttgttg tattctgata gagtcagag gtaactcccg    1740 ttgcggtgct gttaacggtg gagggcagtg tagtctgagc agtactcgtt gctgccgcgc    1800
```

-continued

```
gcgccaccag acataatagc tgacagacta acagactgtt cctttccatg ggtcttttct   1860
gcagtcaccg tcgtcgacac gtgtgatcag atatacgact cactataggg agacccaagc   1920
tggctagcgt ttaccatggg ggagaaaccc gggaccaggg tcttcaagaa gtcgagccct   1980
aactgcaagc tcaccgtgta cttgggcaag cgggacttcg tagatcacct ggacaaagtg   2040
gaccctgtag atggcgtggt gcttgtggac cctgactacc tgaaggaccg caaagtgttt   2100
gtgaccctca cctgcgcctt ccgctatggc cgtgaagacc tggatgtgct gggcttgtcc   2160
ttccgcaaag acctgttcat cgccacctac caggccttcc ccccggtgcc caacccaccc   2220 cggccccca cccgcctgca ggaccggctg ctgaggaagc tgggccagca tgcccacccc   2280
ttcttcttca ccatacccca gaatcttcca tgctccgtca cactgcagcc aggcccagag   2340
gatacaggaa aggcctgcgg cgtagacttt gagattcgag ccttctgtgc taaatcacta   2400
gaagagaaaa gccacaaaag gaactctgtg cggctggtga tccgaaaggt gcagttcgcc   2460
ccggagaaac ccgcccccca gccttcagcc gaaaccacac gccacttcct catgtctgac   2520
cggtccctgc acctcgaggc ttccctggac aaggagctgt actaccatgg ggagcccctc   2580
aatgtaaatg tccacgtcac caacaactcc accaagaccg tcaagaagat caaagtctct   2640
gtgagacagt acgccgacat ctgcctcttc agcaccgccc agtacaagtg tcctgtggct   2700
caactcgaac aagatgacca ggtatctccc agctccacat tctgtaaggt gtacaccata   2760
accccactgc tcagcgacaa ccgggagaag cggggtctcg ccctggatgg gaaactcaag   2820
cacgaggaca ccaacctggc ttccagcacc atcgtgaagg agggtgccaa caaggaggtg   2880
ctgggaatcc tggtgtccta cagggtcaag gtgaagctgg tggtgtctcg aggcggggat   2940
gtctctgtgg agctgccttt tgttcttatg cacccccaagc cccacgacca catccccctc   3000
cccagacccc agtcagccgc tccggagaca gatgtccctg tggacaccaa cctcattgaa   3060
tttgatacca actatgccac agatgatgac attgtgtttg aggactttgc ccggcttcgg   3120 ctgaaggga tgaaggatga cgactatgat gatcaactct gcccctcgca ttcgaagaag   3180
acttacccca acgacaaaac catcatcagt accttttaagt ggagttacac cactggaaat   3240
ggcaagcgct accggagcac tgcgcggacc acctacacct tgccaagcc aatggcggct   3300 aactatctga agaaccagcc gatgtacgtg ttccgtaaga cggagctcaa gcactccaag   3360
accgagctca acttcaagga gtggcaaaag gcctttaccg atgtgatggg catggacgag   3420
ctgtacaagg gcggtaccgg agggagcatg gtgagcaagg gcgaggagga taacatggcc   3480
tctctcccag cgacacatga gttacacatc tttggctcca tcaacggtgt ggactttgac   3540
atggtgggtc agggcaccgg caatccaaat gatggttatg aggagttaaa cctgaagtcc   3600
accaagggtg acctccagtt ctcccctgg attctggtcc ctcatatcgg gtatggcttc   3660
catcagtacc tgccctaccc tgacgggatg tcgcctttcc aggccgccat ggtagatggc   3720
tccggatacc aagtccatcg cacaatgcag tttgaagatg gtgcctccct tactgttaac   3780
taccgctaca cctacgaggg aagccacatc aaaggagagg cccaggtgaa ggggactggt   3840
ttccctgctg acggtcctgt gatgaccaac tcgctgaccg ctgcgtcgta gcgcgccctc   3900
gactgtgcct tctagttgcc agccatctgt atcgcggccg ctctagacca ggcgcctgga   3960
tccagatcac ttctggctaa taaaagatca gagctctaga gatctgtgtg ttggtttttt   4020
gtggatctgc tgtgccttct agttgccagc catctgttgt ttgcccctcc ccgtgcctt   4080 ccttgaccct ggaaggtgcc actcccactg tcctttccta ataaaatgag gaaattgcat   4140
```

-continued

```
cgcattgtct gagtaggtgt cattctattc tgggggtgg ggtggggcag cacagcaagg      4200
gggaggattg ggaagacaat agcaggcatg ctggggatgc ggtgggctct atgggtacct      4260
ctctctctct ctctctctct ctctctctct ctctctctcg gtacctctct ctctctctct      4320
ctctctctct ctctctctct ctctcggtac caggtgctga agaattgacc cggttcctcc      4380
tgggccagaa agaagcaggc acatcccctt ctctgtgaca caccctgtcc acgcccctgg      4440
ttcttagttc cagccccact cataggacac tcatagctca ggagggctcc gccttcaatc      4500
ccacccgcta aagtacttgg agcggtctct ccctccctca tcagcccacc aaaccaaacc      4560
tagcctccaa gagtgggaag aaattaaagc aagataggct attaagtgca gagggagaga      4620
aaatgcctcc aacatgtgag gaagtaatga gagaaatcat agaatttctt ccgcttcctc      4680
gctcactgac tcgctgcgct cggtcgttcg gctgcggcga gcggtatcag ctcactcaaa      4740
ggcggtaata cggttatcca cagaatcagg ggataacgca ggaaagaaca tgtgagcaaa      4800
aggccagcaa aaggccagga accgtaaaaa ggccgcgttg ctggcgtttt tccataggct      4860
ccgcccccct gacgagcatc acaaaaatcg acgctcaagt cagaggtggc gaaacccgac      4920
aggactataa agataccagg cgtttccccc tggaagctcc ctcgtgcgct ctcctgttcc      4980
gaccctgccg cttaccggat acctgtccgc ctttctccct tcgggaagcg tggcgctttc      5040
tcaatgctca cgctgtaggt atctcagttc ggtgtaggtc gttcgctcca agctgggctg      5100
tgtgcacgaa ccccccgttc agcccgaccg ctgcgcctta tccggtaact atcgtcttga      5160
gtccaacccg gtaagacacg acttatcgcc actggcagca gccactggta acaggattag      5220
cagagcgagg tatgtaggcg gtgctacaga gttcttgaag tggtggccta actacggcta      5280
cactagaagg acagtatttg gtatctgcgc tctgctgaag ccagttacct tcggaaaaag      5340
agttggtagc tcttgatccg gcaaacaaac caccgctggt agcggtggtt ttttgtttg      5400 caagcagcag attacgcgca gaaaaaaagg atctcaagaa gatcctttga tcttttctac      5460
ggggtctgac gctcagtgga acgaaaactc acgttaaggg attttggtca tgagattatc      5520
aaaaaggatc ttcacctaga tccttttaaa ttaaaaatga agttttaaat caatctaaag      5580
tatatatgag taaacttggt ctgacagtta ccaatgctta atcagtgagg cacctatctc      5640
agcgatctgt ctatttcgtt catccatagt tgcctgactc cggggggggg gggcgctgag      5700
gtctgcctcg tgaagaaggt gttgctgact cataccaggc ctgaatcgcc ccatcatcca      5760
gccagaaagt gagggagcca cggttgatga gagctttgtt gtaggtggac cagttggtga      5820
ttttgaactt ttgctttgcc acggaacggt ctgcgttgtc gggaagatgc gtgatctgat      5880
ccttcaactc agcaaaagtt cgatttattc aacaaagccg ccgtcccgtc aagtcagcgt      5940
aatgctctgc cagtgttaca accaattaac caattctgat tagaaaaact catcgagcat      6000
caaatgaaac tgcaatttat tcatatcagg attatcaata ccatattttt gaaaaagccg      6060
tttctgtaat gaaggagaaa actcaccgag gcagttccat aggatggcaa gatcctggta      6120
tcggtctgcg attccgactc gtccaacatc aatacaacct attaatttcc cctcgtcaaa      6180
aataaggtta tcaagtgaga aatcaccatg agtgacgact gaatccggtg agaatggcaa      6240
aagcttatgc atttctttcc agacttgttc aacaggccag ccattacgct cgtcatcaaa      6300
atcactcgca tcaaccaaac cgttattcat tcgtgattgc gcctgagcga cgcgaaatac      6360
gcgatcgctg ttaaaaggac aattacaaac aggaatcgaa tgcaaccggc gcaggaacac      6420
tgccagcgca tcaacaatat tttcacctga atcaggatat tcttctaata cctggaatgc      6480
tgttttcccg gggatcgcag tggtgagtaa ccatgcatca tcaggagtac ggataaaatg      6540
```

-continued

```
cttgatggtc ggaagaggca taaattccgt cagccagttt agtctgacca tctcatctgt      6600
aacatcattg gcaacgctac ctttgccatg tttcagaaac aactctggcg catcgggctt      6660
cccatacaat cgatagattg tcgcacctga ttgcccgaca ttatcgcgag cccatttata      6720
cccatataaa tcagcatcca tgttggaatt taatcgcggc ctcgagcaag acgtttcccg      6780
ttgaatatgg ctcataacac cccttgtatt actgtttatg taagcagaca gttttattgt      6840
tcatgatgat atattttat cttgtgcaat gtaacatcag agattttgag acacaacgtg      6900
gctttccccc ccccccatt attgaagcat ttatcagggt tattgtctca tgagcggata      6960
catatttgaa tgtatttaga aaataaaca aataggggtt ccgcgcacat ttccccgaaa      7020
agtgccacct gacgtctaag aaaccattat tatcatgaca ttaacctata aaaataggcg      7080
tatcacgagg ccctttcgtc                                                 7100

<210> SEQ ID NO 9
<211> LENGTH: 1953
<212> TYPE: DNA
<213> ORGANISM: Artificial Sequence
<220> FEATURE:
<223> OTHER INFORMATION: BArr 3D coding sequence
<220> FEATURE:
<221> NAME/KEY: misc_feature
<222> LOCATION: (1)..(1227)
<223> OTHER INFORMATION: B-arrestin
<220> FEATURE:
<221> NAME/KEY: misc_feature
<222> LOCATION: (1228)..(1236)
<223> OTHER INFORMATION: linker
<220> FEATURE:
<221> NAME/KEY: misc_feature
<222> LOCATION: (1237)..(1953)
<223> OTHER INFORMATION: cpmNeon

<400> SEQUENCE: 9 atggggaga aacccgggac cagggtcttc aagaagtcga gccctaactg caagctcacc        60
gtgtacttgg gcaagcggga cttcgtagat cacctggaca aagtggaccc tgtagatggc       120
gtggtgcttg tggaccctga ctacctgaag gaccgcaaag tgtttgtgac cctcacctgc       180
gccttccgct atggccgtga agacctggat gtgctgggct tgtccttccg caaagacctg       240
ttcatcgcca cctaccaggc cttccccccg gtgcccaacc caccccggcc cccacccgc        300 ctgcaggacc ggctgctgag gaagctgggc agcatgccc accccttctt cttcaccata       360
ccccagaatc ttccatgctc cgtcacactg agccaggcc agaggatac aggaaaggcc        420 tgcggcgtag actttgagat tcgagccttc tgtgctaaat cactagaaga gaaaagccac      480
aaaaggaact ctgtgcggct ggtgatccga aaggtgcagt cgccccgga gaaacccggc        540 cccagcctt cagccgaaac cacacgccac ttcctcatgt ctgaccggtc cctgcacctc       600
gaggcttccc tggacaagga gctgtactac catgggggagc ccctcaatgt aaatgtccac      660
gtcaccaaca actccaccaa gaccgtcaag aagatcaaag tctctgtgag acagtacgcc       720
gacatctgcc tcttcagcac cgcccagtac aagtgtcctg tggctcaact cgaacaagat      780
gaccaggtat ctcccagctc cacattctgt aaggtgtaca ccataacccc actgctcagc      840
gacaaccggg agaagcgggg tctcgccctg gatgggaaac tcaagcacga ggacaccaac      900
ctggcttcca gcaccatcgt gaaggagggt gccaacaagg aggtgctggg aatcctggtg      960
tcctacaggg tcaaggtgaa gctggtggtg tctcgaggcg gggatgtctc tgtggagctg     1020 cctttgttc ttatgcaccc caagccccac gaccacatcc ccctcccag accccagtca      1080
```

```
gccgctccgg agacagatgt ccctgtggac accaacctca ttgaatttga taccaactat   1140
gccacagatg atgacattgt gtttgaggac tttgcccggc ttcggctgaa ggggatgaag   1200
gatgacgact atgatgatca actctgcccc tcgcattcga agaagactta ccccaacgac   1260
aaaaccatca tcagtacctt taagtggagt tacaccactg gaaatggcaa gcgctaccgg   1320
agcactgcgc ggaccaccta cacctttgcc aagccaatgg cggctaacta tctgaagaac   1380
cagccgatgt acgtgttccg taagacggag ctcaagcact ccaagaccga gctcaacttc   1440
aaggagtggc aaaaggcctt taccgatgtg atgggcatgg acgagctgta caagggcggt   1500
accggaggga gcatggtgag caagggcgag gaggataaca tggcctctct cccagcgaca   1560
catgagttac acatctttgg ctccatcaac ggtgtggact ttgacatggt gggtcagggc   1620
accggcaatc caaatgatgg ttatgaggag ttaaacctga gtccaccaa gggtgacctc   1680 cagttctccc cctggattct ggtccctcat atcgggtatg gcttccatca gtacctgccc   1740
taccctgacg ggatgtcgcc tttccaggcc gccatggtag atggctccgg ataccaagtc   1800
catcgcacaa tgcagtttga agatggtgcc tcccttactg ttaactaccg ctacacctac   1860
gagggaagcc acatcaaagg agaggcccag gtgaagggga ctggtttccc tgctgacggt   1920
cctgtgatga ccaactcgct gaccgctgcg tcg                                 1953
```

```
<210> SEQ ID NO 10
<211> LENGTH: 651
<212> TYPE: PRT
<213> ORGANISM: Artificial Sequence
<220> FEATURE:
<223> OTHER INFORMATION: BArr 3d coding sequence
<220> FEATURE:
<221> NAME/KEY: SITE
<222> LOCATION: (1)..(409)
<223> OTHER INFORMATION: B-arrestin
<220> FEATURE:
<221> NAME/KEY: SITE
<222> LOCATION: (410)..(412)
<223> OTHER INFORMATION: linker
<220> FEATURE:
<221> NAME/KEY: SITE
<222> LOCATION: (413)..(651)
<223> OTHER INFORMATION: cpmNeon

<400> SEQUENCE: 10

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
        50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
                100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140
```

-continued

```
Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
                180                 185                 190

Met Ser Asp Arg Ser Leu His Leu Glu Ala Ser Leu Asp Lys Glu Leu
                195                 200                 205

Tyr Tyr His Gly Glu Pro Leu Asn Val Asn Val His Val Thr Asn Asn
        210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
                260                 265                 270

Tyr Thr Ile Thr Pro Leu Leu Ser Asp Asn Arg Glu Lys Arg Gly Leu
        275                 280                 285

Ala Leu Asp Gly Lys Leu Lys His Glu Asp Thr Asn Leu Ala Ser Ser
        290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
                340                 345                 350

Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
        370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys Pro Ser His Ser Lys Lys Thr
                405                 410                 415

Tyr Pro Asn Asp Lys Thr Ile Ile Ser Thr Phe Lys Trp Ser Tyr Thr
                420                 425                 430

Thr Gly Asn Gly Lys Arg Tyr Arg Ser Thr Ala Arg Thr Thr Tyr Thr
        435                 440                 445

Phe Ala Lys Pro Met Ala Ala Asn Tyr Leu Lys Asn Gln Pro Met Tyr
        450                 455                 460

Val Phe Arg Lys Thr Glu Leu Lys His Ser Lys Thr Glu Leu Asn Phe
465                 470                 475                 480

Lys Glu Trp Gln Lys Ala Phe Thr Asp Val Met Gly Met Asp Glu Leu
                485                 490                 495

Tyr Lys Gly Gly Thr Gly Gly Ser Met Val Ser Lys Gly Glu Glu Asp
        500                 505                 510

Asn Met Ala Ser Leu Pro Ala Thr His Glu Leu His Ile Phe Gly Ser
        515                 520                 525

Ile Asn Gly Val Asp Phe Asp Met Val Gly Gln Gly Thr Gly Asn Pro
        530                 535                 540

Asn Asp Gly Tyr Glu Glu Leu Asn Leu Lys Ser Thr Lys Gly Asp Leu
545                 550                 555                 560

Gln Phe Ser Pro Trp Ile Leu Val Pro His Ile Gly Tyr Gly Phe His
```

-continued

```
                565              570              575
Gln Tyr Leu Pro Tyr Pro Asp Gly Met Ser Pro Phe Gln Ala Ala Met
            580              585              590

Val Asp Gly Ser Gly Tyr Gln Val His Arg Thr Met Gln Phe Glu Asp
        595              600              605

Gly Ala Ser Leu Thr Val Asn Tyr Arg Tyr Thr Tyr Glu Gly Ser His
    610              615              620

Ile Lys Gly Glu Ala Gln Val Lys Gly Thr Gly Phe Pro Ala Asp Gly
625              630              635              640

Pro Val Met Thr Asn Ser Leu Thr Ala Ala Ser
            645              650
```

```
<210> SEQ ID NO 11
<211> LENGTH: 1227
<212> TYPE: DNA
<213> ORGANISM: Artificial Sequence
<220> FEATURE:
<223> OTHER INFORMATION: BArr 3D - Beta-arrestin-2
<220> FEATURE:
<221> NAME/KEY: misc_feature
<222> LOCATION: (1)..(1227)
<223> OTHER INFORMATION: B-Arrestin

<400> SEQUENCE: 11
atgggggaga aacccgggac cagggtcttc aagaagtcga gccctaactg caagctcacc      60
gtgtacttgg gcaagcggga cttcgtagat cacctggaca aagtggaccc tgtagatggc     120
gtggtgcttg tggaccctga ctacctgaag gaccgcaaag tgtttgtgac cctcacctgc     180
gccttccgct atggccgtga agacctggat gtgctgggct tgtccttccg caaagacctg     240
ttcatcgcca cctaccaggc cttccccccg gtgcccaacc caccccggcc cccaccccgc     300
ctgcaggacc ggctgctgag gaagctgggc cagcatgccc accccttctt cttcaccata     360
ccccagaatc ttccatgctc cgtcacactg cagccaggcc cagaggatac aggaaaggcc     420
tgcggcgtag actttgagat tcgagccttc tgtgctaaat cactagaaga gaaaagccac     480
aaaaggaact ctgtgcggct ggtgatccga aaggtgcagt tcgccccgga gaaacccggc     540
ccccagcctt cagccgaaac cacacgccac ttcctcatgt ctgaccggtc cctgcacctc     600
gaggcttccc tggacaagga gctgtactac catgggagc ccctcaatgt aaatgtccac     660
gtcaccaaca actccaccaa gaccgtcaag aagatcaaag tctctgtgag acagtacgcc     720
gacatctgcc tcttcagcac cgcccagtac aagtgtcctg tggctcaact cgaacaagat     780
gaccaggtat ctcccagctc cacattctgt aaggtgtaca ccataacccc actgctcagc     840
gacaaccggg agaagcgggg tctcgccctg gatgggaaac tcaagcacga ggacaccaac     900
ctggcttcca gcaccatcgt gaaggagggt gccaacaagg aggtgctggg aatcctggtg     960
tcctacaggg tcaaggtgaa gctggtggtg tctcgaggcg gggatgtctc tgtggagctg    1020
ccttttgttc ttatgcaccc caagccccac gaccacatcc ccctcccag accccagtca    1080 gccgctccgg agacagatgt ccctgtggac accaacctca ttgaatttga taccaactat    1140
gccacagatg atgacattgt gtttgaggac tttgcccggc ttcggctgaa ggggatgaag    1200
gatgacgact atgatgatca actctgc                                        1227
```

```
<210> SEQ ID NO 12
<211> LENGTH: 409
<212> TYPE: PRT
<213> ORGANISM: Artificial Sequence
<220> FEATURE:
```

<223> OTHER INFORMATION: BArr 3D - Beta-arrestin-2
<220> FEATURE:
<221> NAME/KEY: SITE
<222> LOCATION: (1)..(409)
<223> OTHER INFORMATION: B-arrestin

<400> SEQUENCE: 12

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
        195                 200                 205

Tyr Tyr His Gly Glu Pro Leu Asn Val Asn Val His Val Thr Asn Asn
    210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
            260                 265                 270

Tyr Thr Ile Thr Pro Leu Leu Ser Asp Asn Arg Glu Lys Arg Gly Leu
    275                 280                 285

Ala Leu Asp Gly Lys Leu Lys His Glu Asp Thr Asn Leu Ala Ser Ser
    290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
            325                 330                 335

Ser Val Glu Leu Pro Phe Val Leu Met His Pro Lys Pro His Asp His
        340                 345                 350

Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
    370                 375                 380
```

```
Asp Ile Val Phe Glu Asp Phe Ala Arg Leu Arg Leu Lys Gly Met Lys
385                 390             395                 400

Asp Asp Asp Tyr Asp Asp Gln Leu Cys
                405
```

```
<210> SEQ ID NO 13
<211> LENGTH: 717
<212> TYPE: DNA
<213> ORGANISM: Artificial Sequence
<220> FEATURE:
<223> OTHER INFORMATION: BArr 3D - cpmNeonGreen
<220> FEATURE:
<221> NAME/KEY: misc_feature
<222> LOCATION: (1)..(717)
<223> OTHER INFORMATION: cpmNeonGreen

<400> SEQUENCE: 13
tcgaagaaga cttaccccaa cgacaaaacc atcatcagta cctttaagtg gagttacacc      60
actggaaatg gcaagcgcta ccggagcact gcgcggacca cctacacctt tgccaagcca     120
atggcggcta actatctgaa gaaccagccg atgtacgtgt tccgtaagac ggagctcaag     180
cactccaaga ccgagctcaa cttcaaggag tggcaaaagg cctttaccga tgtgatgggc     240
atggacgagc tgtacaaggg cggtaccgga gggagcatgg tgagcaaggg cgaggaggat     300
aacatggcct ctctcccagc gacacatgag ttacacatct ttggctccat caacggtgtg     360
gactttgaca tggtgggtca gggcaccggc aatccaaatg atggttatga ggagttaaac     420
ctgaagtcca ccaagggtga cctccagttc tcccctgga ttctggtccc tcatatcggg     480
tatggcttcc atcagtacct gccctaccct gacgggatgt cgcctttcca ggccgccatg     540
gtagatggct ccggatacca agtccatcgc acaatgcagt ttgaagatgg tgcctccctt     600
actgttaact accgctacac ctacgaggga agccacatca aggagaggc ccaggtgaag     660 gggactggtt tccctgctga cggtcctgtg atgaccaact cgctgaccgc tgcgtcg       717
```

```
<210> SEQ ID NO 14
<211> LENGTH: 239
<212> TYPE: PRT
<213> ORGANISM: Artificial Sequence
<220> FEATURE:
<223> OTHER INFORMATION: BArr 3D - cpmNeonGreen

<400> SEQUENCE: 14

Ser Lys Lys Thr Tyr Pro Asn Asp Lys Thr Ile Ile Ser Thr Phe Lys
1               5                   10                  15

Trp Ser Tyr Thr Thr Gly Asn Gly Lys Arg Tyr Arg Ser Thr Ala Arg
                20                  25                  30

Thr Thr Tyr Thr Phe Ala Lys Pro Met Ala Ala Asn Tyr Leu Lys Asn
            35                  40                  45

Gln Pro Met Tyr Val Phe Arg Lys Thr Glu Leu Lys His Ser Lys Thr
        50                  55                  60

Glu Leu Asn Phe Lys Glu Trp Gln Lys Ala Phe Thr Asp Val Met Gly
65                  70                  75                  80

Met Asp Glu Leu Tyr Lys Gly Gly Thr Gly Gly Ser Met Val Ser Lys
                85                  90                  95

Gly Glu Glu Asp Asn Met Ala Ser Leu Pro Ala Thr His Glu Leu His
            100                 105                 110

Ile Phe Gly Ser Ile Asn Gly Val Asp Phe Asp Met Val Gly Gln Gly
        115                 120                 125
```

-continued

```
Thr Gly Asn Pro Asn Asp Gly Tyr Glu Glu Leu Asn Leu Lys Ser Thr
    130                 135                 140

Lys Gly Asp Leu Gln Phe Ser Pro Trp Ile Leu Val Pro His Ile Gly
145                 150                 155                 160

Tyr Gly Phe His Gln Tyr Leu Pro Tyr Pro Asp Gly Met Ser Pro Phe
                165                 170                 175

Gln Ala Ala Met Val Asp Gly Ser Gly Tyr Gln Val His Arg Thr Met
            180                 185                 190

Gln Phe Glu Asp Gly Ala Ser Leu Thr Val Asn Tyr Arg Tyr Thr Tyr
        195                 200                 205

Glu Gly Ser His Ile Lys Gly Glu Ala Gln Val Lys Gly Thr Gly Phe
    210                 215                 220

Pro Ala Asp Gly Pro Val Met Thr Asn Ser Leu Thr Ala Ala Ser
225                 230                 235

<210> SEQ ID NO 15
<211> LENGTH: 7100
<212> TYPE: DNA
<213> ORGANISM: Artificial Sequence
<220> FEATURE:
<223> OTHER INFORMATION: BArr 3F plasmid
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1039)..(1864)
<223> OTHER INFORMATION: CMV intron A
<220> FEATURE:
<221> NAME/KEY: misc_feature
<222> LOCATION: (1936)..(3162)
<223> OTHER INFORMATION: B-arrestin
<220> FEATURE:
<221> NAME/KEY: misc_feature
<222> LOCATION: (3163)..(3171)
<223> OTHER INFORMATION: Critical linker sequence
<220> FEATURE:
<221> NAME/KEY: misc_feature
<222> LOCATION: (3172)..(3885)
<223> OTHER INFORMATION: cpmNeon
<220> FEATURE:
<221> NAME/KEY: misc_feature
<222> LOCATION: (4030)..(4254)
<223> OTHER INFORMATION: bGH poly(A) signal
<220> FEATURE:
<221> NAME/KEY: misc_feature
<222> LOCATION: (4849)..(5437)
<223> OTHER INFORMATION: ori
<220> FEATURE:
<221> NAME/KEY: misc_feature
<222> LOCATION: (5980)..(6795)
<223> OTHER INFORMATION: KanR

<400> SEQUENCE: 15
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc       180
accatatgcg ggtgaaatac cgcacagatg cgtaaggaga aaataccgca tcagattggc       240
tattggccat tgcatacgtt gtatccatat cataatatgt acatttatat tggctcatgt       300
ccaacattac cgccatgttg acattgatta ttgactagtt attaatagta atcaattacg       360
```

-continued

```
gggtcattag ttcatagccc atatatggag ttccgcgtta cataacttac ggtaaatggc     420
ccgcctggct gaccgcccaa cgaccccgc ccattgacgt caataatgac gtatgttccc      480
atagtaacgc caatagggac tttccattga cgtcaatggg tggagtattt acggtaaact     540
gcccacttgg cagtacatca agtgtatcat atgccaagta cgcccccat tgacgtcaat      600 gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca cccccgcttc cttatgctat    1140
aggtgatggt atagcttagc ctataggtgt gggttattga ccattattga ccactccct    1200 attggtgacg atactttcca ttactaatcc ataacatggc tctttgccac aactatctct    1260
attggctata tgccaatact ctgtccttca gagactgaca cggactctgt atttttacag    1320
gatggggtcc catttattat ttacaaattc acatatacaa caacgccgtc ccccgtgccc    1380
gcagttttta ttaaacatag cgtgggatct ccacgcgaat ctcgggtacg tgttccggac    1440
atgggctctt ctccggtagc ggcggagctt ccacatccga ccctggtcc catgcctcca    1500 gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
ttgcggtgct gttaacggtg gagggcagtg tagtctgagc agtactcgtt gctgccgcgc    1800
gcgccaccag acataatagc tgacagacta acagactgtt cctttccatg ggtctttct    1860 gcagtcaccg tcgtcgacac gtgtgatcag atatacgact cactataggg agacccaagc    1920
tggctagcgt ttaccatggg ggagaaaccc gggaccaggg tcttcaagaa gtcgagccct    1980
aactgcaagc tcaccgtgta cttgggcaag cgggacttcg tagatcacct ggacaaagtg    2040
gaccctgtag atggcgtggt gcttgtggac cctgactacc tgaaggaccg caaagtgttt    2100
gtgaccctca cctgcgcctt ccgctatggc cgtgaagacc tggatgtgct gggcttgtcc    2160
ttccgcaaag acctgttcat cgccacctac caggccttcc ccccggtgcc caacccacc    2220 cggcccccca cccgcctgca ggaccggctg ctgaggaagc tgggccagca tgcccacccc    2280
ttcttcttca ccatacccca gaatcttcca tgctccgtca cactgcagcc aggcccagag    2340
gatacaggaa aggcctgcgg cgtagacttt gagattcgag ccttctgtgc taaatcacta    2400
gaagagaaaa gccacaaaag gaactctgtg cggctggtga tccgaaaggt gcagttcgcc    2460
ccggagaaac ccgccccca gccttcagcc gaaaccacac gccacttcct catgtctgac    2520
cggtccctgc acctcgaggc ttccctggac aaggagctgt actaccatgg ggagcccctc    2580
aatgtaaatg tccacgtcac caacaactcc accaagaccg tcaagaagat caaagtctct    2640
gtgagacagt acgccgacat ctgcctcttc agcaccgccc agtacaagtg tcctgtggct    2700
caactcgaac aagatgacca ggtatctccc agctccacat tctgtaaggt gtacaccata    2760
```

-continued

```
accccactgc tcagcgacaa ccgggagaag cggggtctcg ccctggatgg gaaactcaag    2820
cacgaggaca ccaacctggc ttccagcacc atcgtgaagg agggtgccaa caaggaggtg    2880
ctgggaatcc tggtgtccta cagggtcaag gtgaagctgg tggtgtctcg aggcggggat    2940
gtctctgtgg agctgccttt tgttcttatg caccccaagc cccacgacca catccccctc    3000
cccagacccc agtcagccgc tccggagaca gatgtccctg tggacaccaa cctcattgaa    3060
tttgatacca actatgccac agatgatgac attgtgtttg aggactttgc ccggcttcgg    3120
ctgaagggga tgaaggatga cgactatgat gatcaactct gcccctcgca ttcgaagaag    3180
acttacccca cgacaaaac catcatcagt acctttaagt ggagttacac cactggaaat    3240
ggcaagcgct accggagcac tgcgcggacc acctacacct ttgccaagcc aatggcggct    3300
aactatctga agaaccagcc gatgtacgtg ttccgtaaga cggagctcaa gcactccaag    3360
accgagctca acttcaagga gtggcaaaag gcctttaccg atgtgatggg catggacgag    3420
ctgtacaagg gcggtaccgg agggagcatg gtgagcaagg gcgaggagga taacatggcc    3480
tctctcccag cgacacatga gttacacatc tttggctcca tcaacggtgt ggactttgac    3540
atggtgggtc agggcaccgg caatccaaat gatggttatg aggagttaaa cctgaagtcc    3600
accaagggtg acctccagtt ctccccctgg attctggtcc ctcatatcgg gtatggcttc    3660
catcagtacc tgccctaccc tgacgggatg tcgcctttcc aggccgccat ggtagatggc    3720
tccggatacc aagtccatcg cacaatgcag tttgaagatg gtgcctccct tactgttaac    3780
taccgctaca cctacgaggg aagccacatc aaaggagagg cccaggtgaa ggggactggt    3840
ttccctgctg acggtcctgt gatgaccaac tcgctgaccg ctgcggacta gcgcgccctc    3900
gactgtgcct tctagttgcc agccatctgt atcgcggccg ctctagacca ggcgcctgga    3960
tccagatcac ttctggctaa taaaagatca gagctctaga gatctgtgtg ttggtttttt    4020
gtggatctgc tgtgccttct agttgccagc catctgttgt ttgcccctcc cccgtgcctt    4080
ccttgaccct ggaaggtgcc actcccactg tcctttccta ataaaatgag gaaattgcat    4140
cgcattgtct gagtaggtgt cattctattc tggggggtgg ggtggggcag cacagcaagg    4200
gggaggattg ggaagacaat agcaggcatg ctggggatgc ggtgggctct atgggtacct    4260
ctctctctct ctctctctct ctctctctct ctctctctcg gtacctctct ctctctctct    4320
ctctctctct ctctctctct ctctcggtac caggtgctga agaattgacc cggttcctcc    4380
tgggccagaa agaagcaggc acatcccctt ctctgtgaca caccctgtcc acgcccctgg    4440
ttcttagttc cagccccact cataggacac tcatagctca ggagggctcc gccttcaatc    4500
ccacccgcta aagtacttgg agcggtctct ccctccctca tcagcccacc aaaccaaacc    4560
tagcctccaa gagtgggaag aaattaaagc aagataggct attaagtgca gagggagaga    4620
aaatgcctcc aacatgtgag gaagtaatga gagaaatcat agaatttctt ccgcttcctc    4680
gctcactgac tcgctgcgct cggtcgttcg gctgcggcga cggtatcag ctcactcaaa    4740 ggcggtaata cggttatcca cagaatcagg ggataacgca ggaaagaaca tgtgagcaaa    4800
aggccagcaa aaggccagga accgtaaaaa ggccgcgttg ctggcgtttt tccataggct    4860
ccgcccccct gacgagcatc acaaaaatcg acgctcaagt cagaggtggc gaaacccgac    4920
aggactataa agataccagg cgtttccccc tggaagctcc ctcgtgcgct ctcctgttcc    4980
gaccctgccg cttaccggat acctgtccgc ctttctccct tcgggaagcg tggcgctttc    5040
tcaatgctca cgctgtaggt atctcagttc ggtgtaggtc gttcgctcca agctgggctg    5100
```

```
tgtgcacgaa cccccgttc agcccgaccg ctgcgcctta tccggtaact atcgtcttga    5160
gtccaacccg gtaagacacg acttatcgcc actggcagca gccactggta acaggattag    5220
cagagcgagg tatgtaggcg gtgctacaga gttcttgaag tggtggccta actacggcta    5280
cactagaagg acagtatttg gtatctgcgc tctgctgaag ccagttacct tcggaaaaag    5340
agttggtagc tcttgatccg gcaaacaaac caccgctggt agcggtggtt tttttgtttg    5400
caagcagcag attacgcgca gaaaaaaagg atctcaagaa gatcctttga tcttttctac    5460
ggggtctgac gctcagtgga acgaaaactc acgttaaggg attttggtca tgagattatc    5520
aaaaaggatc ttcacctaga tcctttaaa ttaaaaatga gtttaaat caatctaaag    5580 tatatatgag taaacttggt ctgacagtta ccaatgctta atcagtgagg cacctatctc    5640
agcgatctgt ctatttcgtt catccatagt tgcctgactc cggggggggg gggcgctgag    5700
gtctgcctcg tgaagaaggt gttgctgact cataccaggc ctgaatcgcc ccatcatcca    5760
gccagaaagt gagggagcca cggttgatga gagctttgtt gtaggtggac cagttggtga    5820
ttttgaactt ttgctttgcc acggaacggt ctgcgttgtc gggaagatgc gtgatctgat    5880
ccttcaactc agcaaaagtt cgatttattc aacaaagccg ccgtcccgtc aagtcagcgt    5940
aatgctctgc cagtgttaca accaattaac caattctgat tagaaaaact catcgagcat    6000
caaatgaaac tgcaatttat tcatatcagg attatcaata ccatatttt gaaaaagccg    6060 tttctgtaat gaaggagaaa actcaccgag gcagttccat aggatggcaa gatcctggta    6120
tcggtctgcg attccgactc gtccaacatc aatacaacct attaatttcc cctcgtcaaa    6180
aataaggtta tcaagtgaga atcaccatg agtgacgact gaatccggtg agaatggcaa    6240
aagcttatgc atttctttcc agacttgttc aacaggccag ccattacgct cgtcatcaaa    6300
atcactcgca tcaaccaaac cgttattcat tcgtgattgc gcctgagcga gacgaaatac    6360
gcgatcgctg ttaaaggac aattacaaac aggaatcgaa tgcaaccggc gcaggaacac    6420
tgccagcgca tcaacaatat tttcacctga atcaggatat tcttctaata cctggaatgc    6480
tgttttcccg gggatcgcag tggtgagtaa ccatgcatca tcaggagtac ggataaaatg    6540
cttgatggtc ggaagaggca taaattccgt cagccagttt agtctgacca tctcatctgt    6600
aacatcattg gcaacgctac ctttgccatg tttcagaaac aactctggcg catcgggctt    6660
cccatacaat cgatagattg tcgcacctga ttgcccgaca ttatcgcgag cccatttata    6720
cccatataaa tcagcatcca tgttggaatt taatcgcggc ctcgagcaag acgtttcccg    6780
ttgaatatgg ctcataacac cccttgtatt actgtttatg taagcagaca gttttattgt    6840
tcatgatgat atattttat cttgtgcaat gtaacatcag agattttgag acacaacgtg    6900
gctttccccc cccccccatt attgaagcat ttatcagggt tattgtctca tgagcggata    6960
catatttgaa tgtatttaga aaataaaca aataggggtt ccgcgcacat ttccccgaaa    7020
agtgccacct gacgtctaag aaaccattat tatcatgaca ttaacctata aaaataggcg    7080
tatcacgagg ccctttcgtc                                                7100
```

<210> SEQ ID NO 16
<211> LENGTH: 1950
<212> TYPE: DNA
<213> ORGANISM: Artificial Sequence
<220> FEATURE:
<223> OTHER INFORMATION: BArr 3F coding sequence
<220> FEATURE:
<221> NAME/KEY: misc_feature
<222> LOCATION: (1)..(1227)
<223> OTHER INFORMATION: B-arrestin -continued

```
<220> FEATURE:
<221> NAME/KEY: misc_feature
<222> LOCATION: (1228)..(1236)
<223> OTHER INFORMATION: Critical linker sequence
<220> FEATURE:
<221> NAME/KEY: misc_feature
<222> LOCATION: (1237)..(1950)
<223> OTHER INFORMATION: cpmNeon

<400> SEQUENCE: 16 atggggggaga aacccgggac cagggtcttc aagaagtcga gccctaactg caagctcacc         60
gtgtacttgg gcaagcggga cttcgtagat cacctggaca aagtggaccc tgtagatggc        120
gtggtgcttg tggaccctga ctacctgaag gaccgcaaag tgtttgtgac cctcacctgc        180
gccttccgct atggccgtga agacctggat gtgctgggct tgtccttccg caaagacctg        240
ttcatcgcca cctaccaggc cttcccccccg gtgcccaacc cacccccggcc ccccacccgc        300 ctgcaggacc ggctgctgag gaagctgggc cagcatgccc acccccttctt cttcaccata        360 ccccagaatc ttccatgctc cgtcacactg cagccaggcc cagaggatac aggaaaggcc        420
tgcggcgtag actttgagat tcgagccttc tgtgctaaat cactagaaga gaaaagccac        480
aaaaggaact ctgtgcggct ggtgatccga aaggtgcagt tcgccccgga gaaacccggc        540
ccccagcctt cagccgaaac cacacgccac ttcctcatgt ctgaccggtc cctgcacctc        600
gaggcttccc tggacaagga gctgtactac catggggagc ccctcaatgt aaatgtccac        660
gtcaccaaca actccaccaa gaccgtcaag aagatcaaag tctctgtgag acagtacgcc        720
gacatctgcc tcttcagcac cgcccagtac aagtgtcctg tggctcaact cgaacaagat        780
gaccaggtat ctcccagctc cacattctgt aaggtgtaca ccataacccc actgctcagc        840
gacaaccggg agaagcgggg tctcgccctg gatgggaaac tcaagcacga ggacaccaac        900
ctggcttcca gcaccatcgt gaaggagggt gccaacaagg aggtgctggg aatcctggtg        960
tcctacaggg tcaaggtgaa gctggtggtg tctcgaggcg gggatgtctc tgtggagctg       1020 cctttttgttc ttatgcaccc caagccccac gaccacatcc ccctcccag accccagtca      1080 gccgctccgg agacagatgt ccctgtggac accaacctca ttgaatttga taccaactat       1140
gccacagatg atgacattgt gtttgaggac tttgcccggc ttcggctgaa ggggatgaag       1200
gatgacgact atgatgatca actctgcccc tcgcattcga agaagactta ccccaacgac       1260
aaaaccatca tcagtacctt taagtggagt tacaccactg gaaatggcaa gcgctaccgg       1320
agcactgcgc ggaccaccta cacctttgcc aagccaatgg cggctaacta tctgaagaac       1380
cagccgatgt acgtgttccg taagacggag ctcaagcact ccaagaccga gctcaacttc       1440
aaggagtggc aaaaggcctt taccgatgtg atgggcatgg acgagctgta caagggcggt       1500 accgaggga gcatggtgag caagggcgag gaggataaca tggcctctct cccagcgaca       1560
catgagttac acatctttgg ctccatcaac ggtgtggact ttgacatggt gggtcagggc       1620
accggcaatc aaatgatgg ttatgaggag ttaaacctga agtccaccaa gggtgacctc       1680
cagttctccc cctggattct ggtccctcat atcgggtatg gcttccatca gtacctgccc       1740 tacccttgacg ggatgtcgcc tttccaggcc gccatggtag atggctccgg ataccaagtc       1800
catcgcacaa tgcagtttga agatggtgcc tcccttactg ttaactaccg ctacacctac       1860
gagggaagcc acatcaaagg agaggcccag gtgaagggga ctggtttccc tgctgacggt       1920
cctgtgatga ccaactcgct gaccgctgcg                                          1950
```

```
<210> SEQ ID NO 17
```

-continued

```
<211> LENGTH: 650
<212> TYPE: PRT
<213> ORGANISM: Artificial Sequence
<220> FEATURE:
<223> OTHER INFORMATION: BArr 3F coding sequence
<220> FEATURE:
<221> NAME/KEY: SITE
<222> LOCATION: (1)..(409)
<223> OTHER INFORMATION: B-arrestin
<220> FEATURE:
<221> NAME/KEY: SITE
<222> LOCATION: (410)..(412)
<223> OTHER INFORMATION: Critical linker sequence
<220> FEATURE:
<221> NAME/KEY: SITE
<222> LOCATION: (413)..(650)
<223> OTHER INFORMATION: cpmNeon

<400> SEQUENCE: 17

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
            115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
            195                 200                 205

Tyr Tyr His Gly Glu Pro Leu Asn Val Asn Val His Val Thr Asn Asn
    210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
            260                 265                 270

Tyr Thr Ile Thr Pro Leu Leu Ser Asp Asn Arg Glu Lys Arg Gly Leu
            275                 280                 285

Ala Leu Asp Gly Lys Leu Lys His Glu Asp Thr Asn Leu Ala Ser Ser
    290                 295                 300

Thr Ile Val Lys Glu Gly Ala Asn Lys Glu Val Leu Gly Ile Leu Val
305                 310                 315                 320
```

```
Ser Tyr Arg Val Lys Val Lys Leu Val Val Ser Arg Gly Gly Asp Val
            325                 330                 335

Ser Val Glu Leu Pro Phe Val Leu Met His Pro Lys Pro His Asp His
            340                 345                 350

Ile Pro Leu Pro Arg Pro Gln Ser Ala Ala Pro Glu Thr Asp Val Pro
            355                 360                 365

Val Asp Thr Asn Leu Ile Glu Phe Asp Thr Asn Tyr Ala Thr Asp Asp
    370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys Pro Ser His Ser Lys Lys Thr
                405                 410                 415

Tyr Pro Asn Asp Lys Thr Ile Ile Ser Thr Phe Lys Trp Ser Tyr Thr
                420                 425                 430

Thr Gly Asn Gly Lys Arg Tyr Arg Ser Thr Ala Arg Thr Thr Tyr Thr
            435                 440                 445

Phe Ala Lys Pro Met Ala Ala Asn Tyr Leu Lys Asn Gln Pro Met Tyr
    450                 455                 460

Val Phe Arg Lys Thr Glu Leu Lys His Ser Lys Thr Glu Leu Asn Phe
465                 470                 475                 480

Lys Glu Trp Gln Lys Ala Phe Thr Asp Val Met Gly Met Asp Glu Leu
                485                 490                 495

Tyr Lys Gly Gly Thr Gly Gly Ser Met Val Ser Lys Gly Glu Glu Asp
            500                 505                 510

Asn Met Ala Ser Leu Pro Ala Thr His Glu Leu His Ile Phe Gly Ser
            515                 520                 525

Ile Asn Gly Val Asp Phe Asp Met Val Gly Gln Gly Thr Gly Asn Pro
    530                 535                 540

Asn Asp Gly Tyr Glu Glu Leu Asn Leu Lys Ser Thr Lys Gly Asp Leu
545                 550                 555                 560

Gln Phe Ser Pro Trp Ile Leu Val Pro His Ile Gly Tyr Gly Phe His
                565                 570                 575

Gln Tyr Leu Pro Tyr Pro Asp Gly Met Ser Pro Phe Gln Ala Ala Met
            580                 585                 590

Val Asp Gly Ser Gly Tyr Gln Val His Arg Thr Met Gln Phe Glu Asp
            595                 600                 605

Gly Ala Ser Leu Thr Val Asn Tyr Arg Tyr Thr Tyr Glu Gly Ser His
    610                 615                 620

Ile Lys Gly Glu Ala Gln Val Lys Gly Thr Gly Phe Pro Ala Asp Gly
625                 630                 635                 640

Pro Val Met Thr Asn Ser Leu Thr Ala Ala
            645                 650
```

<210> SEQ ID NO 18
<211> LENGTH: 1227
<212> TYPE: DNA
<213> ORGANISM: Artificial Sequence
<220> FEATURE:
<223> OTHER INFORMATION: BArr 3F - Beta-arrestin-2
<220> FEATURE:
<221> NAME/KEY: misc_feature
<222> LOCATION: (1)..(1227)
<223> OTHER INFORMATION: B-arrestin

<400> SEQUENCE: 18
atgggggaga aacccgggac cagggtcttc aagaagtcga gccctaactg caagctcacc     60

-continued

```
gtgtacttgg gcaagcggga cttcgtagat cacctggaca aagtggaccc tgtagatggc    120
gtggtgcttg tggaccctga ctacctgaag gaccgcaaag tgtttgtgac cctcacctgc    180
gccttccgct atggccgtga agacctggat gtgctgggct tgtccttccg caaagacctg    240
ttcatcgcca cctaccaggc cttcccccccg gtgcccaacc caccccggcc ccccacccgc    300
ctgcaggacc ggctgctgag gaagctgggc cagcatgccc accccttctt cttcaccata    360
ccccagaatc ttccatgctc cgtcacactg cagccaggcc cagaggatac aggaaaggcc    420
tgcggcgtag actttgagat tcgagccttc tgtgctaaat cactagaaga gaaaagccac    480
aaaaggaact ctgtgcggct ggtgatccga aaggtgcagt tcgcccccgga gaaacccggc    540 ccccagcctt cagccgaaac cacacgccac ttcctcatgt ctgaccggtc cctgcacctc    600
gaggcttccc tggacaagga gctgtactac catgggggagc ccctcaatgt aaatgtccac    660
gtcaccaaca actccaccaa gaccgtcaag aagatcaaag tctctgtgag acagtacgcc    720
gacatctgcc tcttcagcac cgcccagtac aagtgtcctg tggctcaact cgaacaagat    780
gaccaggtat ctcccagctc cacattctgt aaggtgtaca ccataacccc actgctcagc    840
gacaaccggg agaagcgggg tctcgccctg gatgggaaac tcaagcacga ggacaccaac    900
ctggcttcca gcaccatcgt gaaggagggt gccaacaagg aggtgctggg aatcctggtg    960
tcctacaggg tcaaggtgaa gctggtggtg tctcgaggcg gggatgtctc tgtggagctg    1020 cctttttgttc ttatgcaccc caagccccac gaccacatcc ccctcccccag accccagtca    1080 gccgctccgg agacagatgt ccctgtggac accaacctca ttgaatttga taccaactat    1140
gccacagatg atgacattgt gtttgaggac tttgcccggc ttcggctgaa ggggatgaag    1200
gatgacgact atgatgatca actctgc    1227
```

```
<210> SEQ ID NO 19
<211> LENGTH: 409
<212> TYPE: PRT
<213> ORGANISM: Artificial Sequence
<220> FEATURE:
<223> OTHER INFORMATION: BArr 3F - Beta-arrestin-2
<220> FEATURE:
<221> NAME/KEY: misc_feature
<222> LOCATION: (1)..(409)
<223> OTHER INFORMATION: B-arrestin

<400> SEQUENCE: 19

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
        115                 120                 125
```

-continued

```
Thr Leu Gln Pro Gly Pro Glu Asp Thr Gly Lys Ala Cys Gly Val Asp
    130             135             140

Phe Glu Ile Arg Ala Phe Cys Ala Lys Ser Leu Glu Glu Lys Ser His
145             150             155             160

Lys Arg Asn Ser Val Arg Leu Val Ile Arg Lys Val Gln Phe Ala Pro
            165             170             175

Glu Lys Pro Gly Pro Gln Pro Ser Ala Glu Thr Thr Arg His Phe Leu
            180             185             190

Met Ser Asp Arg Ser Leu His Leu Glu Ala Ser Leu Asp Lys Glu Leu
            195             200             205

Tyr Tyr His Gly Glu Pro Leu Asn Val Asn Val His Val Thr Asn Asn
    210             215             220

Ser Thr Lys Thr Val Lys Lys Ile Lys Val Ser Val Arg Gln Tyr Ala
225             230             235             240

Asp Ile Cys Leu Phe Ser Thr Ala Gln Tyr Lys Cys Pro Val Ala Gln
            245             250             255

Leu Glu Gln Asp Asp Gln Val Ser Pro Ser Ser Thr Phe Cys Lys Val
            260             265             270

Tyr Thr Ile Thr Pro Leu Leu Ser Asp Asn Arg Glu Lys Arg Gly Leu
            275             280             285

Ala Leu Asp Gly Lys Leu Lys His Glu Asp Thr Asn Leu Ala Ser Ser
    290             295             300

Thr Ile Val Lys Glu Gly Ala Asn Lys Glu Val Leu Gly Ile Leu Val
305             310             315             320

Ser Tyr Arg Val Lys Val Lys Leu Val Val Ser Arg Gly Gly Asp Val
            325             330             335

Ser Val Glu Leu Pro Phe Val Leu Met His Pro Lys Pro His Asp His
            340             345             350

Ile Pro Leu Pro Arg Pro Gln Ser Ala Ala Pro Glu Thr Asp Val Pro
            355             360             365

Val Asp Thr Asn Leu Ile Glu Phe Asp Thr Asn Tyr Ala Thr Asp Asp
    370             375             380

Asp Ile Val Phe Glu Asp Phe Ala Arg Leu Arg Leu Lys Gly Met Lys
385             390             395             400

Asp Asp Asp Tyr Asp Asp Gln Leu Cys
                405
```

```
<210> SEQ ID NO 20
<211> LENGTH: 714
<212> TYPE: DNA
<213> ORGANISM: Artificial Sequence
<220> FEATURE:
<223> OTHER INFORMATION: BArr 3F - cpmNeonGreen
<220> FEATURE:
<221> NAME/KEY: misc_feature
<222> LOCATION: (1)..(714)
<223> OTHER INFORMATION: cpmNeonGreen

<400> SEQUENCE: 20
tcgaagaaga cttaccccaa cgacaaaacc atcatcagta cctttaagtg gagttacacc      60
actggaaatg gcaagcgcta ccggagcact gcgcggacca cctacacctt tgccaagcca     120
atggcggcta actatctgaa gaaccagccg atgtacgtgt ccgtaagac ggagctcaag      180 cactccaaga ccgagctcaa cttcaaggag tggcaaaagg cctttaccga tgtgatgggc     240
atggacgagc tgtacaaggg cggtaccgga gggagcatgg tgagcaaggg cgaggaggat     300
aacatggcct ctctcccagc gacacatgag ttacacatct ttggctccat caacggtgtg     360
```

```
gactttgaca tggtgggtca gggcaccggc aatccaaatg atggttatga ggagttaaac    420
ctgaagtcca ccaagggtga cctccagttc tcccccctgga ttctggtccc tcatatcggg    480
tatggcttcc atcagtacct gccctaccct gacgggatgt cgcctttcca ggccgccatg    540
gtagatggct ccggatacca agtccatcgc acaatgcagt ttgaagatgg tgcctccctt    600
actgttaact accgctacac ctacgaggga agccacatca aaggagaggc ccaggtgaag    660
gggactggtt tccctgctga cggtcctgtg atgaccaact cgctgaccgc tgcg          714
```

<210> SEQ ID NO 21
<211> LENGTH: 238
<212> TYPE: PRT
<213> ORGANISM: Artificial Sequence
<220> FEATURE:
<223> OTHER INFORMATION: BArr 3F - cpmNeonGreen
<220> FEATURE:
<221> NAME/KEY: misc_feature
<222> LOCATION: (1)..(238)
<223> OTHER INFORMATION: cpmNeonGreen

<400> SEQUENCE: 21

Ser Lys Lys Thr Tyr Pro Asn Asp Lys Thr Ile Ile Ser Thr Phe Lys
1               5                   10                  15

Trp Ser Tyr Thr Thr Gly Asn Gly Lys Arg Tyr Arg Ser Thr Ala Arg
            20                  25                  30

Thr Thr Tyr Thr Phe Ala Lys Pro Met Ala Ala Asn Tyr Leu Lys Asn
        35                  40                  45

Gln Pro Met Tyr Val Phe Arg Lys Thr Glu Leu Lys His Ser Lys Thr
    50                  55                  60

Glu Leu Asn Phe Lys Glu Trp Gln Lys Ala Phe Thr Asp Val Met Gly
65                  70                  75                  80

Met Asp Glu Leu Tyr Lys Gly Gly Thr Gly Gly Ser Met Val Ser Lys
                85                  90                  95

Gly Glu Glu Asp Asn Met Ala Ser Leu Pro Ala Thr His Glu Leu His
            100                 105                 110

Ile Phe Gly Ser Ile Asn Gly Val Asp Phe Asp Met Val Gly Gln Gly
        115                 120                 125

Thr Gly Asn Pro Asn Asp Gly Tyr Glu Glu Leu Asn Leu Lys Ser Thr
    130                 135                 140

Lys Gly Asp Leu Gln Phe Ser Pro Trp Ile Leu Val Pro His Ile Gly
145                 150                 155                 160

Tyr Gly Phe His Gln Tyr Leu Pro Tyr Pro Asp Gly Met Ser Pro Phe
                165                 170                 175

Gln Ala Ala Met Val Asp Gly Ser Gly Tyr Gln Val His Arg Thr Met
            180                 185                 190

Gln Phe Glu Asp Gly Ala Ser Leu Thr Val Asn Tyr Arg Tyr Thr Tyr
        195                 200                 205

Glu Gly Ser His Ile Lys Gly Glu Ala Gln Val Lys Gly Thr Gly Phe
    210                 215                 220

Pro Ala Asp Gly Pro Val Met Thr Asn Ser Leu Thr Ala Ala
225                 230                 235

<210> SEQ ID NO 22
<211> LENGTH: 7079
<212> TYPE: DNA
<213> ORGANISM: Artificial Sequence
<220> FEATURE:
<223> OTHER INFORMATION: BArr 4A plasmid -continued

```
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (321)..(904)
<223> OTHER INFORMATION: CMV promoter
<220> FEATURE:
<221> NAME/KEY: misc_feature
<222> LOCATION: (1039)..(1864)
<223> OTHER INFORMATION: CMV intron
<220> FEATURE:
<221> NAME/KEY: misc_feature
<222> LOCATION: (1936)..(2385)
<223> OTHER INFORMATION: mNeonGreen
<220> FEATURE:
<221> NAME/KEY: misc_feature
<222> LOCATION: (2191)..(2200)
<223> OTHER INFORMATION: Kozak sequence
<220> FEATURE:
<221> NAME/KEY: misc_feature
<222> LOCATION: (2386)..(3609)
<223> OTHER INFORMATION: B-arrestin
<220> FEATURE:
<221> NAME/KEY: misc_feature
<222> LOCATION: (2386)..(2388)
<223> OTHER INFORMATION: Met to Gly mutation
<220> FEATURE:
<221> NAME/KEY: misc_feature
<222> LOCATION: (3610)..(3870)
<223> OTHER INFORMATION: mNeonGreen
<220> FEATURE:
<221> NAME/KEY: misc_feature
<222> LOCATION: (4009)..(4233)
<223> OTHER INFORMATION: bGH poly(A) signal
<220> FEATURE:
<221> NAME/KEY: misc_feature
<222> LOCATION: (4828)..(5416)
<223> OTHER INFORMATION: ori
<220> FEATURE:
<221> NAME/KEY: misc_feature
<222> LOCATION: (5959)..(6774)
<223> OTHER INFORMATION: KanR

<400> SEQUENCE: 22
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgaaatac cgcacagatg cgtaaggaga aaataccgca tcagattggc      240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
```

-continued

```
agaagacacc gggaccgatc cagcctccgc ggccgggaac ggtgcattgg aacgcggatt      1020
ccccgtgcca agagtgacgt aagtaccgcc tatagactct ataggcacac ccctttggct      1080
cttatgcatg ctatactgtt tttggcttgg ggcctataca cccccgcttc cttatgctat      1140
aggtgatggt atagcttagc ctataggtgt gggttattga ccattattga ccactcccct      1200
attggtgacg atactttcca ttactaatcc ataacatggc tctttgccac aactatctct      1260
attggctata tgccaatact ctgtccttca gagactgaca cggactctgt atttttacag      1320
gatggggtcc catttattat ttacaaattc acatatacaa caacgccgtc ccccgtgccc      1380
gcagttttta ttaaacatag cgtgggatct ccacgcgaat ctcgggtacg tgttccggac      1440
atgggctctt ctccggtagc ggcggagctt ccacatccga gccctggtcc catgcctcca      1500
gcggctcatg gtcgctcggc agctccttgc tcctaacagt ggaggccaga cttaggcaca      1560
gcacaatgcc caccaccacc agtgtgccgc acaaggccgt ggcggtaggg tatgtgtctg      1620
aaaatgagcg tggagattgg gctcgcacgg ctgacgcaga tggaagactt aaggcagcgg      1680
cagaagaaga tgcaggcagc tgagttgttg tattctgata agagtcagag gtaactcccg      1740
ttgcggtgct gttaacggtg gagggcagtg tagtctgagc agtactcgtt gctgccgcgc      1800
gcgccaccag acataatagc tgacagacta acagactgtt cctttccatg ggtcttttct      1860
gcagtcaccg tcgtcgacac gtgtgatcag atatacgact cactataggg agacccaagc      1920
tggctagcgt ttaccatggt gagcaagggc gaggaggata acatggcctc tctcccagcg      1980
acacatgagt tacacatctt tggctccatc aacggtgtgg actttgacat ggtgggtcag      2040
ggcaccggca atccaaatga tggttatgag gagttaaacc tgaagtccac caagggtgac      2100
ctccagttct cccctggat tctggtccct catatcgggt atggcttcca tcagtacctg      2160
ccctaccctg acgggatgtc gcctttccag gccgccatgg tagatggctc cggataccaa      2220
gtccatcgca caatgcagtt tgaagatggt gcctccctta ctgttaacta ccgctacacc      2280
tacgagggaa gccacatcaa aggagaggcc caggtgaagg ggactggttt ccctgctgac      2340
ggtcctgtga tgaccaactc gctgaccgct gcggactggt gcagggggga gaaacccggg      2400 accaggggtct tcaagaagtc gagccctaac tgcaagctca ccgtgtactt gggcaagcgg      2460
gacttcgtag atcacctgga caaagtggac cctgtagatg gcgtggtgct tgtggaccct      2520
gactacctga aggaccgcaa agtgtttgtg accctcacct gcgccttccg ctatggccgt      2580
gaagacctgg atgtgctggg cttgtccttc gcaaagacc tgttcatcgc cacctaccag      2640
gccttccccc cggtgcccaa cccaccccgg ccccccaccc gcctgcagga ccggctgctg      2700
aggaagctgg gccagcatgc ccacccttc ttcttcacca taccccagaa tcttccatgc      2760
tccgtcacac tgcagccagg cccagaggat acaggaaagg cctgcggcgt agactttgag      2820
attcgagcct tctgtgctaa atcactagaa gagaaaagcc acaaaaggaa ctctgtgcgg      2880
ctggtgatcc gaaaggtgca gttcgccccg gagaaacccg gccccagcc ttcagccgaa      2940 accacacgcc acttcctcat gtctgaccgg tccctgcacc tcgaggcttc cctggacaag      3000
gagctgtact accatgggga gcccctcaat gtaaatgtcc acgtcaccaa caactccacc      3060
aagaccgtca agaagatcaa agtctctgtg agacagtacg ccgacatctg cctcttcagc      3120
accgcccagt acaagtgtcc tgtggctcaa ctcgaacaag atgaccaggt atctcccagc      3180
tccacattct gtaaggtgta caccataacc ccactgctca gcgacaaccg ggagaagcgg      3240
ggtctcgccc tggatgggaa actcaagcac gaggacacca acctggcttc cagcaccatc      3300
gtgaaggagg gtgccaacaa ggaggtgctg ggaatcctgg tgtcctacag ggtcaaggtg      3360
```

```
aagctggtgg tgtctcgagg cggggatgtc tctgtggagc tgcctttgt tcttatgcac      3420 cccaagcccc acgaccacat cccctcccc agaccccagt cagccgctcc ggagacagat      3480
gtccctgtgg acaccaacct cattgaattt gataccaact atgccacaga tgatgacatt      3540
gtgtttgagg actttgcccg gcttcggctg aaggggatga aggatgacga ctatgatgat      3600
caactctgct cgaagaagac ttaccccaac gacaaaacca tcatcagtac ctttaagtgg      3660
agttacacca ctggaaatgg caagcgctac cggagcactg cgcggaccac ctacaccttt      3720
gccaagccaa tggcggctaa ctatctgaag aaccagccga tgtacgtgtt ccgtaagacg      3780
gagctcaagc actccaagac cgagctcaac ttcaaggagt ggcaaaaggc ctttaccgat      3840
gtgatgggca tggacgagct gtacaagtag cgcgccctcg actgtgcctt ctagttgcca      3900
gccatctgta tcgcggccgc tctagaccag gcgcctggat ccagatcact tctggctaat      3960
aaaagatcag agctctagag atctgtgtgt tggtttttttg tggatctgct gtgccttcta      4020
gttgccagcc atctgttgtt tgcccctccc ccgtgccttc cttgaccctg gaaggtgcca      4080
ctcccactgt cctttcctaa taaaatgagg aaattgcatc gcattgtctg agtaggtgtc      4140
attctattct ggggggtggg gtggggcagc acagcaaggg ggaggattgg gaagacaata      4200
gcaggcatgc tggggatgcg gtgggctcta tgggtacctc tctctctctc tctctctctc      4260
tctctctctc tctctctcgg tacctctctc tctctctctc tctctctctc tctctctctc      4320
tctcggtacc aggtgctgaa gaattgaccc ggttcctcct gggccagaaa gaagcaggca      4380
catccccttc tctgtgacac accctgtcca cgccctggt tcttagttcc agccccactc      4440
ataggacact catagctcag gagggctccg ccttcaatcc cacccgctaa agtacttgga      4500
gcggtctctc cctccctcat cagcccacca aaccaaacct agcctccaag agtgggaaga      4560
aattaaagca agataggcta ttaagtgcag agggagagaa aatgcctcca acatgtgagg      4620
aagtaatgag agaaatcata gaatttcttc cgcttcctcg ctcactgact cgctgcgctc      4680
ggtcgttcgg ctgcggcgag cggtatcagc tcactcaaag gcggtaatac ggttatccac      4740
agaatcaggg gataacgcag gaaagaacat gtgagcaaaa ggccagcaaa aggccaggaa      4800
ccgtaaaaag gccgcgttgc tggcgttttt ccataggctc cgcccccctg acgagcatca      4860
caaaaatcga cgctcaagtc agaggtggcg aaacccgaca ggactataaa gataccaggc      4920
gtttccccct ggaagctccc tcgtgcgctc tcctgttccg accctgccgc ttaccggata      4980
cctgtccgcc tttctccctt cgggaagcgt ggcgctttct caatgctcac gctgtaggta      5040
tctcagttcg gtgtaggtcg ttcgctccaa gctgggctgt gtgcacgaac cccccgttca      5100
gcccgaccgc tgcgccttat ccggtaacta tcgtcttgag tccaacccgg taagacacga      5160
cttatcgcca ctggcagcag ccactggtaa caggattagc agagcgaggt atgtaggcgg      5220
tgctacagag ttcttgaagt ggtggcctaa ctacggctac actagaagga cagtatttgg      5280
tatctgcgct ctgctgaagc cagttacctt cggaaaaaga gttggtagct cttgatccgg      5340
caaacaaacc accgctggta gcggtggttt ttttgtttgc aagcagcaga ttacgcgcag      5400
aaaaaaagga tctcaagaag atcctttgat cttttctacg gggtctgacg ctcagtggaa      5460
cgaaaactca cgttaaggga ttttggtcat gagattatca aaaaggatct tcacctagat      5520
ccttttaaat taaaaatgaa gttttaaatc aatctaaagt atatatgagt aaacttggtc      5580
tgacagttac caatgcttaa tcagtgaggc acctatctca gcgatctgtc tatttcgttc      5640
atccatagtt gcctgactcc ggggggggg ggcgctgagg tctgcctcgt gaagaaggtg      5700
```

-continued

```
ttgctgactc ataccaggcc tgaatcgccc catcatccag ccagaaagtg agggagccac    5760
ggttgatgag agctttgttg taggtggacc agttggtgat tttgaacttt tgctttgcca    5820
cggaacggtc tgcgttgtcg ggaagatgcg tgatctgatc cttcaactca gcaaaagttc    5880
gatttattca acaaagccgc cgtcccgtca agtcagcgta atgctctgcc agtgttacaa    5940
ccaattaacc aattctgatt agaaaaactc atcgagcatc aaatgaaact gcaatttatt    6000
catatcagga ttatcaatac catatttttg aaaaagccgt ttctgtaatg aaggagaaaa    6060
ctcaccgagg cagttccata ggatggcaag atcctggtat cggtctgcga ttccgactcg    6120
tccaacatca atacaaccta ttaatttccc ctcgtcaaaa ataaggttat caagtgagaa    6180
atcaccatga gtgacgactg aatccggtga gaatggcaaa agcttatgca tttctttcca    6240
gacttgttca acaggccagc cattacgctc gtcatcaaaa tcactcgcat caaccaaacc    6300
gttattcatt cgtgattgcg cctgagcgag acgaaatacg cgatcgctgt taaaaggaca    6360
attacaaaca ggaatcgaat gcaaccggcg caggaacact gccagcgcat caacaatatt    6420
ttcacctgaa tcaggatatt cttctaatac ctggaatgct gttttcccgg ggatcgcagt    6480
ggtgagtaac catgcatcat caggagtacg ataaaatgc ttgatggtcg gaagaggcat    6540
aaattccgtc agccagttta gtctgaccat ctcatctgta acatcattgg caacgctacc    6600
tttgccatgt ttcagaaaca actctggcgc atcgggcttc ccatacaatc gatagattgt    6660
cgcacctgat tgcccgacat tatcgcgagc ccatttatac ccatataaat cagcatccat    6720
gttggaattt aatcgcggcc tcgagcaaga cgtttcccgt tgaatatggc tcataacacc    6780
ccttgtatta ctgtttatgt aagcagacag ttttattgtt catgatgata tattttttatc    6840 ttgtgcaatg taacatcaga gattttgaga cacaacgtgg ctttccccc cccccccatta    6900 ttgaagcatt tatcagggtt attgtctcat gagcggatac atatttgaat gtatttagaa    6960
aaataaacaa ataggggttc cgcgcacatt tccccgaaaa gtgccacctg acgtctaaga    7020
aaccattatt atcatgacat taacctataa aaataggcgt atcacgaggc cctttcgtc      7079
```

```
<210> SEQ ID NO 23
<211> LENGTH: 7079
<212> TYPE: DNA
<213> ORGANISM: Artificial Sequence
<220> FEATURE:
<223> OTHER INFORMATION: BArr 4A coding sequence
<220> FEATURE:
<221> NAME/KEY: misc_feature
<222> LOCATION: (1)..(450)
<223> OTHER INFORMATION: mNeonGreen
<220> FEATURE:
<221> NAME/KEY: misc_feature
<222> LOCATION: (451)..(1674)
<223> OTHER INFORMATION: B-Arrestin
<220> FEATURE:
<221> NAME/KEY: misc_feature
<222> LOCATION: (451)..(453)
<223> OTHER INFORMATION: Met to Gly mutation
<220> FEATURE:
<221> NAME/KEY: misc_feature
<222> LOCATION: (1675)..(1935)
<223> OTHER INFORMATION: mNeonGreen

<400> SEQUENCE: 23
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accatatgcg ggtgaaatac cgcacagatg cgtaaggaga aaataccgca tcagattggc      240
```

-continued

```
tattggccat tgcatacgtt gtatccatat cataatatgt acatttatat tggctcatgt        300
ccaacattac cgccatgttg acattgatta ttgactagtt attaatagta atcaattacg        360
gggtcattag ttcatagccc atatatggag ttccgcgtta cataacttac ggtaaatggc        420
ccgcctggct gaccgcccaa cgaccccgc ccattgacgt caataatgac gtatgttccc         480
atagtaacgc caatagggac tttccattga cgtcaatggg tggagtattt acggtaaact        540
gcccacttgg cagtacatca agtgtatcat atgccaagta cgcccctat tgacgtcaat         600 gacggtaaat ggcccgcctg gcattatgcc cagtacatga ccttatggga ctttcctact        660
tggcagtaca tctacgtatt agtcatcgct attaccatgg tgatgcggtt ttggcagtac        720
atcaatgggc gtggatagcg gtttgactca cggggatttc caagtctcca ccccattgac        780
gtcaatggga gtttgttttg gcaccaaaat caacgggact ttccaaaatg tcgtaacaac        840
tccgccccat tgacgcaaat gggcggtagg cgtgtacggt gggaggtcta tataagcaga        900
gctcgtttag tgaaccgtca gatcgcctgg agacgccatc cacgctgttt tgacctccat        960
agaagacacc gggaccgatc cagcctccgc ggccgggaac ggtgcattgg aacgcggatt       1020
ccccgtgcca agagtgacgt aagtaccgcc tatagactct ataggcacac ccctttggct       1080
cttatgcatg ctatactgtt tttggcttgg ggcctataca cccccgcttc cttatgctat       1140
aggtgatggt atagcttagc ctataggtgt gggttattga ccattattga ccactcccct       1200
attggtgacg atactttcca ttactaatcc ataacatggc tctttgccac aactatctct       1260
attggctata tgccaatact ctgtccttca gagactgaca cggactctgt attttttacag      1320 gatggggtcc catttattat ttacaaattc acatatacaa caacgccgtc ccccgtgccc       1380
gcagttttta ttaaacatag cgtgggatct ccacgcgaat ctcgggtacg tgttccggac       1440
atgggctctt ctccggtagc ggcggagctt ccacatccga gccctggtcc catgcctcca       1500
gcggctcatg gtcgctcggc agctccttgc tcctaacagt ggaggccaga cttaggcaca       1560
gcacaatgcc caccaccacc agtgtgccgc acaaggccgt ggcggtaggg tatgtgtctg       1620
aaaatgagcg tggagattgg gctcgcacgg ctgacgcaga tggaagactt aaggcagcgg       1680
cagaagaaga tgcaggcagc tgagttgttg tattctgata agagtcagag gtaactcccg       1740
ttgcggtgct gttaacggtg gagggcagtg tagtctgagc agtactcgtt gctgccgcgc       1800
gcgccaccag acataatagc tgacagacta acagactgtt cctttccatg ggtcttttct       1860
gcagtcaccg tcgtcgacac gtgtgatcag atatacgact cactataggg agacccaagc       1920
tggctagcgt ttaccatggt gagcaagggc gaggaggata acatggcctc tctcccagcg       1980
acacatgagt tacacatctt tggctccatc aacggtgtgg actttgacat ggtgggtcag      2040
ggcaccggca atccaaatga tggttatgag gagttaaacc tgaagtccac caagggtgac      2100
ctccagttct cccctggat tctggtccct catatcgggt atggcttcca tcagtacctg       2160
ccctaccctg acgggatgtc gcctttccag gccgccatgg tagatggctc cggataccaa      2220
gtccatcgca caatgcagtt tgaagatggt gcctccctta ctgttaacta ccgctacacc      2280
tacgagggaa gccacatcaa aggagaggcc caggtgaagg ggactggttt ccctgctgac      2340
ggtcctgtga tgaccaactc gctgaccgct gcggactggg caggggggga aaacccgggg      2400
accagggtct tcaagaagtc gagccctaac tgcaagctca ccgtgtactt gggcaagcgg      2460
gacttcgtag atcacctgga caaagtggac cctgtagatg cgtggtgct tgtggaccct      2520 gactacctga aggaccgcaa agtgtttgtg accctcacct gcgccttccg ctatggccgt      2580
```

-continued

```
gaagacctgg atgtgctggg cttgtccttc cgcaaagacc tgttcatcgc cacctaccag   2640
gccttccccc cggtgcccaa cccaccccgg cccccacccc gcctgcagga ccggctgctg   2700
aggaagctgg gccagcatgc ccaccccttc ttcttcacca taccccagaa tcttccatgc   2760
tccgtcacac tgcagccagg cccagaggat acaggaaagg cctgcggcgt agactttgag   2820
attcgagcct tctgtgctaa atcactagaa gagaaaagcc acaaaaggaa ctctgtgcgg   2880
ctggtgatcc gaaaggtgca gttcgccccg gagaaacccg gccccagcc ttcagccgaa   2940 accacacgcc acttcctcat gtctgaccgg tccctgcacc tcgaggcttc cctggacaag   3000
gagctgtact accatgggga gcccctcaat gtaaatgtcc acgtcaccaa caactccacc   3060
aagaccgtca agaagatcaa agtctctgtg agacagtacg ccgacatctg cctcttcagc   3120
accgcccagt acaagtgtcc tgtggctcaa ctcgaacaag atgaccaggt atctcccagc   3180
tccacattct gtaaggtgta caccataacc ccactgctca gcgacaaccg ggagaagcgg   3240
ggtctcgccc tggatgggaa actcaagcac gaggacacca acctggcttc cagcaccatc   3300
gtgaaggagg gtgccaacaa ggaggtgctg ggaatcctgg tgtcctacag ggtcaaggtg   3360
aagctggtgg tgtctcgagg cggggatgtc tctgtggagc tgccttttgt tcttatgcac   3420
cccaagcccc acgaccacat cccccctcccc agaccccagt cagccgctcc ggagacagat   3480
gtccctgtgg acaccaacct cattgaattt gataccaact atgccacaga tgatgacatt   3540
gtgtttgagg actttgcccg gcttcggctg aaggggatga aggatgacga ctatgatgat   3600
caactctgct cgaagaagac ttaccccaac gacaaaacca tcatcagtac ctttaagtgg   3660
agttacacca ctggaaatgg caagcgctac cggagcactg cgcggaccac ctacaccttt   3720
gccaagccaa tggcggctaa ctatctgaag aaccagccga tgtacgtgtt ccgtaagacg   3780
gagctcaagc actccaagac cgagctcaac ttcaaggagt ggcaaaaggc ctttaccgat   3840
gtgatgggca tggacgagct gtacaagtag cgcgccctcg actgtgcctt ctagttgcca   3900
gccatctgta tcgcggccgc tctagaccag gcgcctggat ccagatcact tctggctaat   3960
aaaagatcag agctctagag atctgtgtgt tggttttttg tggatctgct gtgccttcta   4020
gttgccagcc atctgttgtt tgcccctccc ccgtgccttc cttgaccctg gaaggtgcca   4080
ctcccactgt cctttcctaa taaaatgagg aaattgcatc gcattgtctg agtaggtgtc   4140
attctattct ggggggtggg gtggggcagc acagcaaggg ggaggattgg gaagacaata   4200
gcaggcatgc tggggatgcg gtgggctcta tgggtacctc tctctctctc tctctctctc   4260
tctctctctc tctctctcgg tacctctctc tctctctctc tctctctctc tctctctctc   4320
tctcggtacc aggtgctgaa gaattgaccc ggttcctcct gggccagaaa gaagcaggca   4380
catccccttc tctgtgacac accctgtcca cgcccctggt tcttagttcc agccccactc   4440
ataggacact catagctcag gagggctccg ccttcaatcc cacccgctaa agtacttgga   4500
gcggtctctc cctccctcat cagcccacca aaccaaacct agcctccaag agtgggaaga   4560
aattaaagca agataggcta ttaagtgcag agggagagaa aatgcctcca acatgtgagg   4620
aagtaatgag agaaatcata gaatttcttc cgcttcctcg ctcactgact cgctgcgctc   4680
ggtcgttcgc ctgcggcgag cggtatcagc tcactcaaag gcggtaatac ggttatccac   4740
agaatcaggg gataacgcag gaaagaacat gtgagcaaaa ggccagcaaa aggccaggaa   4800
ccgtaaaaag gccgcgttgc tggcgttttt ccataggctc cgcccccctg acgagcatca   4860
caaaaatcga cgctcaagtc agaggtggcg aaacccgaca ggactataaa gataccaggc   4920
gtttccccct ggaagctccc tcgtgcgctc tcctgttccg accctgccgc ttaccggata   4980
```

```
cctgtccgcc tttctccctt cgggaagcgt ggcgcttct caatgctcac gctgtaggta      5040
tctcagttcg gtgtaggtcg ttcgctccaa gctgggctgt gtgcacgaac cccccgttca      5100
gcccgaccgc tgcgccttat ccggtaacta tcgtcttgag tccaacccgg taagacacga      5160
cttatcgcca ctggcagcag ccactggtaa caggattagc agagcgaggt atgtaggcgg      5220
tgctacagag ttcttgaagt ggtggcctaa ctacggctac actagaagga cagtatttgg      5280
tatctgcgct ctgctgaagc cagttacctt cggaaaaaga gttggtagct cttgatccgg      5340
caaacaaacc accgctggta gcggtggttt ttttgtttgc aagcagcaga ttacgcgcag      5400
aaaaaaagga tctcaagaag atcctttgat cttttctacg gggtctgacg ctcagtggaa      5460
cgaaaactca cgttaaggga ttttggtcat gagattatca aaaaggatct tcacctagat      5520
ccttttaaat taaaaatgaa gttttaaatc aatctaaagt atatatgagt aaacttggtc      5580
tgacagttac caatgcttaa tcagtgaggc acctatctca gcgatctgtc tatttcgttc      5640
atccatagtt gcctgactcc ggggggggggg ggcgctgagg tctgcctcgt gaagaaggtg      5700
ttgctgactc ataccaggcc tgaatcgccc catcatccag ccagaaagtg agggagccac      5760
ggttgatgag agctttgttg taggtggacc agttggtgat tttgaacttt tgctttgcca      5820
cggaacggtc tgcgttgtcg ggaagatgcg tgatctgatc cttcaactca gcaaaagttc      5880
gatttattca acaaagccgc cgtcccgtca agtcagcgta atgctctgcc agtgttacaa      5940
ccaattaacc aattctgatt agaaaaactc atcgagcatc aaatgaaact gcaatttatt      6000
catatcagga ttatcaatac catattttg aaaaagccgt ttctgtaatg aaggagaaaa      6060
ctcaccgagg cagttccata ggatggcaag atcctggtat cggtctgcga ttccgactcg      6120
tccaacatca atacaaccta ttaatttccc ctcgtcaaaa ataaggttat caagtgagaa      6180
atcaccatga gtgacgactg aatccggtga gaatggcaaa agcttatgca tttctttcca      6240
gacttgttca acaggccagc cattacgctc gtcatcaaaa tcactcgcat caaccaaacc      6300
gttattcatt cgtgattgcg cctgagcgag acgaaatacg cgatcgctgt taaaaggaca      6360
attacaaaca ggaatcgaat gcaaccggcg caggaacact gccagcgcat caacaatatt      6420
ttcacctgaa tcaggatatt cttctaatac ctggaatgct gttttcccgg ggatcgcagt      6480
ggtgagtaac catgcatcat caggagtacg ataaaatgc ttgatggtcg aagaggcat      6540 aaattccgtc agccagttta gtctgaccat ctcatctgta acatcattgg caacgctacc      6600
tttgccatgt ttcagaaaca actctggcgc atcgggcttc ccatacaatc gatagattgt      6660
cgcacctgat tgcccgacat tatcgcgagc ccatttatac ccatataaat cagcatccat      6720
gttggaattt aatcgcggcc tcgagcaaga cgtttcccgt tgaatatggc tcataacacc      6780
ccttgtatta ctgtttatgt aagcagacag ttttattgtt catgatgata tattttatc      6840 ttgtgcaatg taacatcaga gattttgaga cacaacgtgg ctttccccc cccccatta      6900 ttgaagcatt tatcagggtt attgtctcat gagcggatac atatttgaat gtatttagaa      6960
aaataaacaa ataggggttc cgcgcacatt tccccgaaaa gtgccacctg acgtctaaga      7020
aaccattatt atcatgacat taacctataa aaataggcgt atcacgaggc cctttcgtc      7079
```

<210> SEQ ID NO 24
<211> LENGTH: 644
<212> TYPE: PRT
<213> ORGANISM: Artificial Sequence
<220> FEATURE:
<223> OTHER INFORMATION: BArr 4A coding sequence
<220> FEATURE:

-continued

```
<221> NAME/KEY: SITE
<222> LOCATION: (1)..(150)
<223> OTHER INFORMATION: mNeonGreen
<220> FEATURE:
<221> NAME/KEY: SITE
<222> LOCATION: (151)..(558)
<223> OTHER INFORMATION: B-arrestin
<220> FEATURE:
<221> NAME/KEY: SITE
<222> LOCATION: (151)..(151)
<223> OTHER INFORMATION: Met to Gly mutation
<220> FEATURE:
<221> NAME/KEY: SITE
<222> LOCATION: (559)..(644)
<223> OTHER INFORMATION: mNeonGreen

<400> SEQUENCE: 24

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
                20                  25                  30

Val Gly Gln Gly Thr Gly Asn Pro Asn Asp Gly Tyr Glu Glu Leu Asn
            35                  40                  45

Leu Lys Ser Thr Lys Gly Asp Leu Gln Phe Ser Pro Trp Ile Leu Val
        50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
        130                 135                 140

Ala Ala Asp Trp Cys Arg Gly Glu Lys Pro Gly Thr Arg Val Phe Lys
145                 150                 155                 160

Lys Ser Ser Pro Asn Cys Lys Leu Thr Val Tyr Leu Gly Lys Arg Asp
                165                 170                 175

Phe Val Asp His Leu Asp Lys Val Asp Pro Val Asp Gly Val Val Leu
            180                 185                 190

Val Asp Pro Asp Tyr Leu Lys Asp Arg Lys Val Phe Val Thr Leu Thr
        195                 200                 205

Cys Ala Phe Arg Tyr Gly Arg Glu Asp Leu Asp Val Leu Gly Leu Ser
    210                 215                 220

Phe Arg Lys Asp Leu Phe Ile Ala Thr Tyr Gln Ala Phe Pro Pro Val
225                 230                 235                 240

Pro Asn Pro Pro Arg Pro Pro Thr Arg Leu Gln Asp Arg Leu Leu Arg
                245                 250                 255

Lys Leu Gly Gln His Ala His Pro Phe Phe Phe Thr Ile Pro Gln Asn
            260                 265                 270

Leu Pro Cys Ser Val Thr Leu Gln Pro Gly Pro Glu Asp Thr Gly Lys
            275                 280                 285

Ala Cys Gly Val Asp Phe Glu Ile Arg Ala Phe Cys Ala Lys Ser Leu
        290                 295                 300

Glu Glu Lys Ser His Lys Arg Asn Ser Val Arg Leu Val Ile Arg Lys
305                 310                 315                 320

Val Gln Phe Ala Pro Glu Lys Pro Gly Pro Gln Pro Ser Ala Glu Thr
```

-continued

```
                     325                 330                 335

Thr Arg His Phe Leu Met Ser Asp Arg Ser Leu His Leu Glu Ala Ser
            340                 345                 350

Leu Asp Lys Glu Leu Tyr Tyr His Gly Glu Pro Leu Asn Val Asn Val
            355                 360                 365

His Val Thr Asn Asn Ser Thr Lys Thr Val Lys Lys Ile Lys Val Ser
370                 375                 380

Val Arg Gln Tyr Ala Asp Ile Cys Leu Phe Ser Thr Ala Gln Tyr Lys
385                 390                 395                 400

Cys Pro Val Ala Gln Leu Glu Gln Asp Asp Gln Val Ser Pro Ser Ser
                405                 410                 415

Thr Phe Cys Lys Val Tyr Thr Ile Thr Pro Leu Leu Ser Asp Asn Arg
            420                 425                 430

Glu Lys Arg Gly Leu Ala Leu Asp Gly Lys Leu Lys His Glu Asp Thr
            435                 440                 445

Asn Leu Ala Ser Ser Thr Ile Val Lys Glu Gly Ala Asn Lys Glu Val
450                 455                 460

Leu Gly Ile Leu Val Ser Tyr Arg Val Lys Val Lys Leu Val Val Ser
465                 470                 475                 480

Arg Gly Gly Asp Val Ser Val Glu Leu Pro Phe Val Leu Met His Pro
                485                 490                 495

Lys Pro His Asp His Ile Pro Leu Pro Arg Pro Gln Ser Ala Ala Pro
                500                 505                 510

Glu Thr Asp Val Pro Val Asp Thr Asn Leu Ile Glu Phe Asp Thr Asn
            515                 520                 525

Tyr Ala Thr Asp Asp Asp Ile Val Phe Glu Asp Phe Ala Arg Leu Arg
            530                 535                 540

Leu Lys Gly Met Lys Asp Asp Asp Tyr Asp Asp Gln Leu Cys Ser Lys
545                 550                 555                 560

Lys Thr Tyr Pro Asn Asp Lys Thr Ile Ile Ser Thr Phe Lys Trp Ser
                565                 570                 575

Tyr Thr Thr Gly Asn Gly Lys Arg Tyr Arg Ser Thr Ala Arg Thr Thr
                580                 585                 590

Tyr Thr Phe Ala Lys Pro Met Ala Ala Asn Tyr Leu Lys Asn Gln Pro
            595                 600                 605

Met Tyr Val Phe Arg Lys Thr Glu Leu Lys His Ser Lys Thr Glu Leu
            610                 615                 620

Asn Phe Lys Glu Trp Gln Lys Ala Phe Thr Asp Val Met Gly Met Asp
625                 630                 635                 640

Glu Leu Tyr Lys
```

```
<210> SEQ ID NO 25
<211> LENGTH: 450
<212> TYPE: DNA
<213> ORGANISM: Artificial Sequence
<220> FEATURE:
<223> OTHER INFORMATION: BArr 4A mNeonGreen Part 1
<220> FEATURE:
<221> NAME/KEY: misc_feature
<222> LOCATION: (1)..(450)
<223> OTHER INFORMATION: mNeonGreen
<220> FEATURE:
<221> NAME/KEY: misc_feature
<222> LOCATION: (256)..(265)
<223> OTHER INFORMATION: Kozak sequence

<400> SEQUENCE: 25
```

-continued

```
atggtgagca agggcgagga ggataacatg gcctctctcc cagcgacaca tgagttacac     60
atctttggct ccatcaacgg tgtggacttt gacatggtgg gtcagggcac cggcaatcca    120
aatgatggtt atgaggagtt aaacctgaag tccaccaagg gtgacctcca gttctccccc    180
tggattctgg tccctcatat cgggtatggc ttccatcagt acctgcccta ccctgacggg    240
atgtcgcctt ccaggccgc catggtagat ggctccggat accaagtcca tcgcacaatg     300
cagtttgaag atggtgcctc ccttactgtt aactaccgct acacctacga gggaagccac    360
atcaaaggag aggcccaggt gaaggggact ggtttccctg ctgacggtcc tgtgatgacc    420
aactcgctga ccgctgcgga ctggtgcagg                                     450
```

<210> SEQ ID NO 26
<211> LENGTH: 150
<212> TYPE: PRT
<213> ORGANISM: Artificial Sequence
<220> FEATURE:
<223> OTHER INFORMATION: BArr 4A - mNeonGreen Part 1
<220> FEATURE:
<221> NAME/KEY: SITE
<222> LOCATION: (1)..(150)
<223> OTHER INFORMATION: mNeonGreen Part 1

<400> SEQUENCE: 26

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg
145                 150
```

<210> SEQ ID NO 27
<211> LENGTH: 1224
<212> TYPE: DNA
<213> ORGANISM: Artificial Sequence
<220> FEATURE:
<223> OTHER INFORMATION: BArr 4A Beta-arrestin-2
<220> FEATURE:
<221> NAME/KEY: misc_feature
<222> LOCATION: (1)..(1224)
<223> OTHER INFORMATION: B-arrestin

<400> SEQUENCE: 27

```
ggggagaaac ccgggaccag ggtcttcaag aagtcgagcc ctaactgcaa gctcaccgtg     60
tacttgggca agcgggactt cgtagatcac ctggacaaag tggaccctgt agatggcgtg    120
gtgcttgtgg accctgacta cctgaaggac cgcaaagtgt ttgtgaccct cacctgcgcc    180
```

```
ttccgctatg gccgtgaaga cctggatgtg ctgggcttgt ccttccgcaa agacctgttc      240
atcgccacct accaggcctt cccccccggtg cccaacccac cccggccccc cacccgcctg      300
caggaccggc tgctgaggaa gctgggccag catgcccacc ccttcttctt caccatacccc     360 cagaatcttc catgctccgt cacactgcag ccaggcccag aggatacagg aaaggcctgc      420
ggcgtagact ttgagattcg agccttctgt gctaaatcac tagaagagaa aagccacaaa      480
aggaactctg tgcggctggt gatccgaaag gtgcagttcg ccccggagaa acccggcccc      540
cagccttcag ccgaaaccac acgccacttc ctcatgtctg accggtccct gcacctcgag      600
gcttccctgg acaaggagct gtactaccat ggggagcccc tcaatgtaaa tgtccacgtc      660
accaacaact ccaccaagac cgtcaagaag atcaaagtct ctgtgagaca gtacgccgac      720
atctgcctct tcagcaccgc ccagtacaag tgtcctgtgg ctcaactcga acaagatgac      780
caggtatctc ccagctccac attctgtaag gtgtacacca taaccccact gctcagcgac      840
aaccgggaga agcggggtct cgccctggat gggaaactca agcacgagga caccaacctg      900
gcttccagca ccatcgtgaa ggagggtgcc aacaaggagg tgctgggaat cctggtgtcc      960
tacagggtca aggtgaagct ggtggtgtct cgaggcgggg atgtctctgt ggagctgcct     1020
tttgttctta tgcacccccaa gccccacgac cacatccccc tccccagacc ccagtcagcc     1080
gctccggaga cagatgtccc tgtggacacc aacctcattg aatttgatac caactatgcc     1140
acagatgatg acattgtgtt tgaggacttt gcccggcttc ggctgaaggg gatgaaggat     1200
gacgactatg atgatcaact ctgc                                           1224
```

<210> SEQ ID NO 28
<211> LENGTH: 408
<212> TYPE: PRT
<213> ORGANISM: Artificial Sequence
<220> FEATURE:
<223> OTHER INFORMATION: BArr 4A Beta-arrestin-2
<220> FEATURE:
<221> NAME/KEY: SITE
<222> LOCATION: (1)..(408)
<223> OTHER INFORMATION: B-arrestin

<400> SEQUENCE: 28

```
Gly Glu Lys Pro Gly Thr Arg Val Phe Lys Lys Ser Ser Pro Asn Cys
1               5                   10                  15

Lys Leu Thr Val Tyr Leu Gly Lys Arg Asp Phe Val Asp His Leu Asp
            20                  25                  30

Lys Val Asp Pro Val Asp Gly Val Val Leu Val Asp Pro Asp Tyr Leu
        35                  40                  45

Lys Asp Arg Lys Val Phe Val Thr Leu Thr Cys Ala Phe Arg Tyr Gly
    50                  55                  60

Arg Glu Asp Leu Asp Val Leu Gly Leu Ser Phe Arg Lys Asp Leu Phe
65                  70                  75                  80

Ile Ala Thr Tyr Gln Ala Phe Pro Pro Val Pro Asn Pro Pro Arg Pro
                85                  90                  95

Pro Thr Arg Leu Gln Asp Arg Leu Leu Arg Lys Leu Gly Gln His Ala
            100                 105                 110

His Pro Phe Phe Phe Thr Ile Pro Gln Asn Leu Pro Cys Ser Val Thr
        115                 120                 125

Leu Gln Pro Gly Pro Glu Asp Thr Gly Lys Ala Cys Gly Val Asp Phe
    130                 135                 140

Glu Ile Arg Ala Phe Cys Ala Lys Ser Leu Glu Glu Lys Ser His Lys
```

-continued

```
145              150              155              160

Arg Asn Ser Val Arg Leu Val Ile Arg Lys Val Gln Phe Ala Pro Glu
                165              170              175

Lys Pro Gly Pro Gln Pro Ser Ala Glu Thr Thr Arg His Phe Leu Met
                180              185              190

Ser Asp Arg Ser Leu His Leu Glu Ala Ser Leu Asp Lys Glu Leu Tyr
        195              200              205

Tyr His Gly Glu Pro Leu Asn Val Asn Val His Val Thr Asn Asn Ser
    210              215              220

Thr Lys Thr Val Lys Lys Ile Lys Val Ser Val Arg Gln Tyr Ala Asp
225              230              235              240

Ile Cys Leu Phe Ser Thr Ala Gln Tyr Lys Cys Pro Val Ala Gln Leu
                245              250              255

Glu Gln Asp Asp Gln Val Ser Pro Ser Ser Thr Phe Cys Lys Val Tyr
                260              265              270

Thr Ile Thr Pro Leu Leu Ser Asp Asn Arg Glu Lys Arg Gly Leu Ala
            275              280              285

Leu Asp Gly Lys Leu Lys His Glu Asp Thr Asn Leu Ala Ser Ser Thr
    290              295              300

Ile Val Lys Glu Gly Ala Asn Lys Glu Val Leu Gly Ile Leu Val Ser
305              310              315              320

Tyr Arg Val Lys Val Lys Leu Val Val Ser Arg Gly Gly Asp Val Ser
                325              330              335

Val Glu Leu Pro Phe Val Leu Met His Pro Lys Pro His Asp His Ile
                340              345              350

Pro Leu Pro Arg Pro Gln Ser Ala Ala Pro Glu Thr Asp Val Pro Val
            355              360              365

Asp Thr Asn Leu Ile Glu Phe Asp Thr Asn Tyr Ala Thr Asp Asp Asp
    370              375              380

Ile Val Phe Glu Asp Phe Ala Arg Leu Arg Leu Lys Gly Met Lys Asp
385              390              395              400

Asp Asp Tyr Asp Asp Gln Leu Cys
                405
```

```
<210> SEQ ID NO 29
<211> LENGTH: 261
<212> TYPE: DNA
<213> ORGANISM: Artificial Sequence
<220> FEATURE:
<223> OTHER INFORMATION: BArr 4A - mNeonGreen Part 2
<220> FEATURE:
<221> NAME/KEY: misc_feature
<222> LOCATION: (1)..(261)
<223> OTHER INFORMATION: mNeonGreen Part 2

<400> SEQUENCE: 29
tcgaagaaga cttaccccaa cgacaaaacc atcatcagta cctttaagtg gagttacacc      60
actggaaatg gcaagcgcta ccggagcact gcgcggacca cctacacctt tgccaagcca     120
atggcggcta actatctgaa gaaccagccg atgtacgtgt ccgtaagac ggagctcaag     180 cactccaaga ccgagctcaa cttcaaggag tggcaaaagg cctttaccga tgtgatgggc     240
atggacgagc tgtacaagta g                                               261

<210> SEQ ID NO 30
<211> LENGTH: 86
<212> TYPE: PRT
<213> ORGANISM: Artificial Sequence
```

-continued

```
<220> FEATURE:
<223> OTHER INFORMATION: BArr 4A - mNeonGreen Part 2
<220> FEATURE:
<221> NAME/KEY: SITE
<222> LOCATION: (1)..(86)
<223> OTHER INFORMATION: mNeonGreen Part 2

<400> SEQUENCE: 30

Ser Lys Lys Thr Tyr Pro Asn Asp Lys Thr Ile Ile Ser Thr Phe Lys
1               5                   10                  15

Trp Ser Tyr Thr Thr Gly Asn Gly Lys Arg Tyr Arg Ser Thr Ala Arg
            20                  25                  30

Thr Thr Tyr Thr Phe Ala Lys Pro Met Ala Ala Asn Tyr Leu Lys Asn
        35                  40                  45

Gln Pro Met Tyr Val Phe Arg Lys Thr Glu Leu Lys His Ser Lys Thr
    50                  55                  60

Glu Leu Asn Phe Lys Glu Trp Gln Lys Ala Phe Thr Asp Val Met Gly
65                  70                  75                  80

Met Asp Glu Leu Tyr Lys
                85

<210> SEQ ID NO 31
<211> LENGTH: 7094
<212> TYPE: DNA
<213> ORGANISM: Artificial Sequence
<220> FEATURE:
<223> OTHER INFORMATION: BArr 5A - plasmid
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1039)..(1864)
<223> OTHER INFORMATION: CMV Intron
<220> FEATURE:
<221> NAME/KEY: misc_feature
<222> LOCATION: (1936)..(2385)
<223> OTHER INFORMATION: mNeonGreen
<220> FEATURE:
<221> NAME/KEY: misc_feature
<222> LOCATION: (2386)..(2394)
<223> OTHER INFORMATION: N-terminal linker
<220> FEATURE:
<221> NAME/KEY: misc_feature
<222> LOCATION: (2386)..(2397)
<223> OTHER INFORMATION: N-terminal linker
<220> FEATURE:
<221> NAME/KEY: misc_feature
<222> LOCATION: (2395)..(3618)
<223> OTHER INFORMATION: B-arrestin
<220> FEATURE:
<221> NAME/KEY: misc_feature
<222> LOCATION: (3619)..(3624)
<223> OTHER INFORMATION: C-terminal linker
<220> FEATURE:
<221> NAME/KEY: misc_feature
<222> LOCATION: (3625)..(3885)
<223> OTHER INFORMATION: mNeonGreen
<220> FEATURE:
<221> NAME/KEY: misc_feature
<222> LOCATION: (4024)..(4248)
<223> OTHER INFORMATION: bGH poly(A) signal
<220> FEATURE:
<221> NAME/KEY: misc_feature
<222> LOCATION: (4843)..(5431)
<223> OTHER INFORMATION: ori
<220> FEATURE:
```

-continued

```
<221> NAME/KEY: misc_feature
<222> LOCATION: (5974)..(6789)
<223> OTHER INFORMATION: KanR

<400> SEQUENCE: 31
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg ggtgaaatac cgcacagatg cgtaaggaga aaataccgca tcagattggc     240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca cccccgcttc cttatgctat    1140
aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt atttttacag    1320
gatggggtcc catttattat ttacaaattc acatatacaa caacgccgtc ccccgtgccc    1380 gcagtttta ttaaacatag cgtgggatct ccacgcgaat ctcgggtacg tgttccggac    1440
atgggctctt ctccggtagc ggcggagctt ccacatccga gccctggtcc catgcctcca    1500
gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
ttgcggtgct gttaacggtg gagggcagtg tagtctgagc agtactcgtt gctgccgcgc    1800
gcgccaccag acataatagc tgacagacta acagactgtt cctttccatg ggtctttct    1860 gcagtcaccg tcgtcgacac gtgtgatcag atatacgact cactataggg agacccaagc    1920
tggctagcgt ttaccatggt gagcaagggc gaggaggata catggcctc tctcccagcg    1980 acacatgagt tacacatctt ggctccatc aacggtgtgg actttgacat ggtgggtcag    2040
ggcaccggca atccaaatga tggttatgag gagttaaacc tgaagtccac caagggtgac    2100
ctccagttct cccctggat tctggtccct catatcgggg atggcttcca tcagtacctg    2160
ccctaccctg acgggatgtc gcctttccag gccgccatgg tagatggctc cggataccaa    2220
```

-continued

```
gtccatcgca caatgcagtt tgaagatggt gcctccctta ctgttaacta ccgctacacc   2280
tacgagggaa gccacatcaa aggagaggcc caggtgaagg ggactggttt ccctgctgac   2340
ggtcctgtga tgaccaactc gctgaccgct gcggactggt gcaggatgcg cggagggggag  2400 aaacccggga ccagggtctt caagaagtcg agccctaact gcaagctcac cgtgtacttg   2460
ggcaagcggg acttcgtaga tcacctggac aaagtggacc ctgtagatgg cgtggtgctt   2520
gtggaccctg actacctgaa ggaccgcaaa gtgtttgtga ccctcacctg cgccttccgc   2580
tatggccgtg aagacctgga tgtgctgggc ttgtccttcc gcaaagacct gttcatcgcc   2640
acctaccagg ccttccccc ggtgcccaac ccaccccggc cccccacccg cctgcaggac    2700
cggctgctga ggaagctggg ccagcatgcc cacccttct tcttcaccat accccagaat    2760
cttccatgct ccgtcacact gcagccaggc ccagaggata caggaaaggc ctgcggcgta   2820
gactttgaga ttcgagcctt ctgtgctaaa tcactagaag agaaaagcca caaaggaac    2880 tctgtgcggc tggtgatccg aaaggtgcag ttcgccccgg agaaacccgg ccccagcct    2940 tcagccgaaa ccacacgcca cttcctcatg tctgaccggt ccctgcacct cgaggcttcc   3000
ctggacaagg agctgtacta ccatgggag cccctcaatg taaatgtcca cgtcaccaac    3060
aactccacca agaccgtcaa gaagatcaaa gtctctgtga cacagtacgc cgacatctgc   3120
ctcttcagca ccgcccagta caagtgtcct gtggctcaac tcgaacaaga tgaccaggta   3180
tctcccagct ccacattctg taaggtgtac accataaccc cactgctcag cgacaaccgg   3240
gagaagcggg gtctcgccct ggatgggaaa ctcaagcacg aggacaccaa cctggcttcc   3300
agcaccatcg tgaaggaggg tgccaacaag gaggtgctgg gaatcctggt gtcctacagg   3360
gtcaaggtga gctggtggt gtctcgaggc ggggatgtct ctgtggagct gccttttgtt   3420
cttatgcacc ccaagcccca cgaccacatc cccctcccca gaccccagtc agccgctccg   3480
gagacagatg tccctgtgga caccaacctc attgaatttg ataccaacta tgccacagat   3540
gatgacattg tgtttgagga cttttgcccgg cttcggctga aggggatgaa ggatgacgac   3600
tatgatgatc aactctgcaa tgtttcgaag aagacttacc ccaacgacaa aaccatcatc   3660 agtacctta agtggagtta caccactgga aatggcaagc gctaccggag cactgcgcgg    3720
accacctaca cctttgccaa gccaatggcg gctaactatc tgaagaacca gccgatgtac   3780
gtgttccgta agacggagct caagcactcc aagaccgagc tcaacttcaa ggagtggcaa   3840 aaggcctta ccgatgtgat gggcatggac gagctgtaca agtagcgcgc cctcgactgt    3900
gccttctagt tgccagccat ctgtatcgcg gccgctctag accaggcgcc tggatccaga   3960
tcacttctgg ctaataaaag atcagagctc tagagatctg tgtgttggtt ttttgtggat   4020
ctgctgtgcc ttctagttgc cagccatctg ttgtttgccc ctccccgtg ccttccttga    4080 ccctggaagg tgccactccc actgtccttt cctaataaaa tgaggaaatt gcatcgcatt   4140
gtctgagtag gtgtcattct attctggggg gtggggtggg gcagcacagc aaggggggag   4200
attgggaaga caatagcagg catgctgggg atgcggtggg ctctatgggt acctctctct   4260
ctctctctct ctctctctct ctctctctct ctcggtacct ctctctctct ctctctctct   4320
ctctctctct ctctctctcg gtaccaggtg ctgaagaatt gacccggttc ctcctgggcc   4380
agaaagaagc aggcacatcc ccttctctgt gacacaccct gtccacgccc ctggttctta   4440
gttccagccc cactcatagg acactcatag ctcaggaggg ctccgccttc aatcccaccc   4500
gctaaagtac ttggagcggt ctctccctcc ctcatcagcc caccaaacca aacctagcct   4560
```

-continued

```
ccaagagtgg gaagaaatta aagcaagata ggctattaag tgcagaggga gagaaaatgc    4620
ctccaacatg tgaggaagta atgagagaaa tcatagaatt tcttccgctt cctcgctcac    4680
tgactcgctg cgctcggtcg ttcggctgcg gcgagcggta tcagctcact caaaggcggt    4740
aatacggtta tccacagaat caggggataa cgcaggaaag aacatgtgag caaaaggcca    4800
gcaaaaggcc aggaaccgta aaaaggccgc gttgctggcg tttttccata ggctccgccc    4860
ccctgacgag catcacaaaa atcgacgctc aagtcagagg tggcgaaacc cgacaggact    4920
ataaagatac caggcgtttc cccctggaag ctccctcgtg cgctctcctg ttccgaccct    4980
gccgcttacc ggatacctgt ccgcctttct cccttcggga agcgtggcgc tttctcaatg    5040
ctcacgctgt aggtatctca gttcggtgta ggtcgttcgc tccaagctgg gctgtgtgca    5100
cgaacccccc gttcagcccg accgctgcgc cttatccggt aactatcgtc ttgagtccaa    5160
cccggtaaga cacgacttat cgccactggc agcagccact ggtaacagga ttagcagagc    5220
gaggtatgta ggcggtgcta cagagttctt gaagtggtgg cctaactacg gctacactag    5280
aaggacagta tttggtatct gcgctctgct gaagccagtt accttcggaa aaagagttgg    5340
tagctcttga tccggcaaac aaaccaccgc tggtagcggt ggtttttttg tttgcaagca    5400
gcagattacg cgcagaaaaa aaggatctca agaagatcct ttgatctttt ctacggggtc    5460
tgacgctcag tggaacgaaa actcacgtta agggattttg gtcatgagat tatcaaaaag    5520
gatcttcacc tagatccttt taaattaaaa atgaagtttt aaatcaatct aaagtatata    5580
tgagtaaact tggtctgaca gttaccaatg cttaatcagt gaggcaccta tctcagcgat    5640
ctgtctattt cgttcatcca tagttgcctg actccggggg ggggggcgc tgaggtctgc     5700 ctcgtgaaga aggtgttgct gactcatacc aggcctgaat cgccccatca tccagccaga    5760
aagtgaggga gccacggttg atgagagctt tgttgtaggt ggaccagttg gtgattttga    5820
acttttgctt tgccacggaa cggtctgcgt tgtcgggaag atgcgtgatc tgatccttca    5880
actcagcaaa agttcgattt attcaacaaa gccgccgtcc cgtcaagtca gcgtaatgct    5940
ctgccagtgt tacaaccaat taaccaattc tgattagaaa aactcatcga gcatcaaatg    6000
aaactgcaat ttattcatat caggattatc aataccatat ttttgaaaaa gccgtttctg    6060
taatgaagga gaaaactcac cgaggcagtt ccataggatg gcaagatcct ggtatcggtc    6120
tgcgattccg actcgtccaa catcaataca acctattaat ttcccctcgt caaaaataag    6180
gttatcaagt gagaaatcac catgagtgac gactgaatcc ggtgagaatg gcaaaagctt    6240
atgcatttct ttccagactt gttcaacagg ccagccatta cgctcgtcat caaaatcact    6300
cgcatcaacc aaaccgttat tcattcgtga ttgcgcctga gcgagacgaa atacgcgatc    6360
gctgttaaaa ggacaattac aaacaggaat cgaatgcaac cggcgcagga acactgccag    6420
cgcatcaaca atattttcac ctgaatcagg atattcttct aatacctgga atgctgtttt    6480 cccgggatc gcagtggtga gtaaccatgc atcatcagga gtacggataa aatgcttgat     6540
ggtcggaaga ggcataaatt ccgtcagcca gtttagtctg accatctcat ctgtaacatc    6600
attggcaacg ctacctttgc catgtttcag aaacaactct ggcgcatcgg gcttcccata    6660
caatcgatag attgtcgcac ctgattgccc gacattatcg cgagcccatt tatacccata    6720
taaatcagca tccatgttgg aatttaatcg cggcctcgag caagacgttt cccgttgaat    6780
atggctcata acaccccttg tattactgtt tatgtaagca gacagtttta ttgttcatga    6840
tgatatattt ttatcttgtg caatgtaaca tcagagattt tgagacacaa cgtggctttc    6900 ccccccccccc cattattgaa gcatttatca gggttattgt ctcatgagcg gatacatatt    6960
```

```
tgaatgtatt tagaaaaata aacaaatagg ggttccgcgc acatttcccc gaaaagtgcc    7020
acctgacgtc taagaaacca ttattatcat gacattaacc tataaaaata ggcgtatcac    7080
gaggcccttt cgtc                                                      7094
```

```
<210> SEQ ID NO 32
<211> LENGTH: 1950
<212> TYPE: DNA
<213> ORGANISM: Artificial Sequence
<220> FEATURE:
<223> OTHER INFORMATION: BArr 5A - coding sequence
<220> FEATURE:
<221> NAME/KEY: misc_feature
<222> LOCATION: (1)..(450)
<223> OTHER INFORMATION: mNeonGreen Part 1
<220> FEATURE:
<221> NAME/KEY: misc_feature
<222> LOCATION: (451)..(459)
<223> OTHER INFORMATION: N-terminal linker
<220> FEATURE:
<221> NAME/KEY: misc_feature
<222> LOCATION: (451)..(462)
<223> OTHER INFORMATION: N-terminal linker
<220> FEATURE:
<221> NAME/KEY: misc_feature
<222> LOCATION: (460)..(1683)
<223> OTHER INFORMATION: B-arrestin
<220> FEATURE:
<221> NAME/KEY: misc_feature
<222> LOCATION: (1684)..(1689)
<223> OTHER INFORMATION: C-terminal linker
<220> FEATURE:
<221> NAME/KEY: misc_feature
<222> LOCATION: (1690)..(1950)
<223> OTHER INFORMATION: mNeonGreen Part 2
```

```
<400> SEQUENCE: 32
atggtgagca agggcgagga ggataacatg gcctctctcc cagcgacaca tgagttacac      60
atctttggct ccatcaacgg tgtggacttt gacatggtgg tcagggcac cggcaatcca     120 aatgatggtt atgaggagtt aaacctgaag tccaccaagg gtgacctcca gttctccccc     180
tggattctgg tccctcatat cgggtatggc ttccatcagt acctgcccta ccctgacggg     240
atgtcgcctt ccaggccgc catggtagat ggctccggat accaagtcca tcgcacaatg     300
cagtttgaag atggtgcctc ccttactgtt aactaccgct acacctacga gggaagccac     360
atcaaaggag aggcccaggt gaaggggact ggtttccctg ctgacggtcc tgtgatgacc     420
aactcgctga ccgctgcgga ctggtgcagg atgcgcggag gggagaaacc cgggaccagg     480
gtcttcaaga agtcgagccc taactgcaag ctcaccgtgt acttgggcaa gcgggacttc     540
gtagatcacc tggacaaagt ggaccctgta gatggcgtgg tgcttgtgga ccctgactac     600
ctgaaggacc gcaaagtgtt tgtgaccctc acctgcgcct ccgctatgg ccgtgaagac     660 ctggatgtgc tgggcttgtc cttccgcaaa gacctgttca tcgccaccta ccaggccttc     720
cccccggtgc ccaacccacc ccggcccccc accgcctgc aggaccggct gctgaggaag     780
ctgggccagc atgcccaccc cttcttcttc accatacccc agaatcttcc atgctccgtc     840
acactgcagc caggcccaga ggatacagga aaggcctgcg gcgtagactt tgagattcga     900
gccttctgtg ctaaatcact agaagagaaa agccacaaaa ggaactctgt gcggctggtg     960
atccgaaagg tgcagttcgc cccggagaaa cccggccccc agccttcagc cgaaaccaca    1020
cgccacttcc tcatgtctga ccggtccctg cacctcgagg cttccctgga caaggagctg    1080
tactaccatg gggagcccct caatgtaaat gtccacgtca ccaacaactc caccaagacc    1140
```

```
gtcaagaaga tcaaagtctc tgtgagacag tacgccgaca tctgcctctt cagcaccgcc      1200
cagtacaagt gtcctgtggc tcaactcgaa caagatgacc aggtatctcc cagctccaca      1260
ttctgtaagg tgtacaccat aaccccactg ctcagcgaca accgggagaa gcggggtctc      1320
gccctggatg ggaaactcaa gcacgaggac accaacctgg cttccagcac catcgtgaag      1380
gagggtgcca acaaggaggt gctgggaatc ctggtgtcct acagggtcaa ggtgaagctg      1440
gtggtgtctc gaggcgggga tgtctctgtg gagctgcctt ttgttcttat gcaccccaag      1500
ccccacgacc acatccccct ccccagaccc cagtcagccg ctccggagac agatgtccct      1560
gtggacacca acctcattga atttgatacc aactatgcca cagatgatga cattgtgttt      1620
gaggactttg cccggcttcg gctgaagggg atgaaggatg acgactatga tgatcaactc      1680
tgcaatgttt cgaagaagac ttaccccaac gacaaaacca tcatcagtac ctttaagtgg      1740
agttacacca ctggaaatgg caagcgctac cggagcactg cgcggaccac ctacaccttt      1800
gccaagccaa tggcggctaa ctatctgaag aaccagccga tgtacgtgtt ccgtaagacg      1860
gagctcaagc actccaagac cgagctcaac ttcaaggagt ggcaaaaggc ctttaccgat      1920
gtgatgggca tggacgagct gtacaagtag                                       1950
```

```
<210> SEQ ID NO 33
<211> LENGTH: 649
<212> TYPE: PRT
<213> ORGANISM: Artificial Sequence
<220> FEATURE:
<223> OTHER INFORMATION: BArr 5A - coding sequence
<220> FEATURE:
<221> NAME/KEY: SITE
<222> LOCATION: (1)..(150)
<223> OTHER INFORMATION: mNeonGreen Part 1
<220> FEATURE:
<221> NAME/KEY: SITE
<222> LOCATION: (151)..(153)
<223> OTHER INFORMATION: N-terminal linker
<220> FEATURE:
<221> NAME/KEY: SITE
<222> LOCATION: (151)..(154)
<223> OTHER INFORMATION: N-terminal linker
<220> FEATURE:
<221> NAME/KEY: SITE
<222> LOCATION: (155)..(561)
<223> OTHER INFORMATION: B-arrestin
<220> FEATURE:
<221> NAME/KEY: SITE
<222> LOCATION: (562)..(563)
<223> OTHER INFORMATION: C-terminal linker
<220> FEATURE:
<221> NAME/KEY: SITE
<222> LOCATION: (564)..(649)
<223> OTHER INFORMATION: mNeonGreen Part 2

<400> SEQUENCE: 33
```

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95
```

-continued

```
His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
            115                 120                 125

Gly Thr Gly Phe Pro Ala Asp Gly Pro Val Met Thr Asn Ser Leu Thr
        130                 135                 140

Ala Ala Asp Trp Cys Arg Met Arg Gly Gly Glu Lys Pro Gly Thr Arg
145                 150                 155                 160

Val Phe Lys Lys Ser Ser Pro Asn Cys Lys Leu Thr Val Tyr Leu Gly
                165                 170                 175

Lys Arg Asp Phe Val Asp His Leu Asp Lys Val Asp Pro Val Asp Gly
            180                 185                 190

Val Val Leu Val Asp Pro Asp Tyr Leu Lys Asp Arg Lys Val Phe Val
            195                 200                 205

Thr Leu Thr Cys Ala Phe Arg Tyr Gly Arg Glu Asp Leu Asp Val Leu
    210                 215                 220

Gly Leu Ser Phe Arg Lys Asp Leu Phe Ile Ala Thr Tyr Gln Ala Phe
225                 230                 235                 240

Pro Pro Val Pro Asn Pro Pro Arg Pro Pro Thr Arg Leu Gln Asp Arg
                245                 250                 255

Leu Leu Arg Lys Leu Gly Gln His Ala His Pro Phe Phe Phe Thr Ile
            260                 265                 270

Pro Gln Asn Leu Pro Cys Ser Val Thr Leu Gln Pro Gly Pro Glu Asp
        275                 280                 285

Thr Gly Lys Ala Cys Gly Val Asp Phe Glu Ile Arg Ala Phe Cys Ala
    290                 295                 300

Lys Ser Leu Glu Glu Lys Ser His Lys Arg Asn Ser Val Arg Leu Val
305                 310                 315                 320

Ile Arg Lys Val Gln Phe Ala Pro Glu Lys Pro Gly Pro Gln Pro Ser
                325                 330                 335

Ala Glu Thr Thr Arg His Phe Leu Met Ser Asp Arg Ser Leu His Leu
            340                 345                 350

Glu Ala Ser Leu Asp Lys Glu Leu Tyr Tyr His Gly Glu Pro Leu Asn
        355                 360                 365

Val Asn Val His Val Thr Asn Asn Ser Thr Lys Thr Val Lys Lys Ile
    370                 375                 380

Lys Val Ser Val Arg Gln Tyr Ala Asp Ile Cys Leu Phe Ser Thr Ala
385                 390                 395                 400

Gln Tyr Lys Cys Pro Val Ala Gln Leu Glu Gln Asp Asp Gln Val Ser
                405                 410                 415

Pro Ser Ser Thr Phe Cys Lys Val Tyr Thr Ile Thr Pro Leu Leu Ser
            420                 425                 430

Asp Asn Arg Glu Lys Arg Gly Leu Ala Leu Asp Gly Lys Leu Lys His
        435                 440                 445

Glu Asp Thr Asn Leu Ala Ser Ser Thr Ile Val Lys Glu Gly Ala Asn
    450                 455                 460

Lys Glu Val Leu Gly Ile Leu Val Ser Tyr Arg Val Lys Val Lys Leu
465                 470                 475                 480

Val Val Ser Arg Gly Gly Asp Val Ser Val Glu Leu Pro Phe Val Leu
                485                 490                 495

Met His Pro Lys Pro His Asp His Ile Pro Leu Pro Arg Pro Gln Ser
            500                 505                 510
```

-continued

Ala Ala Pro Glu Thr Asp Val Pro Val Asp Thr Asn Leu Ile Glu Phe
        515                 520                 525

Asp Thr Asn Tyr Ala Thr Asp Asp Asp Ile Val Phe Glu Asp Phe Ala
        530                 535                 540

Arg Leu Arg Leu Lys Gly Met Lys Asp Asp Asp Tyr Asp Asp Gln Leu
545                 550                 555                 560

Cys Asn Val Ser Lys Lys Thr Tyr Pro Asn Asp Lys Thr Ile Ile Ser
                565                 570                 575

Thr Phe Lys Trp Ser Tyr Thr Thr Gly Asn Gly Lys Arg Tyr Arg Ser
                580                 585                 590

Thr Ala Arg Thr Thr Tyr Thr Phe Ala Lys Pro Met Ala Ala Asn Tyr
                595                 600                 605

Leu Lys Asn Gln Pro Met Tyr Val Phe Arg Lys Thr Glu Leu Lys His
        610                 615                 620

Ser Lys Thr Glu Leu Asn Phe Lys Glu Trp Gln Lys Ala Phe Thr Asp
625                 630                 635                 640

Val Met Gly Met Asp Glu Leu Tyr Lys
                645

<210> SEQ ID NO 34
<211> LENGTH: 450
<212> TYPE: DNA
<213> ORGANISM: Artificial Sequence
<220> FEATURE:
<223> OTHER INFORMATION: BArr 5A - mNeonGreen Part 1
<220> FEATURE:
<221> NAME/KEY: misc_feature
<222> LOCATION: (1)..(450)
<223> OTHER INFORMATION: mNeonGreen Part 1

<400> SEQUENCE: 34
atggtgagca agggcgagga ggataacatg gcctctctcc cagcgacaca tgagttacac        60
atctttggct ccatcaacgg tgtggacttt gacatggtgg tcagggcac cggcaatcca        120 aatgatggtt atgaggagtt aaacctgaag tccaccaagg gtgacctcca gttctccccc        180
tggattctgg tccctcatat cgggtatggc ttccatcagt acctgcccta ccctgacggg        240
atgtcgcctt ccaggccgc catggtagat ggctccggat accaagtcca tcgcacaatg        300
cagtttgaag atggtgcctc ccttactgtt aactaccgct acacctacga gggaagccac        360
atcaaaggag aggcccaggt gaagggact ggtttccctg ctgacggtcc tgtgatgacc        420
aactcgctga ccgctgcgga ctggtgcagg        450

<210> SEQ ID NO 35
<211> LENGTH: 150
<212> TYPE: PRT
<213> ORGANISM: Artificial Sequence
<220> FEATURE:
<223> OTHER INFORMATION: BArr 5A - mNeonGreen Part 1
<220> FEATURE:
<221> NAME/KEY: SITE
<222> LOCATION: (1)..(150)
<223> OTHER INFORMATION: mNeonGreen Part 1

<400> SEQUENCE: 35

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
                20                  25                  30

Val Gly Gln Gly Thr Gly Asn Pro Asn Asp Gly Tyr Glu Glu Leu Asn
        35                  40                  45

```
Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
                100                 105                 110

Arg Tyr Thr Tyr Glu Gly Ser His Ile Lys Gly Glu Ala Gln Val Lys
            115                 120                 125

Gly Thr Gly Phe Pro Ala Asp Gly Pro Val Met Thr Asn Ser Leu Thr
        130                 135                 140

Ala Ala Asp Trp Cys Arg
145                 150

<210> SEQ ID NO 36
<211> LENGTH: 1224
<212> TYPE: DNA
<213> ORGANISM: Artificial Sequence
<220> FEATURE:
<223> OTHER INFORMATION: BArr 5A - Beta-arrestin-2
<220> FEATURE:
<221> NAME/KEY: SITE
<222> LOCATION: (1)..(1224)
<223> OTHER INFORMATION: B-arrestin

<400> SEQUENCE: 36
ggggagaaac ccgggaccag ggtcttcaag aagtcgagcc ctaactgcaa gctcaccgtg      60
tacttgggca agcgggactt cgtagatcac ctggacaaag tggaccctgt agatggcgtg     120
gtgcttgtgg accctgacta cctgaaggac cgcaaagtgt ttgtgaccct cacctgcgcc     180
ttccgctatg ccgtgaaga cctggatgtg ctgggcttgt ccttccgcaa agacctgttc     240
atcgccacct accaggcctt cccccggtg cccaacccac cccggccccc cacccgcctg     300
caggaccggc tgctgaggaa gctgggccag catgcccacc ccttcttctt caccataccc     360
cagaatcttc catgctccgt cacactgcag ccaggcccag aggatacagg aaaggcctgc     420
ggcgtagact ttgagattcg agccttctgt gctaaatcac tagaagagaa aagccacaaa     480
aggaactctg tgcggctggt gatccgaaag gtgcagttcg ccccggagaa acccggcccc     540
cagccttcag ccgaaaccac acgccacttc ctcatgtctg accggtccct gcacctcgag     600
gcttccctgg acaaggagct gtactaccat ggggagcccc tcaatgtaaa tgtccacgtc     660
accaacaact ccaccaagac cgtcaagaag atcaaagtct ctgtgagaca gtacgccgac     720
atctgcctct tcagcaccgc ccagtacaag tgtcctgtgg ctcaactcga acaagatgac     780
caggtatctc ccagctccac attctgtaag gtgtacacca taaccccact gctcagcgac     840
aaccgggaga agcggggtct cgccctggat gggaaactca gcacgagga caccaacctg     900 gcttccagca ccatcgtgaa ggagggtgcc aacaaggagg tgctgggaat cctggtgtcc     960
tacagggtca aggtgaagct ggtggtgtct cgaggcgggg atgtctctgt ggagctgcct    1020
tttgttctta tgcaccccaa gccccacgac cacatccccc tccccagacc ccagtcagcc    1080
gctccggaga cagatgtccc tgtggacacc aacctcattg aatttgatac caactatgcc    1140
acagatgatg acattgtgtt tgaggacttt gcccggcttc ggctgaaggg gatgaaggat    1200
gacgactatg atgatcaact ctgc                                          1224
```

<210> SEQ ID NO 37
<211> LENGTH: 408
<212> TYPE: PRT
<213> ORGANISM: Artificial Sequence
<220> FEATURE:
<223> OTHER INFORMATION: BArr 5A - Beta-arrestin-2
<220> FEATURE:
<221> NAME/KEY: SITE
<222> LOCATION: (1)..(408)
<223> OTHER INFORMATION: B-arrestin

<400> SEQUENCE: 37

Gly Glu Lys Pro Gly Thr Arg Val Phe Lys Lys Ser Ser Pro Asn Cys
1               5                   10                  15

Lys Leu Thr Val Tyr Leu Gly Lys Arg Asp Phe Val Asp His Leu Asp
            20                  25                  30

Lys Val Asp Pro Val Asp Gly Val Val Leu Val Asp Pro Asp Tyr Leu
        35                  40                  45

Lys Asp Arg Lys Val Phe Val Thr Leu Thr Cys Ala Phe Arg Tyr Gly
    50                  55                  60

Arg Glu Asp Leu Asp Val Leu Gly Leu Ser Phe Arg Lys Asp Leu Phe
65                  70                  75                  80

Ile Ala Thr Tyr Gln Ala Phe Pro Pro Val Pro Asn Pro Pro Arg Pro
                85                  90                  95

Pro Thr Arg Leu Gln Asp Arg Leu Leu Arg Lys Leu Gly Gln His Ala
            100                 105                 110

His Pro Phe Phe Phe Thr Ile Pro Gln Asn Leu Pro Cys Ser Val Thr
            115                 120                 125

Leu Gln Pro Gly Pro Glu Asp Thr Gly Lys Ala Cys Gly Val Asp Phe
    130                 135                 140

Glu Ile Arg Ala Phe Cys Ala Lys Ser Leu Glu Glu Lys Ser His Lys
145                 150                 155                 160

Arg Asn Ser Val Arg Leu Val Ile Arg Lys Val Gln Phe Ala Pro Glu
                165                 170                 175

Lys Pro Gly Pro Gln Pro Ser Ala Glu Thr Thr Arg His Phe Leu Met
            180                 185                 190

Ser Asp Arg Ser Leu His Leu Glu Ala Ser Leu Asp Lys Glu Leu Tyr
            195                 200                 205

Tyr His Gly Glu Pro Leu Asn Val Asn Val His Val Thr Asn Asn Ser
    210                 215                 220

Thr Lys Thr Val Lys Lys Ile Lys Val Ser Val Arg Gln Tyr Ala Asp
225                 230                 235                 240

Ile Cys Leu Phe Ser Thr Ala Gln Tyr Lys Cys Pro Val Ala Gln Leu
                245                 250                 255

Glu Gln Asp Asp Gln Val Ser Pro Ser Ser Thr Phe Cys Lys Val Tyr
            260                 265                 270

Thr Ile Thr Pro Leu Leu Ser Asp Asn Arg Glu Lys Arg Gly Leu Ala
        275                 280                 285

Leu Asp Gly Lys Leu Lys His Glu Asp Thr Asn Leu Ala Ser Ser Thr
    290                 295                 300

Ile Val Lys Glu Gly Ala Asn Lys Glu Val Leu Gly Ile Leu Val Ser
305                 310                 315                 320

Tyr Arg Val Lys Val Lys Leu Val Val Ser Arg Gly Gly Asp Val Ser
            325                 330                 335

Val Glu Leu Pro Phe Val Leu Met His Pro Lys Pro His Asp His Ile
            340                 345                 350

-continued

```
Pro Leu Pro Arg Pro Gln Ser Ala Ala Pro Glu Thr Asp Val Pro Val
        355             360             365

Asp Thr Asn Leu Ile Glu Phe Asp Thr Asn Tyr Ala Thr Asp Asp Asp
        370             375             380

Ile Val Phe Glu Asp Phe Ala Arg Leu Arg Leu Lys Gly Met Lys Asp
385             390             395             400

Asp Asp Tyr Asp Asp Gln Leu Cys
                405
```

```
<210> SEQ ID NO 38
<211> LENGTH: 261
<212> TYPE: DNA
<213> ORGANISM: Artificial Sequence
<220> FEATURE:
<223> OTHER INFORMATION: BArr 5A - mNeonGreen Part 2
<220> FEATURE:
<221> NAME/KEY: SITE
<222> LOCATION: (1)..(261)
<223> OTHER INFORMATION: mNeonGreen Part 2

<400> SEQUENCE: 38
tcgaagaaga cttaccccaa cgacaaaacc atcatcagta cctttaagtg gagttacacc      60
actggaaatg gcaagcgcta ccggagcact gcgcggacca cctacacctt tgccaagcca     120
atggcggcta actatctgaa gaaccagccg atgtacgtgt tccgtaagac ggagctcaag     180
cactccaaga ccgagctcaa cttcaaggag tggcaaaagg cctttaccga tgtgatgggc     240
atggacgagc tgtacaagta g                                               261
```

```
<210> SEQ ID NO 39
<211> LENGTH: 86
<212> TYPE: PRT
<213> ORGANISM: Artificial Sequence
<220> FEATURE:
<223> OTHER INFORMATION: BArr 5A - mNeonGreen Part 2
<220> FEATURE:
<221> NAME/KEY: SITE
<222> LOCATION: (1)..(86)
<223> OTHER INFORMATION: mNeonGreen Part 2

<400> SEQUENCE: 39
```

```
Ser Lys Lys Thr Tyr Pro Asn Asp Lys Thr Ile Ile Ser Thr Phe Lys
1               5               10              15

Trp Ser Tyr Thr Thr Gly Asn Gly Lys Arg Tyr Arg Ser Thr Ala Arg
        20              25              30

Thr Thr Tyr Thr Phe Ala Lys Pro Met Ala Ala Asn Tyr Leu Lys Asn
        35              40              45

Gln Pro Met Tyr Val Phe Arg Lys Thr Glu Leu Lys His Ser Lys Thr
        50              55              60

Glu Leu Asn Phe Lys Glu Trp Gln Lys Ala Phe Thr Asp Val Met Gly
65              70              75              80

Met Asp Glu Leu Tyr Lys
                85
```

```
<210> SEQ ID NO 40
<211> LENGTH: 7085
<212> TYPE: DNA
<213> ORGANISM: Artificial Sequence
<220> FEATURE:
<223> OTHER INFORMATION: BArr 6B - plasmid
<220> FEATURE:
<221> NAME/KEY: misc_feature
<222> LOCATION: (320)..(699)
<223> OTHER INFORMATION: CMV enhancer
```

-continued

```
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1039)..(1864)
<223> OTHER INFORMATION: CMV Intron
<220> FEATURE:
<221> NAME/KEY: misc_feature
<222> LOCATION: (1936)..(2376)
<223> OTHER INFORMATION: mNeonGreen Part 1
<220> FEATURE:
<221> NAME/KEY: misc_feature
<222> LOCATION: (2377)..(2388)
<223> OTHER INFORMATION: N-terminal linker
<220> FEATURE:
<221> NAME/KEY: misc_feature
<222> LOCATION: (2386)..(3609)
<223> OTHER INFORMATION: B-arrestin
<220> FEATURE:
<221> NAME/KEY: misc_feature
<222> LOCATION: (3610)..(3615)
<223> OTHER INFORMATION: C-terminal linker
<220> FEATURE:
<221> NAME/KEY: misc_feature
<222> LOCATION: (3616)..(3876)
<223> OTHER INFORMATION: mNeonGreen Part 2

<400> SEQUENCE: 40
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg ggtgaaatac cgcacagatg cgtaaggaga aaataccgca tcagattggc     240
tattggccat tgcatacgtt gtatccatat cataatatgt acatttatat ggctcatgt     300 ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca ccccgcttc cttatgctat    1140 aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt attttttacag    1320 gatggggtcc catttattat ttacaaattc acatatacaa caacgccgtc ccccgtgccc    1380 gcagtttttta ttaaacatag cgtgggatct ccacgcgaat ctcgggtacg tgttccggac    1440
```

-continued

```
atgggctctt ctccggtagc ggcggagctt ccacatccga gccctggtcc catgcctcca   1500
gcggctcatg gtcgctcggc agctccttgc tcctaacagt ggaggccaga cttaggcaca   1560
gcacaatgcc caccaccacc agtgtgccgc acaaggccgt ggcggtaggg tatgtgtctg   1620
aaaatgagcg tggagattgg gctcgcacgg ctgacgcaga tggaagactt aaggcagcgg   1680
cagaagaaga tgcaggcagc tgagttgttg tattctgata agagtcagag gtaactcccg   1740
ttgcggtgct gttaacggtg gagggcagtg tagtctgagc agtactcgtt gctgccgcgc   1800
gcgccaccag acataatagc tgacagacta acagactgtt cctttccatg ggtcttttct   1860
gcagtcaccg tcgtcgacac gtgtgatcag atatacgact cactataggg agacccaagc   1920
tggctagcgt ttaccatggt gagcaagggc gaggaggata acatggcctc tctcccagcg   1980
acacatgagt tacacatctt tggctccatc aacggtgtgg actttgacat ggtgggtcag   2040
ggcaccggca atccaaatga tggttatgag gagttaaacc tgaagtccac caagggtgac   2100
ctccagttct ccccctggat tctggtccct catatcgggt atggcttcca tcagtacctg   2160
ccctaccctg acgggatgtc gccttttccag gccgccatgg tagatggctc cggataccaa   2220
gtccatcgca caatgcagtt tgaagatggt gcctcccttta ctgttaacta ccgctacacc   2280
tacgagggaa gccacatcaa aggagaggcc caggtgaagg ggactggttt ccctgctgac   2340
ggtcctgtga tgaccaactc gctgaccgct gcggactgcg acatcgggga gaaacccggg   2400 accaggggtct tcaagaagtc gagccctaac tgcaagctca ccgtgtactt gggcaagcgg   2460
gacttcgtag atcacctgga caaagtggac cctgtagatg gcgtggtgct tgtggaccct   2520
gactacctga aggaccgcaa agtgtttgtg accctcacct gcgccttccg ctatggccgt   2580
gaagacctgg atgtgctggg cttgtccttc cgcaaagacc tgttcatcgc cacctaccag   2640
gccttccccc cggtgcccaa cccaccccgg cccccaccc gcctgcagga ccggctgctg   2700
aggaagctgg gccagcatgc ccacccctc ttcttcacca taccccagaa tcttccatgc   2760
tccgtcacac tgcagccagg cccagaggat acaggaaagg cctgcggcgt agactttgag   2820
attcgagcct tctgtgctaa atcactagaa gagaaaagcc acaaaaggaa ctctgtgcgg   2880
ctggtgatcc gaaaggtgca gttcgccccg gagaaacccg gccccagcc ttcagccgaa   2940 accacacgcc acttcctcat gtctgaccgg tccctgcacc tcgaggcttc cctggacaag   3000
gagctgtact accatgggga gcccctcaat gtaaatgtcc acgtcaccaa caactccacc   3060
aagaccgtca agaagatcaa agtctctgtg agacagtacg ccgacatctg cctcttcagc   3120
accgcccagt acaagtgtcc tgtggctcaa ctcgaacaag atgaccaggt atctcccagc   3180
tccacattct gtaaggtgta caccataacc ccactgctca gcgacaaccg ggagaagcgg   3240
ggtctcgccc tggatgggaa actcaagcac gaggacacca acctggcttc cagcaccatc   3300
gtgaaggagg gtgccaacaa ggaggtgctg ggaatcctgg tgtcctacag ggtcaaggtg   3360
aagctggtgg tgtctcgagg cgggggatgtc tctgtggagc tgccttttgt tcttatgcac   3420
cccaagcccc acgaccacat cccccctcccc agaccccagt cagccgctcc ggagacagat   3480
gtccctgtgg acaccaacct cattgaattt gataccaact atgccacaga tgatgacatt   3540
gtgtttgagg actttgcccg gcttcggctg aagggggatga aggatgacga ctatgatgat   3600
caactctgca atgtttcgaa gaagacttac cccaacgaca aaaccatcat cagtaccttt   3660
aagtggagtt acaccactgg aaatggcaag cgctaccgga gcactgcgcg gaccaccta   3720 acctttgcca agccaatggc ggctaactat ctgaagaacc agccgatgta cgtgttccgt   3780
aagacggagc tcaagcactc caagaccgag ctcaacttca aggagtggca aaaggccttt   3840
```

```
accgatgtga tgggcatgga cgagctgtac aagtagcgcg ccctcgactg tgccttctag   3900
ttgccagcca tctgtatcgc ggccgctcta gaccaggcgc ctggatccag atcacttctg   3960
gctaataaaa gatcagagct ctagagatct gtgtgttggt tttttgtgga tctgctgtgc   4020
cttctagttg ccagccatct gttgtttgcc cctcccccgt gccttccttg accctggaag   4080
gtgccactcc cactgtcctt tcctaataaa atgaggaaat tgcatcgcat tgtctgagta   4140
ggtgtcattc tattctgggg ggtggggtgg ggcagcacag caagggggag gattgggaag   4200
acaatagcag gcatgctggg gatgcggtgg gctctatggg tacctctctc tctctctctc   4260
tctctctctc tctctctctc tctcggtacc tctctctctc tctctctctc tctctctctc   4320
tctctctctc ggtaccaggt gctgaagaat tgacccggtt cctcctgggc cagaaagaag   4380
caggcacatc cccttctctg tgacacaccc tgtccacgcc cctggttctt agttccagcc   4440
ccactcatag gacactcata gctcaggagg gctccgcctt caatcccacc cgctaaagta   4500
cttggagcgg tctctccctc cctcatcagc ccaccaaacc aaacctagcc tccaagagtg   4560
ggaagaaatt aaagcaagat aggctattaa gtgcagaggg agagaaaatg cctccaacat   4620
gtgaggaagt aatgagagaa atcatagaat ttcttccgct tcctcgctca ctgactcgct   4680
gcgctcggtc gttcggctgc ggcgagcggt atcagctcac tcaaaggcgg taatacggtt   4740
atccacagaa tcaggggata acgcaggaaa gaacatgtga gcaaaaggcc agcaaaaggc   4800
caggaaccgt aaaaaggccg cgttgctggc gtttttccat aggctccgcc cccctgacga   4860
gcatcacaaa aatcgacgct caagtcagag gtggcgaaac ccgacaggac tataaagata   4920
ccaggcgttt ccccctggaa gctccctcgt gcgctctcct gttccgaccc tgccgcttac   4980
cggatacctg tccgcctttc tcccttcggg aagcgtggcg ctttctcaat gctcacgctg   5040
taggtatctc agttcggtgt aggtcgttcg ctccaagctg ggctgtgtgc acgaacccc   5100 cgttcagccc gaccgctgcg ccttatccgg taactatcgt cttgagtcca acccggtaag   5160
acacgactta tcgccactgg cagcagccac tggtaacagg attagcagag cgaggtatgt   5220
aggcggtgct acagagttct tgaagtggtg gcctaactac ggctacacta gaaggacagt   5280
atttggtatc tgcgctctgc tgaagccagt taccttcgga aaaagagttg gtagctcttg   5340
atccggcaaa caaaccaccg ctggtagcgg tggttttttt gtttgcaagc agcagattac   5400
gcgcagaaaa aaaggatctc aagaagatcc tttgatcttt tctacggggt ctgacgctca   5460
gtggaacgaa aactcacgtt aagggatttt ggtcatgaga ttatcaaaaa ggatcttcac   5520
ctagatcctt ttaaattaaa aatgaagttt taaatcaatc taaagtatat atgagtaaac   5580
ttggtctgac agttaccaat gcttaatcag tgaggcacct atctcagcga tctgtctatt   5640
tcgttcatcc atagttgcct gactccgggg ggggggggcg ctgaggtctg cctcgtgaag   5700
aaggtgttgc tgactcatac caggcctgaa tcgccccatc atccagccag aaagtgaggg   5760
agccacggtt gatgagagct ttgttgtagg tggaccagtt ggtgattttg aacttttgct   5820
ttgccacgga acggtctgcg ttgtcgggaa gatgcgtgat ctgatccttc aactcagcaa   5880
aagttcgatt tattcaacaa agccgccgtc ccgtcaagtc agcgtaatgc tctgccagtg   5940
ttacaaccaa ttaaccaatt ctgattagaa aaactcatcg agcatcaaat gaaactgcaa   6000
tttattcata tcaggattat caataccata tttttgaaaa agccgtttct gtaatgaagg   6060
agaaaactca ccgaggcagt tccataggat ggcaagatcc tggtatcggt ctgcgattcc   6120
gactcgtcca acatcaatac aacctattaa tttcccctcg tcaaaaataa ggttatcaag   6180
```

-continued

```
tgagaaatca ccatgagtga cgactgaatc cggtgagaat ggcaaaagct tatgcatttc    6240
tttccagact tgttcaacag gccagccatt acgctcgtca tcaaaatcac tcgcatcaac    6300
caaaccgtta ttcattcgtg attgcgcctg agcgagacga aatacgcgat cgctgttaaa    6360
aggacaatta caaacaggaa tcgaatgcaa ccggcgcagg aacactgcca gcgcatcaac    6420
aatattttca cctgaatcag gatattcttc taatacctgg aatgctgttt tcccgggggat   6480 cgcagtggtg agtaaccatg catcatcagg agtacggata aaatgcttga tggtcggaag    6540
aggcataaat tccgtcagcc agtttagtct gaccatctca tctgtaacat cattggcaac    6600
gctacctttg ccatgtttca gaaacaactc tggcgcatcg ggcttcccat acaatcgata    6660
gattgtcgca cctgattgcc cgacattatc gcgagcccat ttatacccat ataaatcagc    6720
atccatgttg gaatttaatc gcggcctcga gcaagacgtt tcccgttgaa tatggctcat    6780
aacacccctt gtattactgt ttatgtaagc agacagtttt attgttcatg atgatatatt    6840
tttatcttgt gcaatgtaac atcagagatt ttgagacaca acgtggcttt cccccccccc    6900
ccattattga agcatttatc agggttattg tctcatgagc ggatacatat ttgaatgtat    6960
ttagaaaaat aaacaaatag gggttccgcg cacatttccc cgaaaagtgc cacctgacgt    7020
ctaagaaacc attattatca tgacattaac ctataaaaat aggcgtatca cgaggccctt    7080
tcgtc                                                                7085
```

```
<210> SEQ ID NO 41
<211> LENGTH: 1941
<212> TYPE: DNA
<213> ORGANISM: Artificial Sequence
<220> FEATURE:
<223> OTHER INFORMATION: BArr 6B - coding sequence
<220> FEATURE:
<221> NAME/KEY: misc_feature
<222> LOCATION: (1)..(441)
<223> OTHER INFORMATION: mNeonGreen Part 1
<220> FEATURE:
<221> NAME/KEY: misc_feature
<222> LOCATION: (442)..(453)
<223> OTHER INFORMATION: N-terminal linker
<220> FEATURE:
<221> NAME/KEY: misc_feature
<222> LOCATION: (451)..(1674)
<223> OTHER INFORMATION: B-arrestin
<220> FEATURE:
<221> NAME/KEY: misc_feature
<222> LOCATION: (1675)..(1680)
<223> OTHER INFORMATION: C-Terminal linker
<220> FEATURE:
<221> NAME/KEY: misc_feature
<222> LOCATION: (1681)..(1941)
<223> OTHER INFORMATION: mNeonGreen Part 2

<400> SEQUENCE: 41
```

```
atggtgagca agggcgagga ggataacatg gcctctctcc cagcgacaca tgagttacac     60
atctttggct ccatcaacgg tgtggacttt gacatggtgg tcagggcac cggcaatcca     120 aatgatggtt atgaggagtt aaacctgaag tccaccaagg gtgacctcca gttctccccc    180
tggattctgg tccctcatat cgggtatggc ttccatcagt acctgcccta ccctgacggg    240
atgtcgcctt ccaggccgc catggtagat ggctccggat accaagtcca tcgcacaatg    300
cagtttgaag atggtgcctc ccttactgtt aactaccgct acacctacga gggaagccac    360
atcaaaggag aggcccaggt gaagggact ggtttccctg ctgacggtcc tgtgatgacc    420
aactcgctga ccgctgcgga ctgcgacatc ggggagaaac ccgggaccag ggtcttcaag    480
aagtcgagcc ctaactgcaa gctcaccgtg tacttgggca gcgggactt cgtagatcac    540
```

```
ctggacaaag tggaccctgt agatggcgtg gtgcttgtgg accctgacta cctgaaggac      600
cgcaaagtgt ttgtgaccct cacctgcgcc ttccgctatg gccgtgaaga cctggatgtg      660
ctgggcttgt ccttccgcaa agacctgttc atcgccacct accaggcctt ccccccggtg      720
cccaacccac cccggccccc cacccgcctg caggaccggc tgctgaggaa gctgggccag      780
catgcccacc ccttcttctt caccataccc cagaatcttc atgctccgt cacactgcag       840 ccaggcccag aggatacagg aaaggcctgc ggcgtagact ttgagattcg agccttctgt      900
gctaaatcac tagaagagaa aagccacaaa aggaactctg tgcggctggt gatccgaaag      960
gtgcagttcg ccccggagaa acccggcccc cagccttcag ccgaaaccac acgccacttc     1020
ctcatgtctg accggtccct gcacctcgag gcttcctgg acaaggagct gtactaccat      1080
ggggagcccc tcaatgtaaa tgtccacgtc accaacaact ccaccaagac cgtcaagaag     1140
atcaaagtct ctgtgagaca gtacgccgac atctgcctct tcagcaccgc ccagtacaag     1200
tgtcctgtgg ctcaactcga acaagatgac caggtatctc ccagctccac attctgtaag     1260
gtgtacacca taaccccact gctcagcgac aaccgggaga agcggggtct cgccctggat     1320
gggaaactca agcacgagga caccaacctg gcttccagca ccatcgtgaa ggagggtgcc     1380
aacaaggagg tgctgggaat cctggtgtcc tacagggtca aggtgaagct ggtggtgtct     1440
cgaggcgggg atgtctctgt ggagctgcct tttgttctta tgcaccccaa gccccacgac     1500
cacatccccc tccccagacc ccagtcagcc gctccggaga cagatgtccc tgtggacacc     1560
aacctcattg aatttgatac caactatgcc acagatgatg acattgtgtt tgaggacttt     1620
gcccggcttc ggctgaaggg gatgaaggat gacgactatg atgatcaact ctgcaatgtt     1680
tcgaagaaga cttaccccaa cgacaaaacc atcatcagta cctttaagtg gagttacacc     1740
actggaaatg gcaagcgcta ccggagcact gcgcggacca cctacacctt tgccaagcca     1800
atggcggcta actatctgaa gaaccagccg atgtacgtgt ccgtaagac ggagctcaag      1860 cactccaaga ccgagctcaa cttcaaggag tggcaaaagg cctttaccga tgtgatgggc     1920
atggacgagc tgtacaagta g                                              1941
```

<210> SEQ ID NO 42
<211> LENGTH: 646
<212> TYPE: PRT
<213> ORGANISM: Artificial Sequence
<220> FEATURE:
<223> OTHER INFORMATION: BArr 6B - coding sequence
<220> FEATURE:
<221> NAME/KEY: SITE
<222> LOCATION: (1)..(147)
<223> OTHER INFORMATION: mNeonGreen Part 1
<220> FEATURE:
<221> NAME/KEY: SITE
<222> LOCATION: (148)..(151)
<223> OTHER INFORMATION: N-terminal linker
<220> FEATURE:
<221> NAME/KEY: SITE
<222> LOCATION: (151)..(558)
<223> OTHER INFORMATION: B-arrestin
<220> FEATURE:
<221> NAME/KEY: SITE
<222> LOCATION: (559)..(560)
<223> OTHER INFORMATION: C-terminal linker
<220> FEATURE:
<221> NAME/KEY: SITE
<222> LOCATION: (561)..(646)
<223> OTHER INFORMATION: mNeonGreen Part 2

<400> SEQUENCE: 42

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
            115                 120                 125

Gly Thr Gly Phe Pro Ala Asp Gly Pro Val Met Thr Asn Ser Leu Thr
            130                 135                 140

Ala Ala Asp Cys Asp Ile Gly Glu Lys Pro Gly Thr Arg Val Phe Lys
145                 150                 155                 160

Lys Ser Ser Pro Asn Cys Lys Leu Thr Val Tyr Leu Gly Lys Arg Asp
                165                 170                 175

Phe Val Asp His Leu Asp Lys Val Asp Pro Val Asp Gly Val Val Leu
            180                 185                 190

Val Asp Pro Asp Tyr Leu Lys Asp Arg Lys Val Phe Val Thr Leu Thr
            195                 200                 205

Cys Ala Phe Arg Tyr Gly Arg Glu Asp Leu Asp Val Leu Gly Leu Ser
    210                 215                 220

Phe Arg Lys Asp Leu Phe Ile Ala Thr Tyr Gln Ala Phe Pro Pro Val
225                 230                 235                 240

Pro Asn Pro Pro Arg Pro Pro Thr Arg Leu Gln Asp Arg Leu Leu Arg
                245                 250                 255

Lys Leu Gly Gln His Ala His Pro Phe Phe Phe Thr Ile Pro Gln Asn
            260                 265                 270

Leu Pro Cys Ser Val Thr Leu Gln Pro Gly Pro Glu Asp Thr Gly Lys
            275                 280                 285

Ala Cys Gly Val Asp Phe Glu Ile Arg Ala Phe Cys Ala Lys Ser Leu
    290                 295                 300

Glu Glu Lys Ser His Lys Arg Asn Ser Val Arg Leu Val Ile Arg Lys
305                 310                 315                 320

Val Gln Phe Ala Pro Glu Lys Pro Gly Pro Gln Pro Ser Ala Glu Thr
                325                 330                 335

Thr Arg His Phe Leu Met Ser Asp Arg Ser Leu His Leu Glu Ala Ser
            340                 345                 350

Leu Asp Lys Glu Leu Tyr Tyr His Gly Glu Pro Leu Asn Val Asn Val
            355                 360                 365

His Val Thr Asn Asn Ser Thr Lys Thr Val Lys Lys Ile Lys Val Ser
            370                 375                 380

Val Arg Gln Tyr Ala Asp Ile Cys Leu Phe Ser Thr Ala Gln Tyr Lys
385                 390                 395                 400

Cys Pro Val Ala Gln Leu Glu Gln Asp Asp Gln Val Ser Pro Ser Ser
                405                 410                 415

Thr Phe Cys Lys Val Tyr Thr Ile Thr Pro Leu Leu Ser Asp Asn Arg
```

-continued

```
           420              425              430

Glu Lys Arg Gly Leu Ala Leu Asp Gly Lys Leu Lys His Glu Asp Thr
         435                  440                  445

Asn Leu Ala Ser Ser Thr Ile Val Lys Glu Gly Ala Asn Lys Glu Val
     450                  455                  460

Leu Gly Ile Leu Val Ser Tyr Arg Val Lys Val Lys Leu Val Val Ser
465                  470                  475                  480

Arg Gly Gly Asp Val Ser Val Glu Leu Pro Phe Val Leu Met His Pro
                 485                  490                  495

Lys Pro His Asp His Ile Pro Leu Pro Arg Pro Gln Ser Ala Ala Pro
             500                  505                  510

Glu Thr Asp Val Pro Val Asp Thr Asn Leu Ile Glu Phe Asp Thr Asn
         515                  520                  525

Tyr Ala Thr Asp Asp Asp Ile Val Phe Glu Asp Phe Ala Arg Leu Arg
     530                  535                  540

Leu Lys Gly Met Lys Asp Asp Asp Tyr Asp Asp Gln Leu Cys Asn Val
545                  550                  555                  560

Ser Lys Lys Thr Tyr Pro Asn Asp Lys Thr Ile Ile Ser Thr Phe Lys
                 565                  570                  575

Trp Ser Tyr Thr Thr Gly Asn Gly Lys Arg Tyr Arg Ser Thr Ala Arg
             580                  585                  590

Thr Thr Tyr Thr Phe Ala Lys Pro Met Ala Ala Asn Tyr Leu Lys Asn
         595                  600                  605

Gln Pro Met Tyr Val Phe Arg Lys Thr Glu Leu Lys His Ser Lys Thr
     610                  615                  620

Glu Leu Asn Phe Lys Glu Trp Gln Lys Ala Phe Thr Asp Val Met Gly
625                  630                  635                  640

Met Asp Glu Leu Tyr Lys
                 645
```

<210> SEQ ID NO 43
<211> LENGTH: 441
<212> TYPE: DNA
<213> ORGANISM: Artificial Sequence
<220> FEATURE:
<223> OTHER INFORMATION: BArr 6B - mNeonGreen Part 1
<220> FEATURE:
<221> NAME/KEY: misc_feature
<222> LOCATION: (1)..(441)
<223> OTHER INFORMATION: mNeonGreen Part 1

<400> SEQUENCE: 43

```
atggtgagca agggcgagga ggataacatg gcctctctcc cagcgacaca tgagttacac      60
atctttggct ccatcaacgg tgtggacttt gacatggtgg gtcagggcac cggcaatcca     120
aatgatggtt atgaggagtt aaacctgaag tccaccaagg gtgacctcca gttctccccc     180
tggattctgg tccctcatat cgggtatggc ttccatcagt acctgcccta ccctgacggg     240
atgtcgcctt ccaggccgc catggtagat ggctccggat accaagtcca tcgcacaatg     300
cagtttgaag atggtgcctc ccttactgtt aactaccgct acacctacga gggaagccac     360
atcaaaggag aggcccaggt gaagggggact ggtttccctg ctgacggtcc tgtgatgacc     420
aactcgctga ccgctgcgga c                                              441
```

<210> SEQ ID NO 44
<211> LENGTH: 147
<212> TYPE: PRT
<213> ORGANISM: Artificial Sequence

```
<220> FEATURE:
<223> OTHER INFORMATION: BArr 6B - mNeonGreen Part 1
<220> FEATURE:
<221> NAME/KEY: SITE
<222> LOCATION: (1)..(147)
<223> OTHER INFORMATION: mNeonGreen Part 1

<400> SEQUENCE: 44

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp
145

<210> SEQ ID NO 45
<211> LENGTH: 12
<212> TYPE: DNA
<213> ORGANISM: Artificial Sequence
<220> FEATURE:
<223> OTHER INFORMATION: BArr 6B - 1st linker sequence
<220> FEATURE:
<221> NAME/KEY: misc_feature
<222> LOCATION: (1)..(12)
<223> OTHER INFORMATION: N-Terminal linker

<400> SEQUENCE: 45
tgcgacatcg gg                                                          12

<210> SEQ ID NO 46
<211> LENGTH: 4
<212> TYPE: PRT
<213> ORGANISM: Artificial Sequence
<220> FEATURE:
<223> OTHER INFORMATION: BArr 6b - 1st Linker Sequence

<400> SEQUENCE: 46

Cys Asp Ile Gly
1

<210> SEQ ID NO 47
<211> LENGTH: 1224
<212> TYPE: DNA
<213> ORGANISM: Artificial Sequence
<220> FEATURE:
<223> OTHER INFORMATION: BArr 6B - Beta-arrestin-2
<220> FEATURE:
<221> NAME/KEY: misc_feature
<222> LOCATION: (1)..(1224)
<223> OTHER INFORMATION: B-arrestin
```

<400> SEQUENCE: 47
ggggagaaac ccgggaccag ggtcttcaag aagtcgagcc ctaactgcaa gctcaccgtg      60
tacttgggca agcgggactt cgtagatcac ctggacaaag tggaccctgt agatggcgtg     120
gtgcttgtgg accctgacta cctgaaggac cgcaaagtgt ttgtgaccct cacctgcgcc     180
ttccgctatg gccgtgaaga cctggatgtg ctgggcttgt ccttccgcaa agacctgttc     240
atcgccacct accaggcctt cccccccggtg cccaacccac cccggccccc cacccgcctg     300
caggaccggc tgctgaggaa gctgggccag catgcccacc ccttcttctt caccatacccc     360 cagaatcttc catgctccgt cacactgcag ccaggcccag aggatacagg aaaggcctgc     420
ggcgtagact ttgagattcg agccttctgt gctaaatcac tagaagagaa aagccacaaa     480
aggaactctg tgcggctggt gatccgaaag gtgcagttcg ccccggagaa acccggcccc     540
cagccttcag ccgaaaccac acgccacttc ctcatgtctg accggtccct gcacctcgag     600
gcttccctgg acaaggagct gtactaccat ggggagcccc tcaatgtaaa tgtccacgtc     660
accaacaact ccaccaagac cgtcaagaag atcaaagtct ctgtgagaca gtacgccgac     720
atctgcctct tcagcaccgc ccagtacaag tgtcctgtgg ctcaactcga acaagatgac     780
caggtatctc ccagctccac attctgtaag gtgtacacca taaccccact gctcagcgac     840
aaccgggaga agcgggggtct cgccctggat gggaaactca agcacgagga caccaacctg     900
gcttccagca ccatcgtgaa ggagggtgcc aacaaggagg tgctgggaat cctggtgtcc     960
tacagggtca aggtgaagct ggtggtgtct cgaggcgggg atgtctctgt ggagctgcct    1020
tttgttctta tgcaccccaa gccccacgac cacatccccc tccccagacc ccagtcagcc    1080
gctccggaga cagatgtccc tgtggacacc aacctcattg aatttgatac caactatgcc    1140
acagatgatg acattgtgtt tgaggacttt gcccggcttc ggctgaaggg gatgaaggat    1200
gacgactatg atgatcaact ctgc                                          1224

<210> SEQ ID NO 48
<211> LENGTH: 408
<212> TYPE: PRT
<213> ORGANISM: Artificial Sequence
<220> FEATURE:
<223> OTHER INFORMATION: BArr 6B - Beta-arrestin-2
<220> FEATURE:
<221> NAME/KEY: SITE
<222> LOCATION: (1)..(408)
<223> OTHER INFORMATION: B-arrestin

<400> SEQUENCE: 48

Gly Glu Lys Pro Gly Thr Arg Val Phe Lys Lys Ser Ser Pro Asn Cys
1               5                   10                  15

Lys Leu Thr Val Tyr Leu Gly Lys Arg Asp Phe Val Asp His Leu Asp
            20                  25                  30

Lys Val Asp Pro Val Asp Gly Val Val Leu Val Asp Pro Asp Tyr Leu
        35                  40                  45

Lys Asp Arg Lys Val Phe Val Thr Leu Thr Cys Ala Phe Arg Tyr Gly
    50                  55                  60

Arg Glu Asp Leu Asp Val Leu Gly Leu Ser Phe Arg Lys Asp Leu Phe
65                  70                  75                  80

Ile Ala Thr Tyr Gln Ala Phe Pro Pro Val Pro Asn Pro Pro Arg Pro
                85                  90                  95

Pro Thr Arg Leu Gln Asp Arg Leu Leu Arg Lys Leu Gly Gln His Ala
            100                 105                 110

-continued

```
His Pro Phe Phe Phe Thr Ile Pro Gln Asn Leu Pro Cys Ser Val Thr
        115             120             125

Leu Gln Pro Gly Pro Glu Asp Thr Gly Lys Ala Cys Gly Val Asp Phe
    130             135             140

Glu Ile Arg Ala Phe Cys Ala Lys Ser Leu Glu Glu Lys Ser His Lys
145             150             155             160

Arg Asn Ser Val Arg Leu Val Ile Arg Lys Val Gln Phe Ala Pro Glu
            165             170             175

Lys Pro Gly Pro Gln Pro Ser Ala Glu Thr Thr Arg His Phe Leu Met
            180             185             190

Ser Asp Arg Ser Leu His Leu Glu Ala Ser Leu Asp Lys Glu Leu Tyr
            195             200             205

Tyr His Gly Glu Pro Leu Asn Val Asn Val His Val Thr Asn Asn Ser
    210             215             220

Thr Lys Thr Val Lys Lys Ile Lys Val Ser Val Arg Gln Tyr Ala Asp
225             230             235             240

Ile Cys Leu Phe Ser Thr Ala Gln Tyr Lys Cys Pro Val Ala Gln Leu
            245             250             255

Glu Gln Asp Asp Gln Val Ser Pro Ser Ser Thr Phe Cys Lys Val Tyr
            260             265             270

Thr Ile Thr Pro Leu Leu Ser Asp Asn Arg Glu Lys Arg Gly Leu Ala
            275             280             285

Leu Asp Gly Lys Leu Lys His Glu Asp Thr Asn Leu Ala Ser Ser Thr
    290             295             300

Ile Val Lys Glu Gly Ala Asn Lys Glu Val Leu Gly Ile Leu Val Ser
305             310             315             320

Tyr Arg Val Lys Val Lys Leu Val Val Ser Arg Gly Gly Asp Val Ser
            325             330             335

Val Glu Leu Pro Phe Val Leu Met His Pro Lys Pro His Asp His Ile
            340             345             350

Pro Leu Pro Arg Pro Gln Ser Ala Ala Pro Glu Thr Asp Val Pro Val
    355             360             365

Asp Thr Asn Leu Ile Glu Phe Asp Thr Asn Tyr Ala Thr Asp Asp Asp
    370             375             380

Ile Val Phe Glu Asp Phe Ala Arg Leu Arg Leu Lys Gly Met Lys Asp
385             390             395             400

Asp Asp Tyr Asp Asp Gln Leu Cys
            405
```

```
<210> SEQ ID NO 49
<211> LENGTH: 261
<212> TYPE: DNA
<213> ORGANISM: Artificial Sequence
<220> FEATURE:
<223> OTHER INFORMATION: BArr 6B - mNeonGreen Part 2
<220> FEATURE:
<221> NAME/KEY: misc_feature
<222> LOCATION: (1)..(261)
<223> OTHER INFORMATION: mNeonGreen Part 2

<400> SEQUENCE: 49
tcgaagaaga cttaccccaa cgacaaaacc atcatcagta cctttaagtg gagttacacc        60
actggaaatg gcaagcgcta ccggagcact gcgcggacca cctacacctt tgccaagcca       120
atggcggcta actatctgaa gaaccagccg atgtacgtgt ccgtaagac ggagctcaag       180 cactccaaga ccgagctcaa cttcaaggag tggcaaaagg cctttaccga tgtgatgggc       240
```

-continued atggacgagc tgtacaagta g                                                        261

<210> SEQ ID NO 50
<211> LENGTH: 86
<212> TYPE: PRT
<213> ORGANISM: Artificial Sequence
<220> FEATURE:
<223> OTHER INFORMATION: BArr 6B - mNeonGreen Part 2
<220> FEATURE:
<221> NAME/KEY: SITE
<222> LOCATION: (1)..(86)
<223> OTHER INFORMATION: mNeonGreen Part 2

<400> SEQUENCE: 50

Ser Lys Lys Thr Tyr Pro Asn Asp Lys Thr Ile Ile Ser Thr Phe Lys
1               5                   10                  15

Trp Ser Tyr Thr Thr Gly Asn Gly Lys Arg Tyr Arg Ser Thr Ala Arg
            20                  25                  30

Thr Thr Tyr Thr Phe Ala Lys Pro Met Ala Ala Asn Tyr Leu Lys Asn
        35                  40                  45

Gln Pro Met Tyr Val Phe Arg Lys Thr Glu Leu Lys His Ser Lys Thr
    50                  55                  60

Glu Leu Asn Phe Lys Glu Trp Gln Lys Ala Phe Thr Asp Val Met Gly
65                  70                  75                  80

Met Asp Glu Leu Tyr Lys
                85

<210> SEQ ID NO 51
<211> LENGTH: 7094
<212> TYPE: DNA
<213> ORGANISM: Artificial Sequence
<220> FEATURE:
<223> OTHER INFORMATION: BArr L1-3B8 - plasmid
<220> FEATURE:
<221> NAME/KEY: misc_feature
<222> LOCATION: (320)..(699)
<223> OTHER INFORMATION: CMV enhancer
<220> FEATURE:
<221> NAME/KEY: misc_feature
<222> LOCATION: (700)..(903)
<223> OTHER INFORMATION: CMV promoter
<220> FEATURE:
<221> NAME/KEY: misc_feature
<222> LOCATION: (1039)..(1864)
<223> OTHER INFORMATION: CMV Intron A
<220> FEATURE:
<221> NAME/KEY: misc_feature
<222> LOCATION: (1936)..(2385)
<223> OTHER INFORMATION: mNeonGreen
<220> FEATURE:
<221> NAME/KEY: misc_feature
<222> LOCATION: (1936)..(3885)
<223> OTHER INFORMATION: arrestin sensor BArrL1-3
<220> FEATURE:
<221> NAME/KEY: misc_feature
<222> LOCATION: (2386)..(2397)
<223> OTHER INFORMATION: N-terminal linker
<220> FEATURE:
<221> NAME/KEY: misc_feature
<222> LOCATION: (2395)..(3618)
<223> OTHER INFORMATION: B-arrestin
<220> FEATURE:
<221> NAME/KEY: misc_feature
<222> LOCATION: (3619)..(3624)
<223> OTHER INFORMATION: C-terminal linker
<220> FEATURE:
<221> NAME/KEY: misc_feature
<222> LOCATION: (3625)..(3885)
<223> OTHER INFORMATION: mNeonGreen Part 2
<220> FEATURE:

```
<221> NAME/KEY: misc_feature
<222> LOCATION: (3886)..(3900)
<223> OTHER INFORMATION: pUB/pKM1 joint
<220> FEATURE:
<221> NAME/KEY: misc_feature
<222> LOCATION: (3906)..(4248)
<223> OTHER INFORMATION: PolyA Terminator
<220> FEATURE:
<221> NAME/KEY: misc_feature
<222> LOCATION: (3906)..(4248)
<223> OTHER INFORMATION: bGH poly(A) signal
<220> FEATURE:
<221> NAME/KEY: misc_feature
<222> LOCATION: (4843)..(5431)
<223> OTHER INFORMATION: ori
<220> FEATURE:
<221> NAME/KEY: misc_feature
<222> LOCATION: (5974)..(6789)
<223> OTHER INFORMATION: KanR

<400> SEQUENCE: 51
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg       120 ttggcgggtg tcggggctgg cttaactatg cggcatcaga gcagattgta ctgagagtgc      180
accatatgcg ggtgaaatac cgcacagatg cgtaaggaga aaataccgca tcagattggc      240
tattggccat tgcatacgtt gtatccatat cataatatgt acatttatat tggctcatgt      300
ccaacattac cgccatgttg acattgatta ttgactagtt attaatagta atcaattacg      360
gggtcattag ttcatagccc atatatggag ttccgcgtta cataacttac ggtaaatggc      420
ccgcctggct gaccgcccaa cgacccccgc ccattgacgt caataatgac gtatgttccc      480
atagtaacgc caatagggac tttccattga cgtcaatggg tggagtattt acggtaaact      540
gcccacttgg cagtacatca agtgtatcat atgccaagta cgcccccctat tgacgtcaat      600 gacggtaaat ggcccgcctg gcattatgcc cagtacatga ccttatggga ctttcctact      660
tggcagtaca tctacgtatt agtcatcgct attaccatgg tgatgcggtt ttggcagtac      720
atcaatgggc gtggatagcg gtttgactca cggggatttc caagtctcca ccccattgac      780
gtcaatggga gtttgttttg gcaccaaaat caacgggact ttccaaaatg tcgtaacaac      840
tccgccccat tgacgcaaat gggcggtagg cgtgtacggt gggaggtcta tataagcaga      900
gctcgtttag tgaaccgtca gatcgcctgg agacgccatc cacgctgttt tgacctccat      960
agaagacacc gggaccgatc cagcctccgc ggccgggaac ggtgcattgg aacgcggatt      1020
ccccgtgcca agagtgacgt aagtaccgcc tatagactct ataggcacac ccctttggct      1080
cttatgcatg ctatactgtt tttggcttgg ggcctataca ccccgcttc cttatgctat       1140 aggtgatggt atagcttagc ctataggtgt gggttattga ccattattga ccactcccct      1200
attggtgacg atactttcca ttactaatcc ataacatggc tctttgccac aactatctct      1260
attggctata tgccaatact ctgtccttca gagactgaca cggactctgt atttttacag      1320 gatgggtcc catttattat ttacaaattc acatatacaa caacgccgtc ccccgtgccc       1380
gcagttttta ttaaacatag cgtgggatct ccacgcgaat ctcgggtacg tgttccggac      1440
atgggctctt ctccggtagc ggcggagctt ccacatccga ccctggtcc catgcctcca       1500 gcggctcatg gtcgctcggc agctccttgc tcctaacagt ggaggccaga cttaggcaca      1560
gcacaatgcc caccaccacc agtgtgccgc acaaggccgt ggcggtaggg tatgtgtctg      1620
aaaatgagcg tggagattgg gctcgcacgg ctgacgcaga tggaagactt aaggcagcgg      1680
cagaagaaga tgcaggcagc tgagttgttg tattctgata agagtcagag gtaactcccg      1740
```

-continued

```
ttgcggtgct gttaacggtg gagggcagtg tagtctgagc agtactcgtt gctgccgcgc    1800
gcgccaccag acataatagc tgacagacta acagactgtt cctttccatg ggtcttttct    1860
gcagtcaccg tcgtcgacac gtgtgatcag atatacgact cactataggg agacccaagc    1920
tggctagcgt ttaccatggt gagcaagggc gaggaggata acatggcctc tctcccagcg    1980
acacatgagt tacacatctt tggctccatc aacggtgtgg actttgacat ggtgggtcag    2040
ggcaccggca atccaaatga tggttatgag gagttaaacc tgaagtccac caagggtgac    2100
ctccagttct cccctggat tctggtccct catatcgggt atggcttcca tcagtacctg    2160
ccctaccctg acgggatgtc gccttttcag gccgccatgg tagatggctc cggataccaa    2220
gtccatcgca caatgcagtt tgaagatggt gcctccctta ctgttaacta ccgctacacc    2280
tacgagggaa gccacatcaa aggagaggcc caggtgaagg ggactggttt ccctgctgac    2340
ggtcctgtga tgaccaactc gctgaccgct gcggactggt gcaggatcct ttggggggag    2400
aaacccggga ccaggtcttc aagaagtcg agccctaact gcaagctcac cgtgtacttg    2460
ggcaagcggg acttcgtaga tcacctggac aaagtggacc ctgtagatgg cgtggtgctt    2520
gtggaccctg actacctgaa ggaccgcaaa gtgtttgtga ccctcacctg cgccttccgc    2580
tatggccgtg aagacctgga tgtgctgggc ttgtccttcc gcaaagacct gttcatcgcc    2640
acctaccagg cctccccccc ggtgcccaac ccaccccggc cccccacccg cctgcaggac    2700
cggctgctga ggaagctggg ccagcatgcc caccccttct tcttcaccat accccagaat    2760
cttccatgct ccgtcacact gcagccaggc ccagaggata caggaaaggc ctgcggcgta    2820
gactttgaga ttcgagcctt ctgtgctaaa tcactagaag agaaaagcca caaaggaac     2880 tctgtgcggc tggtgatccg aaaggtgcag ttcgccccgg agaaacccgg cccccagcct    2940
tcagccgaaa ccacacgcca cttcctcatg tctgaccggt ccctgcacct cgaggcttcc    3000
ctggacaagg agctgtacta ccatgggag cccctcaatg taaatgtcca cgtcaccaac     3060
aactccacca agaccgtcaa gaagatcaaa gtctctgtga gacagtacgc cgacatctgc    3120
ctcttcagca ccgcccagta caagtgtcct gtggctcaac tcgaacaaga tgaccaggta    3180
tctcccagct ccacattctg taaggtgtac accataaccc cactgctcag cgacaaccgg    3240
gagaagcggg gtctcgccct ggatgggaaa ctcaagcacg aggacaccaa cctggcttcc    3300
agcaccatcg tgaaggaggg tgccaacaag gaggtgctgg gaatcctggt gtcctacagg    3360
gtcaaggtga agctggtggt gtctcgaggc ggggatgtct ctgtggagct gccttttgtt    3420
cttatgcacc ccaagccca cgaccacatc ccctccccca gacccagtc agccgctccg      3480 gagacagatg tccctgtgga caccaacctc attgaatttg ataccaacta tgccacagat    3540
gatgacattg tgtttgagga ctttgcccgg cttcggctga aggggatgaa ggatgacgac    3600
tatgatgatc aactctgcaa tgtttcgaag aagacttacc ccaacgacaa aaccatcatc    3660 agtacctta agtggagtta caccactgga aatggcaagc gctaccggag cactgcgcgg     3720
accacctaca cctttgccaa gccaatggcg gctaactatc tgaagaacca gccgatgtac    3780
gtgttccgta agacggagct caagcactcc aagaccgagc tcaacttcaa ggagtggcaa    3840
aaggccttta ccgatgtgat gggcatggac gagctgtaca agtagcgcgc cctcgactgt    3900
gccttctagt tgccagccat ctgtatcgcg gccgctctag accaggcgcc tggatccaga    3960
tcacttctgg ctaataaaag atcagagctc tagagatctg tgtgttggtt ttttgtggat    4020
ctgctgtgcc ttctagttgc cagccatctg ttgtttgccc ctcccccgtg ccttccttga    4080
```

```
ccctggaagg tgccactccc actgtccttt cctaataaaa tgaggaaatt gcatcgcatt    4140
gtctgagtag gtgtcattct attctggggg gtggggtggg gcagcacagc aaggggggagg    4200 attgggaaga caatagcagg catgctgggg atgcggtggg ctctatgggt acctctctct    4260
ctctctctct ctctctctct ctctctctct ctcggtacct ctctctctct ctctctctct    4320
ctctctctct ctctctctcg gtaccaggtg ctgaagaatt gacccggttc ctcctgggcc    4380
agaaagaagc aggcacatcc ccttctctgt gacacaccct gtccacgccc ctggttctta    4440
gttccagccc cactcatagg acactcatag ctcaggaggg ctccgccttc aatcccaccc    4500
gctaaagtac ttggagcggt ctctccctcc ctcatcagcc caccaaacca aacctagcct    4560
ccaagagtgg gaagaaatta aagcaagata ggctattaag tgcagaggga gagaaaatgc    4620
ctccaacatg tgaggaagta atgagagaaa tcatagaatt tcttccgctt cctcgctcac    4680
tgactcgctg cgctcggtcg ttcggctgcg gcgagcggta tcagctcact caaaggcggt    4740
aatacggtta tccacagaat caggggataa cgcaggaaag aacatgtgag caaaaggcca    4800
gcaaaaggcc aggaaccgta aaaaggccgc gttgctggcg tttttccata ggctccgccc    4860
ccctgacgag catcacaaaa atcgacgctc aagtcagagg tggcgaaacc cgacaggact    4920
ataaagatac caggcgtttc cccctggaag ctccctcgtg cgctctcctg ttccgacccct    4980 gccgcttacc ggatacctgt ccgcctttct cccttcggga agcgtggcgc tttctcaatg    5040
ctcacgctgt aggtatctca gttcggtgta ggtcgttcgc tccaagctgg gctgtgtgca    5100 cgaaccccccc gttcagcccg accgctgcgc cttatccggt aactatcgtc ttgagtccaa    5160
cccggtaaga cacgacttat cgccactggc agcagccact ggtaacagga ttagcagagc    5220
gaggtatgta ggcggtgcta cagagttctt gaagtggtgg cctaactacg gctacactag    5280
aaggacagta tttggtatct gcgctctgct gaagccagtt accttcggaa aaagagttgg    5340
tagctcttga tccggcaaac aaaccaccgc tggtagcggt ggtttttttg tttgcaagca    5400
gcagattacg cgcagaaaaa aaggatctca agaagatcct ttgatctttt ctacggggtc    5460
tgacgctcag tggaacgaaa actcacgtta agggattttg gtcatgagat tatcaaaaag    5520
gatcttcacc tagatccttt taaattaaaa atgaagtttt aaatcaatct aaagtatata    5580
tgagtaaact tggtctgaca gttaccaatg cttaatcagt gaggcaccta tctcagcgat    5640
ctgtctattt cgttcatcca tagttgcctg actccggggg ggggggcgc tgaggtctgc    5700 ctcgtgaaga aggtgttgct gactcatacc aggcctgaat cgccccatca tccagccaga    5760
aagtgaggga gccacggttg atgagagctt tgttgtaggt ggaccagttg gtgattttga    5820
acttttgctt tgccacggaa cggtctgcgt tgtcgggaag atgcgtgatc tgatccttca    5880
actcagcaaa agttcgattt attcaacaaa gccgccgtcc cgtcaagtca gcgtaatgct    5940
ctgccagtgt tacaaccaat taaccaattc tgattagaaa aactcatcga gcatcaaatg    6000
aaactgcaat ttattcatat caggattatc aataccatat ttttgaaaaa gccgtttctg    6060
taatgaagga gaaaactcac cgaggcagtt ccataggatg gcaagatcct ggtatcggtc    6120
tgcgattccg actcgtccaa catcaataca acctattaat ttcccctcgt caaaaataag    6180
gttatcaagt gagaaatcac catgagtgac gactgaatcc ggtgagaatg gcaaaagctt    6240
atgcatttct ttccagactt gttcaacagg ccagccatta cgctcgtcat caaaatcact    6300
cgcatcaacc aaaccgttat tcattcgtga ttgcgcctga gcgagacgaa atacgcgatc    6360
gctgttaaaa ggacaattac aaacaggaat cgaatgcaac cggcgcagga acactgccag    6420
cgcatcaaca atattttcac ctgaatcagg atattcttct aatacctgga atgctgtttt    6480
```

```
cccgggggatc gcagtggtga gtaaccatgc atcatcagga gtacggataa aatgcttgat       6540
ggtcggaaga ggcataaatt ccgtcagcca gtttagtctg accatctcat ctgtaacatc       6600
attggcaacg ctacctttgc catgtttcag aaacaactct ggcgcatcgg gcttcccata       6660
caatcgatag attgtcgcac ctgattgccc gacattatcg cgagcccatt tatacccata       6720
taaatcagca tccatgttgg aatttaatcg cggcctcgag caagacgttt cccgttgaat       6780
atggctcata acacccccttg tattactgtt tatgtaagca gacagtttta ttgttcatga       6840
tgatatattt ttatcttgtg caatgtaaca tcagagattt tgagacacaa cgtggctttc       6900 ccccccccc cattattgaa gcattatca gggttattgt ctcatgagcg gatacatatt         6960
tgaatgtatt tagaaaaata aacaaatagg ggttccgcgc acatttcccc gaaaagtgcc       7020
acctgacgtc taagaaacca ttattatcat gacattaacc tataaaaata ggcgtatcac       7080 gaggccctttt cgtc                                                          7094
```

```
<210> SEQ ID NO 52
<211> LENGTH: 1950
<212> TYPE: DNA
<213> ORGANISM: Artificial Sequence
<220> FEATURE:
<223> OTHER INFORMATION: BArr L1-3B8 - coding sequence
<220> FEATURE:
<221> NAME/KEY: misc_feature
<222> LOCATION: (1)..(450)
<223> OTHER INFORMATION: mNeonGreen Part 1
<220> FEATURE:
<221> NAME/KEY: misc_feature
<222> LOCATION: (451)..(462)
<223> OTHER INFORMATION: N-terminal linker
<220> FEATURE:
<221> NAME/KEY: misc_feature
<222> LOCATION: (460)..(1683)
<223> OTHER INFORMATION: B-arrestin
<220> FEATURE:
<221> NAME/KEY: misc_feature
<222> LOCATION: (1684)..(1689)
<223> OTHER INFORMATION: C-Terminal linker
<220> FEATURE:
<221> NAME/KEY: misc_feature
<222> LOCATION: (1690)..(1950)
<223> OTHER INFORMATION: mNeonGreen Part 2

<400> SEQUENCE: 52
```

```
atggtgagca agggcgagga ggataacatg gcctctctcc cagcgacaca tgagttacac        60
atctttggct ccatcaacgg tgtggacttt gacatggtgg gtcagggcac cggcaatcca       120
aatgatggtt atgaggagtt aaacctgaag tccaccaagg gtgacctcca gttctccccc       180
tggattctgg tccctcatat cgggtatggc ttccatcagt acctgcccta ccctgacggg       240
atgtcgcctt ccaggccgc catggtagat ggctccggat accaagtcca tcgcacaatg        300
cagtttgaag atggtgcctc ccttactgtt aactaccgct acacctacga gggaagccac       360
atcaaaggag aggcccaggt gaaggggact ggtttccctg ctgacggtcc tgtgatgacc       420
aactcgctga ccgctgcgga ctggtgcagg atcctttggg gggagaaacc cgggaccagg       480
gtcttcaaga agtcgagccc taactgcaag ctcaccgtgt acttgggcaa gcgggacttc       540
gtagatcacc tggacaaagt ggaccctgta gatggcgtgg tgcttgtgga ccctgactac       600
ctgaaggacc gcaaagtgtt tgtgaccctc acctgcgcct ccgctatgg ccgtgaagac        660 ctggatgtgc tgggcttgtc cttccgcaaa gacctgttca tcgccaccta ccaggccttc       720 ccccccggtgc ccaacccacc ccggcccccc accccgcctgc aggaccggct gctgaggaag       780
```

-continued

```
ctgggccagc atgcccaccc cttcttcttc accataccccc agaatcttcc atgctccgtc      840
acactgcagc caggcccaga ggatacagga aaggcctgcg gcgtagactt tgagattcga      900
gccttctgtg ctaaatcact agaagagaaa agccacaaaa ggaactctgt gcggctggtg      960
atccgaaagg tgcagttcgc cccggagaaa cccggcccccc agccttcagc cgaaaccaca    1020
cgccacttcc tcatgtctga ccggtccctg cacctcgagg cttccctgga caaggagctg    1080
tactaccatg gggagcccct caatgtaaat gtccacgtca ccaacaactc caccaagacc    1140
gtcaagaaga tcaaagtctc tgtgagacag tacgccgaca tctgcctctt cagcaccgcc    1200
cagtacaagt gtcctgtggc tcaactcgaa caagatgacc aggtatctcc cagctccaca    1260
ttctgtaagg tgtacaccat aaccccactg ctcagcgaca accgggagaa gcggggtctc    1320
gccctggatg ggaaactcaa gcacgaggac accaacctgg cttccagcac catcgtgaag    1380
gagggtgcca acaaggaggt gctgggaatc ctggtgtcct acagggtcaa ggtgaagctg    1440
gtggtgtctc gaggcgggga tgtctctgtg gagctgcctt ttgttcttat gcaccccaag    1500
ccccacgacc acatccccct ccccagaccc cagtcagccg ctccggagac agatgtccct    1560
gtggacacca acctcattga atttgatacc aactatgcca cagatgatga cattgtgttt    1620
gaggactttg cccggcttcg gctgaagggg atgaaggatg acgactatga tgatcaactc    1680
tgcaatgttt cgaagaagac ttaccccaac gacaaaacca tcatcagtac ctttaagtgg    1740
agttacacca ctggaaatgg caagcgctac cggagcactg cgcggaccac ctacaccttt    1800
gccaagccaa tggcggctaa ctatctgaag aaccagccga tgtacgtgtt ccgtaagacg    1860
gagctcaagc actccaagac cgagctcaac ttcaaggagt ggcaaaaggc ctttaccgat    1920
gtgatgggca tggacgagct gtacaagtag                                     1950

<210> SEQ ID NO 53
<211> LENGTH: 649
<212> TYPE: PRT
<213> ORGANISM: Artificial Sequence
<220> FEATURE:
<223> OTHER INFORMATION: BArr L1-3B8 - coding sequence
<220> FEATURE:
<221> NAME/KEY: SITE
<222> LOCATION: (1)..(150)
<223> OTHER INFORMATION: mNeonGreen Part 1
<220> FEATURE:
<221> NAME/KEY: SITE
<222> LOCATION: (151)..(154)
<223> OTHER INFORMATION: N-terminal linker
<220> FEATURE:
<221> NAME/KEY: SITE
<222> LOCATION: (154)..(561)
<223> OTHER INFORMATION: B-Arrestin
<220> FEATURE:
<221> NAME/KEY: SITE
<222> LOCATION: (562)..(563)
<223> OTHER INFORMATION: C-terminal linker
<220> FEATURE:
<221> NAME/KEY: SITE
<222> LOCATION: (564)..(649)
<223> OTHER INFORMATION: mNeonGreen Part 2

<400> SEQUENCE: 53

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45
```

-continued

```
Leu Lys Ser Thr Lys Gly Asp Leu Gln Phe Ser Pro Trp Ile Leu Val
    50              55                  60

Pro His Ile Gly Tyr Gly Phe His Gln Tyr Leu Pro Tyr Pro Asp Gly
65              70                  75                  80

Met Ser Pro Phe Gln Ala Ala Met Val Asp Gly Ser Gly Tyr Gln Val
            85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ile Leu Trp Gly Glu Lys Pro Gly Thr Arg
145                 150                 155                 160

Val Phe Lys Lys Ser Ser Pro Asn Cys Lys Leu Thr Val Tyr Leu Gly
            165                 170                 175

Lys Arg Asp Phe Val Asp His Leu Asp Lys Val Asp Pro Val Asp Gly
            180                 185                 190

Val Val Leu Val Asp Pro Asp Tyr Leu Lys Asp Arg Lys Val Phe Val
        195                 200                 205

Thr Leu Thr Cys Ala Phe Arg Tyr Gly Arg Glu Asp Leu Asp Val Leu
    210                 215                 220

Gly Leu Ser Phe Arg Lys Asp Leu Phe Ile Ala Thr Tyr Gln Ala Phe
225                 230                 235                 240

Pro Pro Val Pro Asn Pro Pro Arg Pro Pro Thr Arg Leu Gln Asp Arg
            245                 250                 255

Leu Leu Arg Lys Leu Gly Gln His Ala His Pro Phe Phe Phe Thr Ile
            260                 265                 270

Pro Gln Asn Leu Pro Cys Ser Val Thr Leu Gln Pro Gly Pro Glu Asp
        275                 280                 285

Thr Gly Lys Ala Cys Gly Val Asp Phe Glu Ile Arg Ala Phe Cys Ala
    290                 295                 300

Lys Ser Leu Glu Glu Lys Ser His Lys Arg Asn Ser Val Arg Leu Val
305                 310                 315                 320

Ile Arg Lys Val Gln Phe Ala Pro Glu Lys Pro Gly Pro Gln Pro Ser
            325                 330                 335

Ala Glu Thr Thr Arg His Phe Leu Met Ser Asp Arg Ser Leu His Leu
            340                 345                 350

Glu Ala Ser Leu Asp Lys Glu Leu Tyr Tyr His Gly Glu Pro Leu Asn
        355                 360                 365

Val Asn Val His Val Thr Asn Asn Ser Thr Lys Thr Val Lys Lys Ile
    370                 375                 380

Lys Val Ser Val Arg Gln Tyr Ala Asp Ile Cys Leu Phe Ser Thr Ala
385                 390                 395                 400

Gln Tyr Lys Cys Pro Val Ala Gln Leu Glu Gln Asp Asp Gln Val Ser
            405                 410                 415

Pro Ser Ser Thr Phe Cys Lys Val Tyr Thr Ile Thr Pro Leu Leu Ser
            420                 425                 430

Asp Asn Arg Glu Lys Arg Gly Leu Ala Leu Asp Gly Lys Leu Lys His
        435                 440                 445

Glu Asp Thr Asn Leu Ala Ser Ser Thr Ile Val Lys Glu Gly Ala Asn
    450                 455                 460

Lys Glu Val Leu Gly Ile Leu Val Ser Tyr Arg Val Lys Val Lys Leu
```

```
465                470                475                480

Val Val Ser Arg Gly Gly Asp Val Ser Val Glu Leu Pro Phe Val Leu
                485                490                495

Met His Pro Lys Pro His Asp His Ile Pro Leu Pro Arg Pro Gln Ser
                500                505                510

Ala Ala Pro Glu Thr Asp Val Pro Val Asp Thr Asn Leu Ile Glu Phe
                515                520                525

Asp Thr Asn Tyr Ala Thr Asp Asp Asp Ile Val Phe Glu Asp Phe Ala
        530                535                540

Arg Leu Arg Leu Lys Gly Met Lys Asp Asp Asp Tyr Asp Asp Gln Leu
545                550                555                560

Cys Asn Val Ser Lys Lys Thr Tyr Pro Asn Asp Lys Thr Ile Ile Ser
                565                570                575

Thr Phe Lys Trp Ser Tyr Thr Thr Gly Asn Gly Lys Arg Tyr Arg Ser
                580                585                590

Thr Ala Arg Thr Thr Tyr Thr Phe Ala Lys Pro Met Ala Ala Asn Tyr
                595                600                605

Leu Lys Asn Gln Pro Met Tyr Val Phe Arg Lys Thr Glu Leu Lys His
        610                615                620

Ser Lys Thr Glu Leu Asn Phe Lys Glu Trp Gln Lys Ala Phe Thr Asp
625                630                635                640

Val Met Gly Met Asp Glu Leu Tyr Lys
                645
```

```
<210> SEQ ID NO 54
<211> LENGTH: 450
<212> TYPE: DNA
<213> ORGANISM: Artificial Sequence
<220> FEATURE:
<223> OTHER INFORMATION: BArr L1-3B8 - mNeonGreen Part 1
<220> FEATURE:
<221> NAME/KEY: misc_feature
<222> LOCATION: (1)..(450)
<223> OTHER INFORMATION: mNeonGreen Part 1

<400> SEQUENCE: 54
atggtgagca agggcgagga ggataacatg gcctctctcc cagcgacaca tgagttacac        60
atctttggct ccatcaacgg tgtggacttt gacatggtgg gtcagggcac cggcaatcca       120
aatgatggtt atgaggagtt aaacctgaag tccaccaagg gtgacctcca gttctccccc       180
tggattctgg tccctcatat cgggtatggc ttccatcagt acctgcccta ccctgacggg       240
atgtcgcctt ccaggccgc catggtagat ggctccggat accaagtcca tcgcacaatg       300
cagtttgaag atggtgcctc ccttactgtt aactaccgct acacctacga gggaagccac       360
atcaaaggag aggcccaggt gaagggact ggtttccctg ctgacggtcc tgtgatgacc       420
aactcgctga ccgctgcgga ctggtgcagg                                      450
```

```
<210> SEQ ID NO 55
<211> LENGTH: 150
<212> TYPE: PRT
<213> ORGANISM: Artificial Sequence
<220> FEATURE:
<223> OTHER INFORMATION: BArr L1-3B8 - mNeonGreen Part 1
<220> FEATURE:
<221> NAME/KEY: SITE
<222> LOCATION: (1)..(150)
<223> OTHER INFORMATION: mNeonGreen Part 1

<400> SEQUENCE: 55
```

-continued

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
            115                 120                 125

Gly Thr Gly Phe Pro Ala Asp Gly Pro Val Met Thr Asn Ser Leu Thr
    130                 135                 140

Ala Ala Asp Trp Cys Arg
145                 150
```

```
<210> SEQ ID NO 56
<211> LENGTH: 12
<212> TYPE: DNA
<213> ORGANISM: Artificial Sequence
<220> FEATURE:
<223> OTHER INFORMATION: BArr L1-3B8 - 1st linker sequence
<220> FEATURE:
<221> NAME/KEY: misc_feature
<222> LOCATION: (1)..(12)
<223> OTHER INFORMATION: N-terminal linker

<400> SEQUENCE: 56
atcctttggg gg                                                                          12

<210> SEQ ID NO 57
<211> LENGTH: 4
<212> TYPE: PRT
<213> ORGANISM: Artificial Sequence
<220> FEATURE:
<223> OTHER INFORMATION: BArr L1-3B8 - 1st Linker Sequence

<400> SEQUENCE: 57

Ile Leu Trp Gly
1

<210> SEQ ID NO 58

<400> SEQUENCE: 58

000

<210> SEQ ID NO 59
<211> LENGTH: 408
<212> TYPE: PRT
<213> ORGANISM: Artificial Sequence
<220> FEATURE:
<223> OTHER INFORMATION: BArr L1-3B8 - Beta-arrestin-2
<220> FEATURE:
<221> NAME/KEY: SITE
<222> LOCATION: (1)..(408)
<223> OTHER INFORMATION: B-Arrestin

<400> SEQUENCE: 59
```

-continued

```
Gly Glu Lys Pro Gly Thr Arg Val Phe Lys Lys Ser Ser Pro Asn Cys
1               5                   10                  15

Lys Leu Thr Val Tyr Leu Gly Lys Arg Asp Phe Val Asp His Leu Asp
            20                  25                  30

Lys Val Asp Pro Val Asp Gly Val Val Leu Val Asp Pro Asp Tyr Leu
            35                  40                  45

Lys Asp Arg Lys Val Phe Val Thr Leu Thr Cys Ala Phe Arg Tyr Gly
    50                  55                  60

Arg Glu Asp Leu Asp Val Leu Gly Leu Ser Phe Arg Lys Asp Leu Phe
65                  70                  75                  80

Ile Ala Thr Tyr Gln Ala Phe Pro Pro Val Pro Asn Pro Pro Arg Pro
                85                  90                  95

Pro Thr Arg Leu Gln Asp Arg Leu Leu Arg Lys Leu Gly Gln His Ala
            100                 105                 110

His Pro Phe Phe Phe Thr Ile Pro Gln Asn Leu Pro Cys Ser Val Thr
            115                 120                 125

Leu Gln Pro Gly Pro Glu Asp Thr Gly Lys Ala Cys Gly Val Asp Phe
    130                 135                 140

Glu Ile Arg Ala Phe Cys Ala Lys Ser Leu Glu Glu Lys Ser His Lys
145                 150                 155                 160

Arg Asn Ser Val Arg Leu Val Ile Arg Lys Val Gln Phe Ala Pro Glu
                165                 170                 175

Lys Pro Gly Pro Gln Pro Ser Ala Glu Thr Thr Arg His Phe Leu Met
            180                 185                 190

Ser Asp Arg Ser Leu His Leu Glu Ala Ser Leu Asp Lys Glu Leu Tyr
            195                 200                 205

Tyr His Gly Glu Pro Leu Asn Val Asn Val His Val Thr Asn Asn Ser
    210                 215                 220

Thr Lys Thr Val Lys Lys Ile Lys Val Ser Val Arg Gln Tyr Ala Asp
225                 230                 235                 240

Ile Cys Leu Phe Ser Thr Ala Gln Tyr Lys Cys Pro Val Ala Gln Leu
                245                 250                 255

Glu Gln Asp Asp Gln Val Ser Pro Ser Ser Thr Phe Cys Lys Val Tyr
            260                 265                 270

Thr Ile Thr Pro Leu Leu Ser Asp Asn Arg Glu Lys Arg Gly Leu Ala
            275                 280                 285

Leu Asp Gly Lys Leu Lys His Glu Asp Thr Asn Leu Ala Ser Ser Thr
    290                 295                 300

Ile Val Lys Glu Gly Ala Asn Lys Glu Val Leu Gly Ile Leu Val Ser
305                 310                 315                 320

Tyr Arg Val Lys Val Lys Leu Val Val Ser Arg Gly Gly Asp Val Ser
            325                 330                 335

Val Glu Leu Pro Phe Val Leu Met His Pro Lys Pro His Asp His Ile
            340                 345                 350

Pro Leu Pro Arg Pro Gln Ser Ala Ala Pro Glu Thr Asp Val Pro Val
            355                 360                 365

Asp Thr Asn Leu Ile Glu Phe Asp Thr Asn Tyr Ala Thr Asp Asp Asp
    370                 375                 380

Ile Val Phe Glu Asp Phe Ala Arg Leu Arg Leu Lys Gly Met Lys Asp
385                 390                 395                 400

Asp Asp Tyr Asp Asp Gln Leu Cys
            405
```

-continued

```
<210> SEQ ID NO 60
<211> LENGTH: 261
<212> TYPE: DNA
<213> ORGANISM: Artificial Sequence
<220> FEATURE:
<223> OTHER INFORMATION: BArr L1-3B8 - mNeonGreen Part 2
<220> FEATURE:
<221> NAME/KEY: misc_feature
<222> LOCATION: (1)..(261)
<223> OTHER INFORMATION: mNeonGreen Part 2

<400> SEQUENCE: 60
tcgaagaaga cttaccccaa cgacaaaacc atcatcagta cctttaagtg gagttacacc      60
actggaaatg gcaagcgcta ccggagcact gcgcggacca cctacacctt tgccaagcca     120
atggcggcta actatctgaa gaaccagccg atgtacgtgt tccgtaagac ggagctcaag     180
cactccaaga ccgagctcaa cttcaaggag tggcaaaagg cctttaccga tgtgatgggc     240
atggacgagc tgtacaagta g                                              261

<210> SEQ ID NO 61
<211> LENGTH: 86
<212> TYPE: PRT
<213> ORGANISM: Artificial Sequence
<220> FEATURE:
<223> OTHER INFORMATION: BArr L1-3B8 - mNeonGreen Part 2
<220> FEATURE:
<221> NAME/KEY: SITE
<222> LOCATION: (1)..(86)
<223> OTHER INFORMATION: mNeonGreen Part 2

<400> SEQUENCE: 61

Ser Lys Lys Thr Tyr Pro Asn Asp Lys Thr Ile Ile Ser Thr Phe Lys
1               5                   10                  15

Trp Ser Tyr Thr Thr Gly Asn Gly Lys Arg Tyr Arg Ser Thr Ala Arg
            20                  25                  30

Thr Thr Tyr Thr Phe Ala Lys Pro Met Ala Ala Asn Tyr Leu Lys Asn
        35                  40                  45

Gln Pro Met Tyr Val Phe Arg Lys Thr Glu Leu Lys His Ser Lys Thr
    50                  55                  60

Glu Leu Asn Phe Lys Glu Trp Gln Lys Ala Phe Thr Asp Val Met Gly
65                  70                  75                  80

Met Asp Glu Leu Tyr Lys
                85
```

BIOSENSORS FOR DETECTING ARRESTIN SIGNALING

RELATED APPLICATIONS

This application claims priority to U.S. Provisional Patent Application No. 62/712,176, filed on Jul. 30, 2018, incorporated herein by reference in its entirety.

GOVERNMENT SUPPORT

This invention was made with government support under grant numbers R44DA050357 and R44GM125390 awarded by the National Institutes of Health. The government has certain rights in the invention.

REFERENCE TO SEQUENCE LISTING SUBMITTED ELECTRONICALLY

The content of the electronically submitted sequence listing in ASCII text file (Name: 615319_SeqList_ST25.txt; Size: 199 kilobytes; and Date of Creation: Jul. 30, 2019) is incorporated herein by reference in its entirety.

FIELD

This disclosure relates generally to biological sensors for detecting cell signaling in live cells.

BACKGROUND

Over the past decade there has been a growing realization that different ligands or small molecules can act at the same receptor to cause very different patterns of intracellular signaling. This is known as agonist bias, a situation in which a ligand is biased towards the activation of one signaling pathway or another. Different ligands for the same receptor can stabilize that receptor in different conformations, leading to different signaling pathways being activated in the same receptor by different agonists (Kenakin et al. Br J Pharmacol. 2012 March; 165 (6): 1659-1669 (2010); Sprang et al. Science. 2012 Mar. 2; 335 (6072): 1055-6).

Currently, at the seven transmembrane receptors, the two signaling pathways are initiated by either the heterotrimeric G-proteins, or by arrestin following agonist activation of the receptor. The seven transmembrane receptors are a significant drug target, and there is reason to believe that at the opiate receptor it might be possible to find a biased ligand that is analgesic, but not addictive (DeWire et al. J Pharmacol Exp Ther. 2013 March; 344 (3): 708-17). Similarly, there are active lines of research dedicated to finding biased agonists at the cannabinoid (Flores-Otero et al. Nat Commun. 2014 Aug. 1; 5:4589; van der Lee et al. J Biomol Screen. 2009 August; 14 (7): 811-23) and dopamine (Masri et al. Proc Natl Acad Sci USA. 2008 Sep. 9; 105 (36): 13656-61) receptors of the central nervous system.

However, identifying a biased ligand for a receptor that activates one signaling pathway more than another requires testing a given ligand using two different assays in parallel, one that assays for G-protein activation, and another that detects arrestin signaling. This is problematic, as each assay is quite different in terms of the linearity of the response, the time period used in the assay, the detection method and sensitivity, and the expression level of the receptor in two different cell lines. This makes it difficult to reliably assess a biased ligand that results in one signaling pathway being used over the other (see, e.g. Kenakin et al. 2012).

U.S. Pat. Nos. 5,891,646 and 7,138,240 describe a beta-arrestin-2-GFP fusion protein that can detect translocation of the fusion protein to the membrane following agonist activation of the β2 adrenergic receptor. However, the assay requires analysis of individual cells and movement of the Green Fluorescent Protein (GFP) from cytosol to membrane. Detection of this subcellular movement utilizes complex and expensive high-resolution microscopy and pattern recognition software, or total internal reflection fluorescence (TIRF) microscopy, which is expensive and complex to utilize. U.S. Patent Application No. 20100120063A1 and U.S. Pat. No. 9,388,449 describe target G-protein coupled receptors (GPCR) fused to a small fragment of β-galactosidase through a linker comprising a phosphorylation site and a second fusion protein comprising arrestin fused to a large fragment of β-galactosidase. However, this requires linking the GPCR to the enzyme fragment. Thus, there is clearly a need for improved tools and methods for measuring arrestin signaling in live cells.

SUMMARY

The summary of the technology described above is non-limiting and other features and advantages of the invention will be apparent from the following detailed description of the technology, and from the claims.

The instant disclosure provides nucleic acids, cells, vectors, and methods for detecting cells and tissues that have receptors that associate with arrestin protein after a cellular receptor associates with an agonist.

In some embodiment, the fusion protein is encoded by any of the Barr 1A Barr 3D, Barr 3F, Barr 4A, Barr 5A, Barr 6B or BArrL1-3B8 constructs.

Accordingly, in one aspect, the instant disclosure provides a nucleic acid encoding a fusion protein, the nucleic acid comprising from 5' to 3': a nucleic acid sequence encoding a fluorescent protein; a linker sequence encoding at least one amino acid; and a nucleic acid sequence encoding an arrestin protein, wherein the fusion protein encoded by the nucleic acid sequences undergoes a change in fluorescence upon association with an intracellular portion of a G-protein-coupled receptor.

In one embodiment, the fluorescent protein encoded by a nucleic acid encoding a fusion protein is circularly permuted. In another embodiment, the fluorescent protein is mNeonGreen. In another embodiment, the nucleic acid encoding the fusion protein comprises the nucleic acid sequence of SEQ ID NO: 2. In another embodiment, the nucleic acid encoding the fusion protein comprises the nucleic acid sequence of the sequence of SEQ ID NO: 3. In one embodiment, the nucleic acid encoding the fusion protein encodes for a circularly permuted fluorescent protein, wherein the circularly permuted m NeonGreen is encoded by a nucleic acid comprising the nucleic acid sequence of SEQ ID NO: 4. In another embodiment, the circularly permuted fluorescent protein is mNeonGreen. In some embodiments, mNeonGreen comprises the amino acid sequence of SEQ ID NO: 5. In one embodiment, the nucleic acid encoding the fusion protein encodes for a linker sequence comprising the amino acid glycine, or analogues thereof.

In one embodiment, the nucleic acid encoding the fusion protein encodes for an arrestin protein, wherein arrestin is beta-arrestin-2 is encoded by a nucleic acid comprising the nucleic acid sequence of SEQ ID NO: 6 and the beta-arrestin-2 protein sequence comprises the amino acid sequence of SEQ ID NO: 7.

In one aspect, the nucleic acid encoding a fusion protein is encoded by a nucleic acid comprising from 5' to 3': a nucleic acid sequence encoding an arrestin protein; a linker sequence encoding at least one amino acid; and a nucleic acid sequence encoding a fluorescent protein, wherein the fusion protein encoded by the nucleic acid sequences undergoes a change in fluorescence upon association with an intracellular portion of a G-protein-coupled receptor.

In one embodiment, the nucleic acid encodes for a fusion protein, wherein the fluorescent protein is circularly permuted. In another embodiment, the fluorescent protein is mNeonGreen. In another embodiment, the nucleic acid encoding the fusion protein comprises the nucleic acid sequence of SEQ ID NOs: 9 or 16. In another embodiment, the nucleic acid encodes for a fusion protein comprising the amino acid sequence of SEQ ID NOs: 10 or 17.

In one embodiment, the nucleic acid encoding the fusion protein encodes for an arrestin protein, wherein the arrestin protein is beta-arrestin-2 encoded by a nucleic acid comprising the nucleic acid sequence of SEQ ID NOs: 11 and 18. In another embodiment, the nucleic acid encoding the fusion protein encodes for arrestin protein, wherein arrestin is beta-arrestin-2 and the beta-arrestin-2 protein comprises the amino acid sequence of SEQ ID NOs: 12 or 19.

In another embodiment, the nucleic acid encoding the fusion protein encodes for the amino acid sequence of proline-serine-histidine, or amino acid analogues thereof. In another embodiment, the nucleic acid encoding the fusion protein encodes for a circularly permuted fluorescent protein wherein the circularly permuted protein is mNeonGreen encoded by a nucleic acid comprising the nucleic acid sequence of SEQ ID NOs: 13 or 20. In some embodiments, the fluorescent protein comprises the amino acid sequences of SEQ ID NOs: 14 or 21.

In one aspect, a nucleic acid encoding a fusion protein is provided comprising from 5' to 3': a nucleic acid sequence encoding a first portion of a fluorescent protein; a nucleic acid sequence encoding an arrestin protein; and a nucleic acid sequence encoding a second portion of the fluorescent protein, wherein the fusion protein encoded by the nucleic acid sequences undergoes a change in fluorescence upon association with an intracellular portion of a G-protein-coupled receptor.

In one embodiment, the nucleic acid encoding the fusion protein encodes a fluorescent protein which is mNeonGreen. In another embodiment, the nucleic acid encoding the fusion protein comprises a nucleic acid sequence selected from the group consisting of SEQ ID NOs: 23, 32, 41, and 52. In another embodiment, the fusion protein comprises an amino acid sequence selected from the group consisting of SEQ ID NOs: 24, 33, 42, and 53. In another embodiment, a first portion of the fluorescent protein is encoded by a nucleic acid comprising a nucleic acid sequence selected from the group consisting of SEQ ID NOs: 25, 34, 43, and 54.

In another embodiment, the first portion of the fluorescent protein comprises an amino acid sequence selected from the group consisting of SEQ ID NOs: 26, 35, 44, and 55. In another embodiment, the arrestin protein is beta-arrestin-2 protein, wherein the beta-arrestin-2 is encoded by a nucleic acid comprising a nucleic acid sequence selected from the group consisting of SEQ ID NOs: 27, 36, 47, and 58. In another embodiment, the arrestin protein comprises an amino acid sequence selected from the group consisting of SEQ ID NOs: 28, 37, 48, and 59.

In one embodiment, the nucleic acid encoding the fusion protein comprises a second portion of the fluorescent protein, encoded by a nucleic acid comprising a nucleic acid sequence selected from the group consisting of SEQ ID NOs: 29, 38, 49 and 60. In another embodiment, the second portion of the fluorescent protein comprises an amino acid sequence selected from the group consisting of SEQ ID NOs: 30, 39, 50 and 61.

In one aspect, a nucleic acid encoding a fusion protein comprising from 5' to 3': a nucleic acid sequence encoding a first portion of a fluorescent protein; a first linker sequence encoding at least one amino acid; a nucleic acid sequence encoding an arrestin protein; a second linker sequence encoding at least one amino acid; and a nucleic acid sequence encoding a second portion of the fluorescent protein, wherein the fusion protein encoded by the nucleic acid undergoes a change in fluorescence upon association with an intracellular portion of a G-protein-coupled receptor. In one embodiment, the nucleic acid encodes a fusion protein, wherein the fluorescent protein is m NeonGreen. In another embodiment, the nucleic acid encoding the fusion protein comprises a nucleic acid sequence selected from the group consisting of SEQ ID NOs: 23, 32, 41, and 52. In another embodiment, the fusion protein comprises an amino acid sequence selected from the group consisting of SEQ ID NOs: 24, 33, 42, and 53. In another embodiment, the first portion of the fluorescent protein is encoded by a nucleic acid comprising a nucleic acid sequence selected from the group consisting of SEQ ID NOs: 25, 34, 43, and 54. In another embodiment, the first portion of the fluorescent protein comprises an amino acid sequence selected from the group consisting of SEQ ID NOs: 26, 35, 44, and 55. In another embodiment, the first linker encodes an amino acid or peptide comprising an amino acid sequence selected from the group consisting of Gly, Met-Arg-Gly, SEQ ID NO: 46, and SEQ ID NO 57. In one embodiment, the arrestin protein is beta-arrestin-2, wherein beta-arrestin-2 is encoded by a nucleic acid comprising a nucleic acid sequence selected from the group consisting of SEQ ID NOs: 27, 36, 47, and 58. In another embodiment, the arrestin protein comprises an amino acid sequence selected from the group consisting of SEQ ID NOs: 28, 37, 48, and 59.30. In another embodiment, the amino acid sequence encoded by the second linker is selected from the group consisting of: no linker, and Asn-Val. In another embodiment, second portion of the fluorescent protein is encoded by a nucleic acid comprising a nucleic acid sequence selected from the group consisting of SEQ ID NOs: 29, 38, 49 and 60. In another embodiment, the second portion of the fluorescent protein comprises an amino acid sequence selected from the group SEQ ID NOs: 30, 39, 50 and 61.

The disclosure also provides a vector is provided, comprising the nucleic acid encoding the fusion protein, as described herein.

The disclosure also provides a cell is provided, comprising the nucleic acid encoding the fusion protein or parts thereof, as described herein, or the vector encoding the fusion protein or parts thereof.

The disclosure also provides a kit is provided comprising the nucleic acid of the fusion protein, as described herein, or a fragment thereof, or the vector encoding for the fusion protein, or a part thereof.

The disclosure also provides a protein is that is encoded by the nucleic acid of the fusion protein, as described herein.

The disclosure also provides a method is provided for measuring arrestin signaling in a cell, the method comprising: exposing a cell comprising the nucleic acid encoding the fusion protein, or a part thereof, to light having an excitation wavelength of the fusion protein, and measuring the fluorescence from the cell at the emission wavelength of the fusion protein.

In some embodiments, the method further comprises contacting the cell with a molecule that binds a G-protein coupled receptor. In another embodiment, the molecule that binds a G-protein coupled receptor is selected from the group consisting of angiotensin, SIIB, Isoproterenol, isoetherine, dopamine, clenbuterol, formoterol, salbutomol, salmeterol, TRV120055, TRV120045, and TRV120026. In another embodiment, multiple measurements of fluorescence are made over a time span. In another embodiment, the time span of measuring fluorescence is at least 90 seconds. In another embodiment, the time span of measuring fluorescence is at least 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least about 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least 15 minutes. In another embodiment, the time span of measuring fluorescence is at least 1, 2, 3, 4, 5, 6, 7, 8, 9, 10, 11, 12, 13, 14, 15, 16, 17, 18, 19, 20, 30, 40, 50 or 60 minutes. In another embodiment, the time span of measuring fluorescence is at least about 1, 2, 3, 4, 5, 6, 7, 8, 9, 10, 11, 12, 13, 14, 15, 16, 17, 18, 19, 20, 30, 40, 50 or 60 minutes. In another embodiment, multiple measurements are taken over the time span. In another embodiment, there are 2, 3, 4, 5, 6, 7, 8, 9, 10, 20, 30, 40, 50, 60, 70, 80, 90, 100, 150, 200, or more measurements taken over the time span. In another embodiment, a measurement is made between 0.01 and 3000 seconds after contacting the cell with a molecule that binds a G-protein coupled receptor. In other embodiments, a measurement is made between 0.1 and 3000, 1 and 3000, 5 and 3000, 0.01 and 100, 0.1 and 100, 1 and 100, 5 and 100, 0.01 and 20, 0.1 and 20, 1 and 20, 5 and 20, 0.01 and 10, 0.1 and 10, 1 and 10, or 5 and 10, seconds after contacting the cell with a molecule that binds a G-protein coupled receptor.

In some embodiments, the method also includes the step of detecting a second biological molecule selected from the group consisting of $Ca^{2+}$, cAMP, cGMP, diacylglycerol, ATP, ADP, glucose, ribose, sucrose, glutamate, hydrogen peroxide, lactate, magnesium, NAD+, NADH, phosphate, reactive oxygen species, and zinc with a second fluorescent biosensor.

The disclosure also provides a method is provided for comparing the effects of molecules on a G-protein coupled receptor, the method comprising: contacting a cell comprising the nucleic acid described above with a molecule that binds a G-protein coupled receptor, exposing said cell to light having an excitation wavelength of the fusion protein, and measuring the fluorescence from the cell at the emission wavelength of the fusion protein over a time span.

In some embodiments, multiple measurements of fluorescence are made over a time span. In another embodiment, the time span of measuring fluorescence is at least 90 seconds. In another embodiment, the time span of measuring fluorescence is at least 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least about 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least 15 minutes. In another embodiment, the time span of measuring fluorescence is at least 1, 2, 3, 4, 5, 6, 7, 8, 9, 10, 11, 12, 13, 14, 15, 16, 17, 18, 19, 20, 30, 40, 50 or 60 minutes. In another embodiment, the time span of measuring fluorescence is at least about 1, 2, 3, 4, 5, 6, 7, 8, 9, 10, 11, 12, 13, 14, 15, 16, 17, 18, 19, 20, 30, 40, 50 or 60 minutes. In another embodiment, multiple measurements are taken over the time span. In another embodiment, there are 2, 3, 4, 5, 6, 7, 8, 9, 10, 20, 30, 40, 50, 60, 70, 80, 90, 100, 150, 200, or more measurements taken over the time span. In another embodiment, a measurement is made between 0.01 and 3000 seconds after contacting the cell with a molecule that binds a G-protein coupled receptor. In other embodiments, a measurement is made between 0.1 and 3000, 1 and 3000, 5 and 3000, 0.01 and 100, 0.1 and 100, 1 and 100, 5 and 100, 0.01 and 20, 0.1 and 20, 1 and 20, 5 and 20, 0.01 and 10, 0.1 and 10, 1 and 10, or 5 and 10, seconds after contacting the cell with a molecule that binds a G-protein coupled receptor.

In some embodiments, a change in fluorescence over a time span correlates with an effect of a molecule on a G-protein coupled receptor. In one embodiment, the change in fluorescence over a time span equals the rate in the change in fluorescence over a time span upon binding of a molecule to a G-protein coupled receptor. In one embodiment, a maximum or a minimum value of fluorescence correlates with an effect of a molecule on a G-protein coupled receptor.

In some embodiments, the method also includes the step of detecting a second biological molecule selected from the group consisting of $Ca^{2+}$, cAMP, cGMP, diacylglycerol, ATP, ADP, glucose, ribose, sucrose, glutamate, hydrogen peroxide, lactate, magnesium, NAD+, NADH, phosphate, reactive oxygen species, and zinc with a second fluorescent biosensor.

The disclosure also provides a method is provided for determining a more optimum time for measuring arrestin signaling in a cell, the method comprising: exposing a cell comprising the nucleic acid described above to light having an excitation wavelength of the fluorescent protein, and measuring the fluorescence from the cell at the emission wavelength of the fluorescent protein at two or more time points, wherein the time point that shows the greater difference between a control result and a result generated by contacting the cell with a molecule that binds a G-protein coupled receptor is the more optimum time for measuring arrestin signaling in the cell.

In some embodiments, the fluorescence from the cell at the emission wavelength of the fluorescent protein is measured at 3, 4, 5, 6, 7, 8, 9, 10, 20, 30, 40, 50, 60, 70, 80, 90, 100, 200, 300, 400, 500, 600, 700, 800, 900, 1000, or more time points. In one embodiment, the time points have an interval of at least 0.01 seconds between them. In some embodiments, the interval is 0.01, 0.1, 0.5, 1.0, 2.0, 3.0, 4.0, 5.0, or more seconds. In another embodiment, the optimum time is 1, 2, 3, 4, 5, or more seconds from when the cell is contacted with a molecule that binds a G-protein coupled receptor.

The disclosure also provides a method for measuring bias of arrestin and G-protein signaling in a cell, the method comprising exposing a cell comprising the nucleic acid encoding the fusion protein described above and a cell comprising a biosensor that detects G-protein signaling that fluoresces at a wavelength distinct from the fusion protein, to light having an excitation wavelength of the fusion protein, measuring the fluorescence from the cell comprising the nucleic acid encoding the fusion protein described above at the emission wavelength of the fusion protein, measuring the fluorescence from the cell comprising a biosensor that detects G-protein signaling at the wavelength that is distinct from the wavelength at which the fusion protein fluoresces, comparing each measured fluorescence to a respective standard and comparing change in fluorescence of the fluorescence of the emission wavelength of the fusion protein in relation to its respective standard to change in fluorescence of the emission wavelength of the biosensor that detects G-protein signaling.

In some embodiments, multiple measurements of fluorescence are made over a time span. In another embodiment, the time span of measuring fluorescence is at least 90 seconds. In another embodiment, the time span of measuring fluorescence is at least 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least about 1, 2, 3, 4, 5, 6, 7, 8, 9, 10, 20, 30, 40, 50, 60, 70, 80, 90, 100, 110 or 120 seconds. In another embodiment, the time span of measuring fluorescence is at least 15 minutes. In another embodiment, the time span of measuring fluorescence is at least 1, 2, 3, 4, 5, 6, 7, 8, 9, 10, 11, 12, 13, 14, 15, 16, 17, 18, 19, 20, 30, 40, 50 or 60 minutes. In another embodiment, the time span of measuring fluorescence is at least about 1, 2, 3, 4, 5, 6, 7, 8, 9, 10, 11, 12, 13, 14, 15, 16, 17, 18, 19, 20, 30, 40, 50 or 60 minutes. In another embodiment, multiple measurements are taken over the time span. In another embodiment, there are 2, 3, 4, 5, 6, 7, 8, 9, 10, 20, 30, 40, 50, 60, 70, 80, 90, 100, 150, 200, or more measurements taken over the time span.

In some embodiments, the cell comprising the nucleic acid encoding the fusion protein described above and the cell comprising a biosensor that detects G-protein are the same cell. In some embodiments, the cell comprising the nucleic acid encoding the fusion protein described above and the cell comprising a biosensor that detects G-protein are different cells. In some embodiments, the detection of fluorescence in the different cells is done simultaneously or within one minute of each other.

BRIEF DESCRIPTION OF THE FIGURES

FIG. 3A is a table of SEQ ID NOs for nucleic acid and amino acid sequences of construct BArr 1A.

FIG. 3B is a table of SEQ ID NOs for nucleic acid and amino acid sequences of constructs BArr 3D and BArr 3F.

FIG. 3C is a table of SEQ ID NOs (nucleic acid and amino acid) for constructs BArr 4A, BArr 5A, BArr 6B, and BArr L1-3B8.

FIG. 3D is a table of SEQ ID NOs (nucleic acid and amino acid) for portions of constructs BArr 4A, BArr 5A, BArr 6B, and BArr L1-3B8.

DETAILED DESCRIPTION

Figures 1A, 1B:
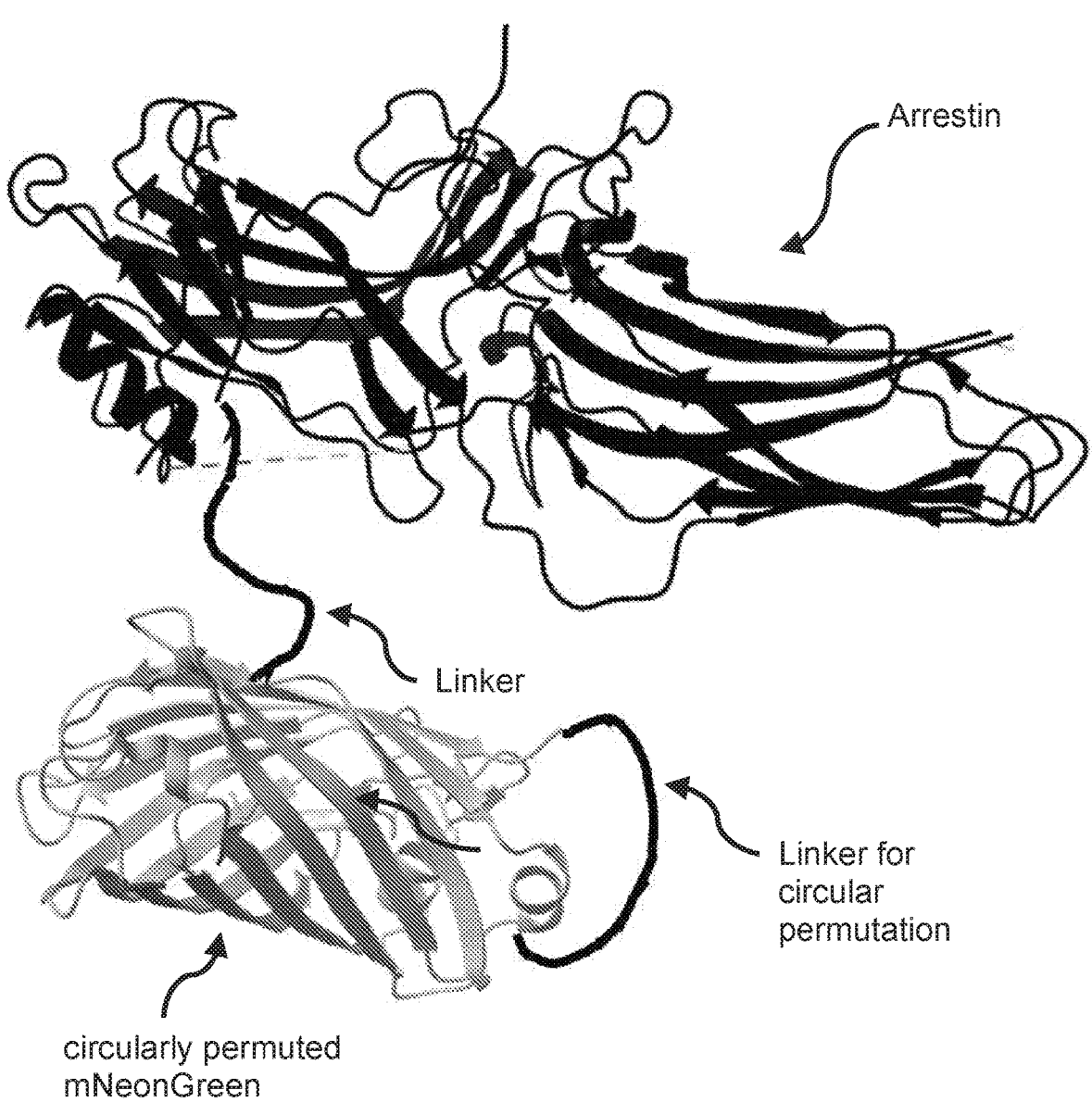
FIG. 1A is a ribbon diagram illustrating a first embodiment of an arrestin biosensor.
FIG. 1B is a block diagram of the arrestin biosensor of FIG. 1A, with the N-terminus on the left and C-terminus on the right.

The technology described herein provides nucleic acid constructs for biosensors that can detect arrestin recruitment to GPCRs using changes in fluorescence intensity that are easy to detect. In particular, the disclosure describes fluorescent sensor systems that can be used to identify biased agonists for receptors in live cells that are utilizing arrestin signaling in response to an agonist. The arrestin biosensor may be used in conjunction with one or more biosensors that detects another cell signaling molecule (e.g. diacylglycerol or cAMP) to simultaneously detect changes in both arrestin signaling and the one or more cell signaling molecules. As described further below, nucleic acids encoding the fluorescent sensor systems described herein can be introduced into a cell to allow detection of the cell's intracellular arrestin signaling as detected by the biosensor. Such sensor systems comprise fusion proteins that include a reporter protein and an arrestin protein encoded by an engineered nucleic acid. The reporter proteins may be a fluorescent protein, a bioluminescent protein, or a fluorescent biosensor. In some embodiments, the fusion protein can fluoresce when the arrestin portion of the protein is not associated with an intracellular domain of a receptor, and does not fluoresce when the arrestin protein is associated with an intracellular domain of a receptor. This change in fluorescence is due to a conformational change in the structure of the arrestin domain of the fusion protein that causes a conformational change in the structure of the reporter domain and reduces its fluorescent properties.

Definitions

Unless defined otherwise, all technical and scientific terms used herein have the same meaning as commonly understood by one of ordinary skill in the art.

As used herein, the term "nucleic acid" refers to a polymer of two or more nucleotides or nucleotide analogues (such as ribonucleic acid having methylene bridge between the 2'-O and 4'-C atoms of the ribose ring) capable of hybridizing to a complementary nucleic acid. As used herein, this term includes, without limitation, DNA, RNA, LNA, and PNA. A nucleic acid may be single-stranded or double-stranded. Where the nucleic acid is single-stranded, a skilled person in the art will appreciate that the nucleic acid can be in the sense or antisense orientation relative to the direction of transcription of the reporter genes.

As used herein, the term "gene" refers to a nucleic acid sequence that encodes an amino acid sequence. A gene of the invention can include a nucleic acid sequence that is a contiguous coding sequence (e.g., an open reading frame; ORF), as well as nucleic acid sequences that contain exons and introns. In the context of the instant technology, the term gene can, but need not, include regulatory sequences such as, for example, promoter sequences, enhancer sequence, polyadenylation signals, and the like.

Genes of the instant technology can be joined to regulatory sequences, such as promoters, thereby allowing expression of the genes. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. beta-actin promoter or EF1α promoter, or from hybrid or chimeric promoters (e.g., CMV promoter fused to the beta-actin promoter). Promoters from the host cell or related species are also useful herein.

As used herein, the term "enhancer" generally refers to a sequence of DNA that functions at no fixed distance from the transcription start site and can be either 5' or 3' to the transcription unit. Furthermore, enhancers can be within an intron as well as within the coding sequence itself. Enhancers are usually between 10 and 300 base pairs in length, and function in cis. Enhancers usually function to increase transcription from nearby promoters; in some species (e.g. *D. melanogaster*), enhancers can function in trans on a corresponding allele on another chromosome. Enhancers can also contain response elements that mediate the regulation of transcription. While many enhancer sequences are known from mammalian genes (globin, elastase, albumin, fetoprotein, and insulin), typically enhancers from a eukaryotic cell virus are used for general expression. Preferred examples are the SV40 enhancer on the late side of the replication origin, the cytomegalovirus early promoter enhancer, the polyoma enhancer on the late side of the replication origin, and adenovirus enhancers.

Genes in constructs of the invention can be operatively linked to the same promoter, or each gene can be independently, operatively linked to a different promoter. As used herein, the term "operatively linked" means that the promoter can direct the expression of a linked sequence, which encodes protein. In one embodiment, a first gene and a second gene are operatively linked to the same promoter. The promoter and/or an enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

In one embodiment, transcription from the promoter results in production of a polycistronic mRNA molecule comprising the first gene sequence and the first and second exon sequences. As used herein, the term "polycistronic mRNA" is a mRNA molecule that carries multiple, independent coding regions that can produce multiple, independent proteins. There are many ways of creating such mRNAs, which include, without limitation, internal ribosomal entry sites (IRES), 2A peptide sequences (Szymczak et al. 2004), or strategically positioned alternative translation start signals. In one embodiment, the nucleic acid molecule comprises an internal ribosomal entry site (IRES) sequence upstream of the first exon. In one embodiment, the nucleic acid molecule comprises a sequence encoding a 2A peptide sequence upstream of the first exon. For example, an engineered nucleic acid can encode the arrestin biosensor and one or more additional protein biosensors, resulting in a polycistronic mRNA that can be translated into two or more separate proteins.

As used herein, the term "fusion protein" refers to a protein including at least two protein domains that are encoded by separate genes that have been joined so that they are transcribed and translated as a single unit, producing a single polypeptide.

As used herein, the term "G-protein coupled receptor" or "GPCR" refers to a class of receptors with seven transmembrane domains, and have an intracellular domain that associates with G-proteins and other molecules as part of one or more intracellular signaling pathways (e.g. cAMP signaling pathway or phosphatidylinositol signaling pathway). An intracellular domain of a GPCR activated by an agonist (primarily the C-terminal region) is phosphorylated by G-protein-coupled receptor kinases (GRKs), thereby allowing association of an arrestin protein. Association of the arrestin protein with the phosphorylated GPCR can result in either internalization and trafficking of the GPCR (via clathrin), or arrestin-mediated signaling via association of the c-Raf1-MEK1-ERK2 signaling cascade.

As used herein, the term "arrestin protein" refers to any protein from the arrestin family of proteins. Arrestin proteins participate in the desensitization of agonist-activated receptors by preventing re-association of G-proteins to the GPCR. Arrestin structure is characterized by two crescent-shaped beta-sandwiches, called the N- and C-domains. The central crest formed between the N- and C-domains includes the finger loop, the middle loop, and the C-loop. The finger loop is important for receptor binding, while the middle loop and C-loop are important for stabilizing arrestin that is inactive (see Scheerer et al. Curr Opin Struct Biol. 2017 August; 45:160-169).

Arrestins are grouped into four subtypes. Arrestin-1, also known as SAG or S-antigen visual arrestin is found in photoreceptors and cells of the pineal gland. Arrestin-2, also called beta arrestin or beta arrestin-1 is encoded by the ARRB1 gene in humans and ArrB1 in mice. Beta-arrestin-1 is a cofactor in the beta-adrenergic receptor kinase (BARK) mediated desensitization of beta-adrenergic receptors, among many other GPCRs. Beta-arrestin-1 is highly expressed in both the central nervous system and in peripheral blood leukocytes. Arrestin-3, also called beta-arrestin-2 or arrestin beta-2, is encoded by the gene ARRB2 in humans and ArrB2 in mice. Like beta-arrestin-1, beta-arrestin-2 is highly expressed in the central nervous system, as well as in the thyroid. Arrestin-4, also called Arrestin-C, retinal cone arrestin-3, or cone arrestin, is encoded by the gene ARR3 in humans and Arr3 in mice.

As used herein, the term "reporter protein" refers to a protein that is detectable by a user when expressed by a cell in a non-truncated form, and the term "reporter gene" refers to a gene encoding a reporter protein. For example, a reporter protein may be a fluorescent protein that fluoresces when exposed to a certain wavelength of light (e.g. GFP, enhanced GFP). A reporter protein may be fluorescent biosensor that changes its fluorescence properties in response to a particular type of cell signaling. A reporter protein may be an enzyme that catalyzes a reaction with a substrate to produce an observable change in that substrate, such as the luminescent enzyme luciferase which acts on luciferin or other substrates to emit photons, or β-galactosidase which can hydrolyze X-gal (5-bromo-4-chloro-3-indolyl-β-D-galactopyranoside) to form a blue precipitate that can visualized.

As used herein, the term "bioluminescent protein" refers to a protein that catalyzes a reaction with a substrate to emit photons, without needing a light source to excite the protein. Exemplary bioluminescent proteins include, but are not limited to: luciferase (e.g. from fireflies, jellyfish, or dinoflagellates), aequorin (which emits photons when oxidized in the presence of $Ca^{2+}$).

As used herein, the term "fluorescent protein" refers to a protein that emits light at some wavelength after excitation by light at another wavelength. Exemplary fluorescent proteins that emit in the green spectrum range include, but are not limited to: green fluorescent protein (GFP); enhanced GFP (EGFP); superfolder GFP; AcGFP1; and ZsGreen1; and mNeonGreen. Exemplary fluorescent proteins that emit light in the blue spectrum range include, but are not limited to: enhanced blue fluorescent protein (EBFP), EBFP2, Azurite, and mKalama1. Exemplary fluorescent proteins that emit light in the cyan spectrum range include, but are not limited to: cyan fluorescent protein (CFP); enhanced CFP (ECFP); Cerulean; mHoneydew; and CyPet. Exemplary fluorescent proteins that emit light in the yellow spectrum range include, but are not limited to: yellow fluorescent protein (YFP); Citrine; Venus; mBanana; ZsYellow1; and Ypet. Exemplary fluorescent proteins that emit in the orange spectrum range include, but are not limited to: mOrange; tdTomato; Exemplary fluorescent proteins that emit light in the red and far-red spectrum range include, but are not limited to: DsRed; DsRed-monomer; DsRed-Express2; mRFP1; mCherry; mStrawberry; mRaspberry; mPlum; E2-Crimson; iRFP670; iRFP682; iRFP702; iRFP720. Far red fluorescent proteins (e.g. iRFP670; iRFP682; iRFP702; iRFP720) can be useful for animal or thick tissue preparations, as the wavelength is able to penetrate these thicker structures. Such far red proteins can be engineered into biosensors (see, e.g. Shcherbakova et al. 2016, fusing miRFP703 to IxBa to detect NF-κB activation). Exemplary listings of fluorescent proteins and their characteristics may be found in Day and Davidson. Chem Soc Rev. 2009 October; 38 (10): 2887-921, and in Rodriguez et al. Front Microbiol. 2017 Dec. 14; 8:2491, each of which is incorporated herein by reference.

Fluorescent proteins may include chimeric combinations of fluorescent proteins that transfer and receive energy through fluorescent resonance energy transfer (FRET) when exposed to a particular wavelength of light. In some embodiments, an acceptor in a FRET pair may emit light at a certain wavelength after accepting energy from a donor molecule exposed to another wavelength of light. Exemplary chimeric FRET pairs, include, but are not limited to ECFP-EYFP; mTurquoise2-SeYFP; EGFP-mCherry; and Clover-mRuby. In some embodiments, the acceptor molecule of chimeric fluorescent molecule may quench the light emission of a donor molecule exposed to its preferred wavelength of light. Quenching between different portions of chimeric fluorescent proteins may occur using a photoactivatable acceptor. For example, a chimeric fluorescent protein may include a photoactivatable GFP that can then quench photoemission by CFP. Examples of FRET proteins are discussed in Hildebrandt et al., Sensors (Basel). 2016 September; 16 (9): 1488, incorporated herein by reference.

Fluorescent proteins may also include chimeric combinations of bioluminescent proteins and fluorescent proteins that transfer and receive energy through bioluminescent resonance energy transfer (BRET). In some embodiments, an acceptor in a BRET pair (e.g. GFP) may emit light at a certain wavelength after accepting energy from photons emitted by a bioluminescent protein (e.g. luciferase). In such an embodiment, the bioluminescent protein alone, before arrestin binding of an intracellular receptor domain, would produce light of one particular wavelength. After the arrestin binds the intracellular domain, the bioluminescent protein that would accept the energy emitted by the bioluminescent protein and in turn emit light of different wavelength. For example, luciferase fused to a fluorescent protein and catalyzing luciferin or an analogue would produce a red-shifted light. In this case the luciferase emission alone would be one marker, and the red-shifted emission from the acceptor protein, if it is there, would be the second signal. In another embodiment, a conformational change in the fluorescent acceptor protein (e.g. mNeonGreen) due to a conformational change in the arrestin domain may result in a reduced fluorescence emission capability, leaving the bioluminescent donor signal (e.g. luciferase) unchanged.

As used herein, the term "fluorescent biosensor" (also referred to as a cell signaling sensor protein) refers to a recombinant, fluorescent fusion protein that changes its fluorescence properties in response to a particular type of cell signaling. Genetically encoded, fluorescent biosensors are used to detect changes in intracellular signaling pathways in living cells (see, e.g. U.S. Patent Publication No. 20130298263, U.S. Patent Publication No. 20130344530, U.S. Patent Publication No. 20150037812, and U.S. Patent Publication No. 20170115315, each of which are incorporated by reference). Biosensors may also be used to detect changes in cell membrane voltage (Storace et al. Trends Neurosci. 2016 May; 39 (5): 277-289), as well as changes in intracellular second messengers such as cAMP (Tewson et al. J Biomol Screen. 2016 March; 21 (3): 298-305), DAG (Tewson et al. 2016), and $Ca^{2+}$ (Akerboom et al. Front Mol Neurosci. 2013 Mar. 4; 6:2; Zhao et al. Science. 2011 Sep. 30; 333 (6051): 1888-91).

For example, in the case of excitable cells, a fluorescent biosensor may change fluorescence in response to changes in transmembrane voltage, such as FlaSh (a voltage-gated potassium channel fused to a fluorescent protein), ArcLight (a voltage-sensitive phosphatase fused to a mutated pHluorin), and microbial rhodopsin-based proteins that are either inherently fluorescent or can be paired with a fused fluorescent protein to utilize FRET fluorescence or quenching (e.g. Mermaid, using fluorescent proteins from Coral) (see, e.g. Storace et al. 2016, incorporated herein by reference). Alternatively, the biosensor may change fluorescence in response to changes in the level of a cell signaling molecule such as, for example, $Ca^{2+}$ (e.g. Cameleon, a fusion of calmodulin, calmodulin-binding peptide, and GFP), chloride (e.g. Clomeleon, a fusion of a chloride-sensing yellow fluorescent protein and cyan fluorescent protein), pH (e.g. pHluorin), cAMP (see, e.g. U.S. Patent Application No. 20160274109A1 incorporated herein by reference), cGMP (see, e.g., Nikolaev et al. Nat Methods. 2006 January; 3 (1): 23-5, incorporated herein by reference), or diacylglycerol (DAG) (see, e.g., U.S. Pat. No. 9,547,017 incorporated herein by reference). FLIP biosensors utilize binding proteins from bacteria (e.g. glutamate/aspartate binding protein, glucose binding protein, sucrose binding protein) fused to two GFPs (see, e.g. Okumuto et al. Proc Natl Acad Sci USA. 2005 Jun. 14; 102 (24): 8740-5; Bermejo et al. Biochem J. 2010 Dec. 1; 432 (2): 399-406; Lager et al. J Biol Chem. 2006 Oct. 13; 281 (41): 30875-83). HyPer (a circular permutant of YFP) and roGFP (with substituted cysteines) can be used for detection of reactive oxygen species (see e.g. Bilan et al. 2013). REX-YFP or Peredox (a fusion of fluorescent protein and the T-Rex sensor from *Thermus aquaticus*) may be used to detect the redox state of nicotinamide adenine dinucleotide (NAD+/NADH) (see, e.g. Bilan et al. Biochim Biophys Acta. 2014 March; 1840 (3): 951-7; Hung et al. Cell Metab. 2011 Oct. 5; 14 (4): 545-54). Zinc can be detected using a fusion of a fluorescent protein and a His4 protein sensor (see, e.g. Dittmer et al. J Biol Chem. 2009 Jun. 12; 284 (24): 16289-97). Phosphate detection may be accomplished using bacterial phosphate-binding protein (PiBP) to eCFP and eYFP. Perceval is a fusion of bacterial regulatory protein GlnKI and cpm Venus (e YFP) for detecting the ATP/ADP ratio in live cells (see, e.g., Berg et al., Nat Methods. 2009 February; 6 (2): 161-6). FLIPW is a fusion of tryptophan-activated repressor protein (TrpR) and eCFP and cpm Venus (eYFP) (see e.g. Kaper et al. PLOS Biol. 2007 October; 5 (10):e257). Intracellular lactate may be detected with a fusion of bacterial Lld receptor and Venus (eYFP). MagFRET is a fusion of human centrin 3 (HsCen3) to Cerulean and Citrine that detects magnesium (Lindenburg et al. PLOS One. 2013 Dec. 2; 8 (12):e82009). Exemplary signaling molecules that may be detected by a fluorescent biosensor include, but are not limited to, $Ca^{2+}$, cAMP, cGMP, diacylglycerol, ATP, ADP, glucose, ribose, sucrose, glutamate, hydrogen peroxide, lactate, magnesium, NAD+, NADH, phosphate, reactive oxygen species, and zinc.

As used herein, the term "linker" or "linker sequence" refers to a nucleotide or amino acid sequence that is located between two other nucleotide or amino acid sequences. A nucleic acid linker sequence encodes one or more amino acids. When the term "linker sequence" is used in the context of a peptide or protein, the term refers to one or more amino acid residues.

As used herein, a "circular permutation" refers to a relationship between proteins whereby the proteins have a changed order of amino acids in their peptide sequence. The result is a protein structure with different connectivity, but overall similar three-dimensional (3D) shape.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or MEGALIGN (DNAS-TAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. Mismatches can be similarly defined as differences between the natural binding partners of nucleotides. The number, position and type of mismatches can be calculated and used for identification or ranking purposes.

For the nucleic acid and amino acid sequences provided herein, the disclosure also encompasses nucleic acid and amino acid sequences that are at least 70, 75, 80, 85, 90, 95, 96, 97, 98 or 99% identical to the sequences explicitly provided in the sequence listing filed herewith. In some embodiments, the disclosure also encompasses amino acid sequences described in the sequence listing provided herein as well as those amino acid sequences that differ by 1, 2, 3, 4, 5, 6, 7, 8, 9, 10, 11, 12, 13, 14, 15, 16, 17, 18, 19 or 20 amino acids. The disclosure also encompasses all nucleic acid molecules that encode these amino acid sequences. In some embodiments, the disclosure also encompasses nucleic acid sequences described in the sequence listing provided herein as well as those amino acid sequences that differ by 1, 2, 3, 4, 5, 6, 7, 8, 9, 10, 11, 12, 13, 14, 15, 16, 17, 18, 19 or 20 nucleotides.

The present disclosure also provides not only the nucleic acids and proteins having the specified nucleic and amino acid sequences, but also DNA fragments, particularly fragments of, e.g., 40, 60, 80, 100, 150, 200, or 250 nucleotides, or more, as well as protein fragments of, e.g., 10, 20, 30, 50, 70, 100, or 150 amino acids, or more. Optionally, the nucleic acid fragments can encode fusion proteins as described herein.

There are many amino acids beyond the standard 20 (Ala, Arg, Asn, Asp, Cys, Gln, Glu, Gly, His, Ile, Leu, Lys, Met, Phe, Pro, Ser, Thr, Trp, Tyr, and Val). Some are naturally-occurring others are not. For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH₃, —OH, —CH₂NH₃, —C(O) H, —CH₂CH₃, —CN, —CH₂CH₂CH₃, —SH, or another group. Any amino acid can be substituted by the D-form of the amino acid.

With regard to non-naturally occurring amino acids or naturally and non-naturally occurring amino acid analogs, a number of substitutions in the polypeptide and agonists described herein are possible alone or in combination. For example, glutamine residues can be substituted with gamma-Hydroxy-Glu or gamma-Carboxy-Glu. Tyrosine residues can be substituted with an alpha substituted amino acid such as L-alpha-methylphenylalanine or by analogues such as: 3-Amino-Tyr; Tyr (CH₃); Tyr (PO₃(CH₃)₂); Tyr (SO₃H); beta-Cyclohexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp. Proline residues can be substituted with homopro (L-pipecolic acid); hydroxy-Pro; 3,4-Dehydro-Pro; 4-fluoro-Pro; or alpha-methyl-Pro or an N (alpha)-C (alpha) cyclized amino acid analogues with the structure: n=0, 1, 2, 3 Alanine residues can be substituted with alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of unnatural amino acids include: an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, ¹³C, ¹⁵N, or ¹⁸O); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an .alpha.-hydroxy containing acid; an amino thio acid containing amino acid; an .alpha., .alpha. disubstituted amino acid; a.beta.-amino acid; a cyclic amino acid other than proline; an O-methyl-L-tyrosine; an L-3-(2-naphthyl) alanine; a 3-methylphenylalanine; a.rho.-acetyl-L-phenylalanine; an O-4-allyl-L-tyrosine; a 4-propyl-L-tyrosine; a tri-O-acetyl-GlcNAc.beta.-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl) alanine; D-3-(2-naphthyl) alanine (dNal); an amino-, isopropyl-, or O-allyl-containing phenylalanine analogue; a dopa, O-methyl-L-tyrosine; a glycosylated amino acid; a p-(propargyloxy)phenylalanine; dimethyl-Lysine; hydroxyproline; mercaptopropionic acid; methyl-lysine; 3-nitro-tyrosine; norleucine; pyro-glutamic acid; Z (Carbobenzoxyl); .epsilon.-Acetyl-Lysine; .beta.-alanine; aminobenzoyl derivative; aminobutyric acid (Abu); citrulline; aminohexanoic acid; aminoisobutyric acid (AIB); cyclohexylalanine; d-cyclohexylalanine; hydroxyproline; nitro-arginine; nitro-phenylalanine; nitro-tyrosine; norvaline; octahydroindole carboxylate; ornithine (Orn); penicillamine (PEN); tetrahydroisoquinoline; acetamidomethyl protected amino acids and pegylated amino acids. In some embodiments, an amino acid can be replaced by a naturally-occurring, non-essential amino acid, e.g., taurine.

As used herein, the term "exon" refers to a nucleic acid sequence that encodes a peptide or protein sequence. In some embodiments, an exon encodes part of a protein sequence. In some embodiments, an exon encodes an entire protein sequence.

As used herein, the term "intron" refers to a nucleic acid sequence that interrupts other coding sequences, such as exons.

As used herein, the singular forms "a," "an," and "the" include plural referents unless the context clearly dictates otherwise. For example, a nucleic acid molecule refers to one or more nucleic acid molecules. As such, the terms "a," "an," "one or more," and "at least one" can be used interchangeably. Similarly, the terms "comprising," "including," and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

As used herein, the term "about" in quantitative terms refers to plus or minus 10% of the value it modifies (rounded up to the nearest whole number if the value is not subdividable, such as a number of molecules or nucleotides). For example, "about 100 mg" would encompass 90 mg to 110 mg, inclusive; "about 2500 mg" would encompass 2250 mg to 2750 mg. When applied to a percentage, the term "about" refers to plus or minus 10% relative to that percentage. For example, "about 20%" would encompass 15-20% and "about 80%" would encompass 75-85%, inclusive. Moreover, where "about" is used herein in conjunction with a quantitative term it is understood that in addition to the value plus or minus 10%, the exact value of the quantitative term is also contemplated and described. For example, the term "about 23%" expressly contemplates, describes, and includes exactly 23%.

Vectors for Introducing Nucleic Acids

The present disclosure also discloses nucleic acid vectors useful for practicing methods of the invention. In certain embodiments, a nucleic acid vector of the invention can be a plasmid, a cosmid, a viral vector, and the like, that comprises a nucleic acid molecule of the invention. The nucleic acid constructs described herein may be introduced into a cell using transient transfection techniques (e.g. using a plasmid introduced by lipids or electroporation), or it may be stably integrated into a cellular genome, such as by viral delivery (e.g. using a lentivirus or baculovirus vector). The multifunctional DBS reporter constructs may also be integrated into a specific genomic region of interest, using site-directed recombinase technology (e.g. Cre-Lox or FLP-FRT) or transposon-based technology (e.g. SLEEPING BEAUTY™ transposon/SB100X).

Nucleic acid molecules of the invention may be inserted into the genomes of transgenic animals or model organisms, used to create stable cell lines, or transiently expressed via transfection or viral transduction. In such constructs, the nucleic acid molecule may be inserted into the host genome or remain episomal. Methods to generate stable lines or animals or to transiently express the sensors are well known in the art and readily adaptable for use with the compositions and methods described herein. Nucleic acid sequence of the invention may also be located in the genome of a cell in a transgenic animal and tissue, including, but not limited to, *C. elegans, drosophila*, mice, rats, marmosets, organoids, and embryonic stem cells derived from any vertebrate.

Methods of making cells of the invention are known and the method of transformation and choice of expression vector will depend on the host system selected. Transformation and transfection methods are described, e.g., in Ausubel et al., Current Protocols in Molecular Biology, John Wiley & Sons, New York, N.Y. (1998), and, as described above, expression vectors may be chosen from examples known in the art. A number of compositions and methods can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Examples of viral vectors useful for practicing the present invention include, but are not limited to, Adenovirus, Adeno-associated virus, Lentivirus, Baculovirus modified for mammalian expression (BacMam), herpes virus, Vaccinia virus, Polio virus, Sindbis, and other RNA viruses, including these viruses with the HIV backbone. Non-viral based vectors, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs.

As described above, sensor systems of the invention are useful for measuring arrestin alone or in combination with changes in other cell signaling molecules (e.g., $Ca^{2+}$, CAMP, cGMP, diacylglycerol, ATP, ADP, glucose, glutamate, hydrogen peroxide, lactate, magnesium, NAD+, NADH, phosphate, reactive oxygen species, ribose, sucrose, zinc, etc.) in GPCR-expressing cells that are exposed to an agonist. Cell signaling biosensors, including fluorescent biosensors having a different emission spectrum than the arrestin biosensor, may be used. Exemplary cell signaling biosensor may include, but are not limited to, a red fluorescent cAMP sensor (e.g. cADDIS, Montana Molecular, Bozeman, MT, USA), a red DAG sensor (Montana Molecular, Bozeman, MT, USA; see e.g. U.S. Pat. No. 9,547,017, incorporated by reference herein). Thus, one embodiment of the technology is a method of measuring arrestin signaling in a cell, comprising contacting a cell comprising a nucleic acid molecule of the technology to a G-protein-coupled receptor agonist and exposing the cell to light having the excitation wavelength of the first fluorescent protein and the second fluorescent protein, and measuring the fluorescence from the cell at the emission wavelength of the first fluorescent protein and the second fluorescent protein.

As described herein, the term "fluorescence" is the property of some atoms and molecules to absorb light at a particular wavelength, called the excitation wavelength and to subsequently emit, after a brief interval, light of a longer wavelength, called the emission wavelength. Excitation of a susceptible molecule by an incoming photon happens in femtoseconds, while vibrational relaxation of excited state electrons to the lowest energy level is much slower and can be measured in picoseconds. The final process, emission of a longer wavelength photon and return of the molecule to the ground state, occurs in the relatively long time period of nanoseconds. Because of the tremendously sensitive emission profiles, spatial resolution, and high specificity of fluorescence, various fluorescent sensors with differing emission wavelengths can be expressed in the same cell, and responses to various types of ligands can be simultaneously measured. For instance, a cell can express a biosensor for arrestin linked to mNeonGreen (a green fluorescent reporter protein), and a biosensor for cAMP or a biosensor for $Ca^{2+}$ can be linked to a red fluorescent reporter protein. By utilizing different excitation and emission wavelengths, the responses can be separately monitored and recorded. As described herein, the term "rate" is a measurement of the speed at which something happens or wherein changes within a particular period occur. Changes in fluorescence can be measured over time, and from such measurements, the rate, i.e. the speed at which the change in fluorescence occurs, can be determined. For instance, in the cell system expressing the recombinant arrestin biosensor construct, a change in fluorescence can be recorded in response to binding of select ligands. Depending on the ligand, the change in fluorescence can be rapid (i.e. a large change in fluorescence over a short time interval) or slower (a lesser change in fluorescence, measured over the same time interval). The time intervals between measurements selected can be 0.01, 0.1, 0.5, 1.0, 3.0, 3.0, 4.0, 5.0, or more seconds. The entire time interval for measurement can be at least 90 seconds. The entire time interval can also be at least 15 minutes. The number of measurements conducted during the time interval can be 3, 4, 5, 6, 7, 8, 9, 10, 20, 30, 40, 50, 60, 70, 80, 90, 100, 200, 300, 400, 500, 600, 700, 800, 900, or 1000 or more measurements. The rate is determined by dividing the change in fluorescence intensity (i.e. Δ fluorescence) divided by time span (i.e. length of time, or Δt) during which the measurement was made.

As described herein, the rate of a change in fluorescence reflects the responsiveness of the arrestin biosensor to exogenously added ligands for the G-protein coupled receptor. To differentiate between the effect of different ligands on the G-protein coupled signaling involving arrestin, the rate in the change in fluorescence caused by one particular ligand can be compared to the rate in the change in fluorescence caused by another ligand. For instance, the change in the rate of fluorescence intensity caused by the angiotensin substrate can be compared to the change in the rate of fluorescence intensity caused by SIIB substrate. The rate in the change in fluorescence can be determined for any selected time interval. For instance, the rate can be determined immediately after addition of the ligand to the cell system, to reflect an initial rate.

As described herein, the maximum and minimum value of fluorescence reflects those values that are not further increased, or not further decreased, respectively, after a G-protein ligand has been added to the cell system. In some embodiments, those maximum and minimum fluorescence values correlate with the responsiveness of the biosensor for the G protein coupled ligand (for instance, arrestin with an arrestin sensor, cAMP with a cAMP sensor, $Ca^{2+}$ with a $Ca^{2+}$ sensor, or DAG with a DAG sensor).

As described herein, "biased agonism" refers to is the ligand-dependent selectivity for certain signal transduction pathways relative to a reference ligand (often the endogenous hormone or peptide) at the same receptor. Other terms that refer to biased agonism include "functional selectivity," "agonist trafficking," "biased signaling," "ligand bias," and "differential engagement".

As described herein, a "standard" is a control value. For instance, if a compound was being tested for arrestin or G-protein agonism, a standard for arrestin and G-protein agonism (their respective standards) could be the same or different molecules. In both instances the standard would be one that had a known effect on arrestin or G-protein agonism. In some embodiments, that effect would be a low or negligible effect.

In some embodiments, wherein fluorescence in one cell or group of cells is being compared to fluorescence in another cell or group of cells, the measurement and/or detection of fluorescence is done within a relatively short time frame. In some embodiments, this short time frame is less than 60, 50, 40, 30, 20, 10, 9, 8, 7, 6, 5, 4, 3, 2, 1, 0.1, 0.05, 0.01, 0.005 or 0.001 seconds. In some embodiments, the measurement and/or detection of fluorescence is done simultaneously or at substantially the same time.

One embodiment of the present invention is a kit for practicing methods of the present invention. Kits can include a nucleic acid molecule, a nucleic acid vector, or a cell of the present technology as well components for making such nucleic acid molecules, nucleic acid vectors, or cells. As such, kits can include, for example, primers, nucleic acid molecules, expression vectors, DNA constructs of the present invention, cells, buffers, reagents, and directions for using any of said components. It should be appreciated that a kit may comprise more than one container comprising any of the aforementioned, or related, components. For example, certain parts of the kit may require refrigeration, whereas other parts can be stored at room temperature. Thus, as used herein, a kit comprises components sold in separate containers by one or more entity, with the intention that the components contained therein be used together.

Arrestin Signaling Biosensor

A ribbon diagram of an exemplary arrestin signaling biosensor protein is shown in FIG. 1A. This design uses the fluorescent protein mNeonGreen that was circularly permuted by fusing the original N- and C-termini of mNeonGreen together with a short peptide linker. The cpmNeonGreen amino acid sequence is connected to a linker sequence. The linker sequence is connected to an arrestin protein, such as beta-arrestin-2. FIG. 1B shows a schematic diagram of the fusion protein in FIG. 1A from N-terminus to C-terminus.

Figures 2A, 2B:
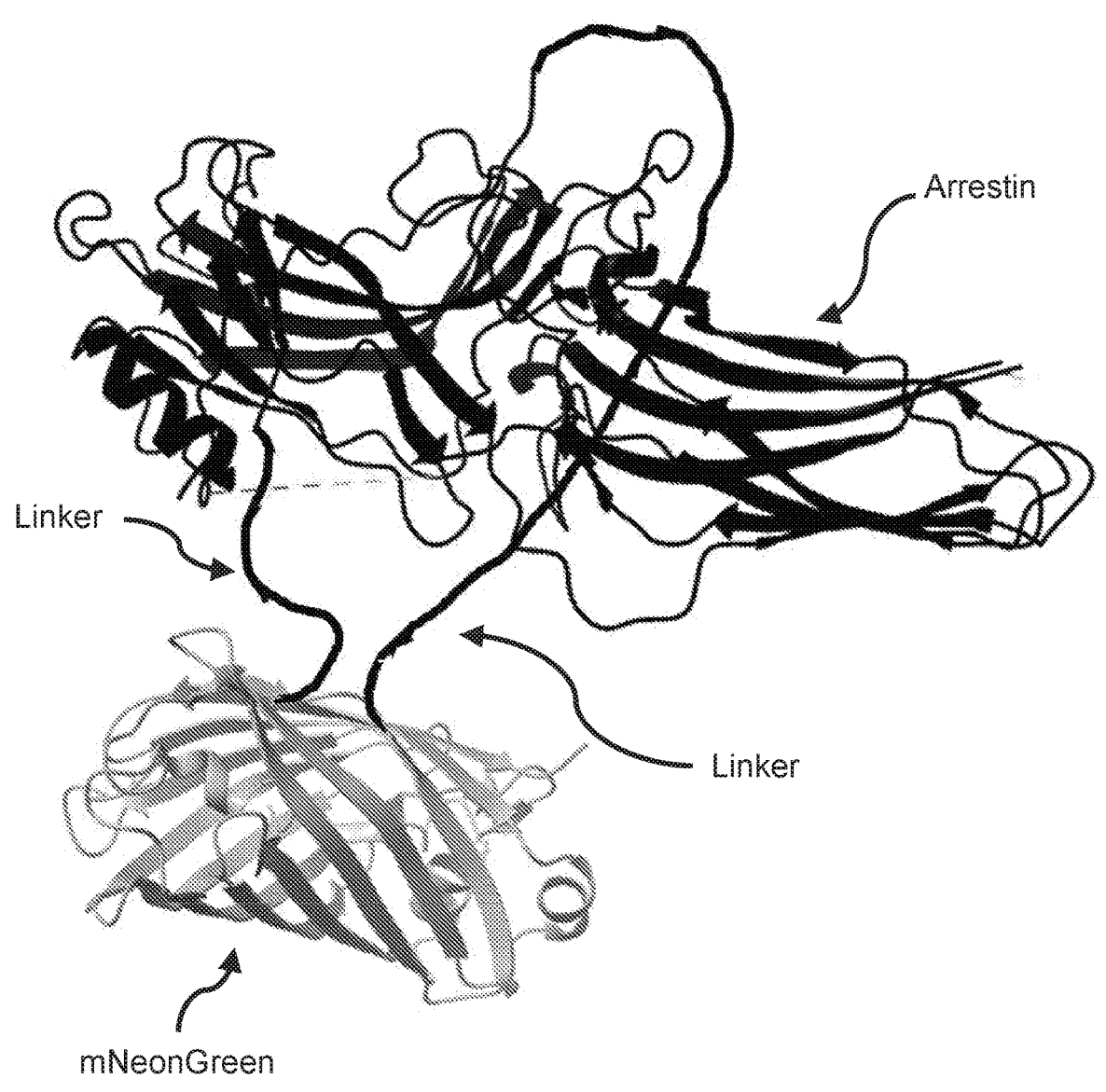
FIG. 2A is a ribbon diagram of a second embodiment of an arrestin biosensor.
FIG. 2B is a block diagram of the arrestin biosensor of FIG. 1B, with the N-terminus on the left and C-terminus on the right.

FIG. 2A shows a schematic diagram of a second example of an arrestin signaling biosensor. In this design, the N- and C-termini of an arrestin, such as beta-arrestin-2 are fused to portions of the seventh stave of the beta sheet in unpermuted m NeonGreen. This design essentially inserts the arrestin into the side of the mNeonGreen barrel. Linker sequences join the N- and C-termini of arrestin to each of the portions of the unpermuted mNeonGreen.

FIG. 2B shows a schematic diagram of the fusion protein in FIG. 2A from N-terminus to C-terminus. A first portion of mNeonGreen is connected at its C-terminus to a first amino acid linker sequence. The C-terminus of the first amino acid linker sequence is connected to the N-terminus of an arrestin protein sequence, such as beta-arrestin-2. The C-terminus of the arrestin protein sequence is connected to a second amino acid linker sequence. The C-terminus of the second amino acid linker sequence is connected to the N-terminus of a second portion of mNeonGreen.

With either design, there is no physical model that makes predictions about what the best fusions would be. This means that creating a robust biosensor is a matter of trial and error. The process used to find the arrestin sensors described herein involved first creating a number of sensors individually to test the different designs. Each of the plasmids encoding a prototype was transiently expressed, through transient transfection, in HEK293T cells that also expressed a G-protein coupled receptor. If activation of the receptor produced a change in fluorescence, the prototype was considered a starting point. Mutagenic PCR primers were then used to randomly mutagenize two to three amino acids at a time at the fusion junction/s. This produced random libraries of thousands of mutants. Clones were grown in 96 well format, and the resulting cDNA was transiently expressed and co-expressed with G-protein coupled receptors either with, or without, additional G-protein receptor kinase. Initially, the screening for fluorescence change was done well-by-well on a fluorescence microscope with time lapse imaging. As prototypes are discovered that are bright enough, and produce a large signal, the screening moves to an automated fluorescence plate reader with a higher throughput. Thousands of clones are screened, and prototypes are gradually mutagenized and optimized for signal size through an iterative process of mutagenize, test, and sequence.

The table in FIG. 3A lists nucleic acid and protein sequences for construct BArr 1A, which encodes a cpm-NeonGreen, a glycine residue, and beta-arrestin-2. The expressed fusion protein shows a decrease in fluorescence following agonist activation of receptors in transfected cells. This circularly permuted arrestin sensor fluoresces green when the arrestin portion of the fusion protein is unbound, and its fluorescence is quenched when the arrestin portion of the biosensor binds an activated GPCR.

The table in FIG. 3B lists nucleic acid and protein sequences for constructs BArr 3D and 3F, which encodes a fusion molecule of beta-arrestin-2, a three-residue linker sequence, and cpmNeonGreen. As with BArr 1A, these biosensors fluoresce green when the arrestin portion of the fusion protein is unbound, and its fluorescence is quenched when the arrestin portion of the biosensor binds an activated GPCR About 1500 different permutations of linkers were tested for the design shown in FIG. 2, and only a small number produced any fluorescent response. The tables in FIGS. 3C and 3D list the nucleic acid constructs and corresponding fusion protein sequences that changed fluorescence following agonist activation of receptors in cells. Similar to the circularly permuted arrestin sensor described above in FIGS. 1A-1B, the unpermuted arrestin sensor depicted in FIGS. 2A-2B fluoresces green when the arrestin portion of the fusion protein is unbound to a GPCR, and its fluorescence is quenched when the arrestin portion of the biosensor binds an activated GCPR. However, the unpermuted arrestin biosensors have a greater fluorescent intensity (i.e. brightness or light amplitude) than the permuted arrestin biosensor described above.

EXAMPLES

The following examples are meant to be illustrative and should not be construed as further limiting. The contents of the figures and all references, patents, and published patent applications cited throughout this application are expressly incorporated herein by reference.

Example 1: Arrestin Sensor Fluorescence with GPCR Activation

In order to analyze the fluorescent response of the arrestin sensor BArr 5A, HEK293T cells were transiently transfected with plasmids encoding a particular G-protein coupled receptor, as well as the green fluorescent arrestin sensor BArr 5A (SEQ ID NO: 31). Cells were transfected with either the angiotensin II receptor, the beta-2 adrenergic receptor, or the Dopamine 1 receptor. The fluorescence of the cells was monitored on a microscope using time-lapse imaging. Drugs were added to the transfected cells by hand after collecting 3 to 4 images, and the resulting fluorescence was measured. Cells transfected with the Angiotensin II receptor were treated with angiotensin II or with the agonist SIIB. Cells transfected with the beta-2 Adrenergic receptor were treated with isoproterenol or with isoetherine, and cells transfected with Dopamine Receptor 1 were treated with dopamine.

Figure 4:
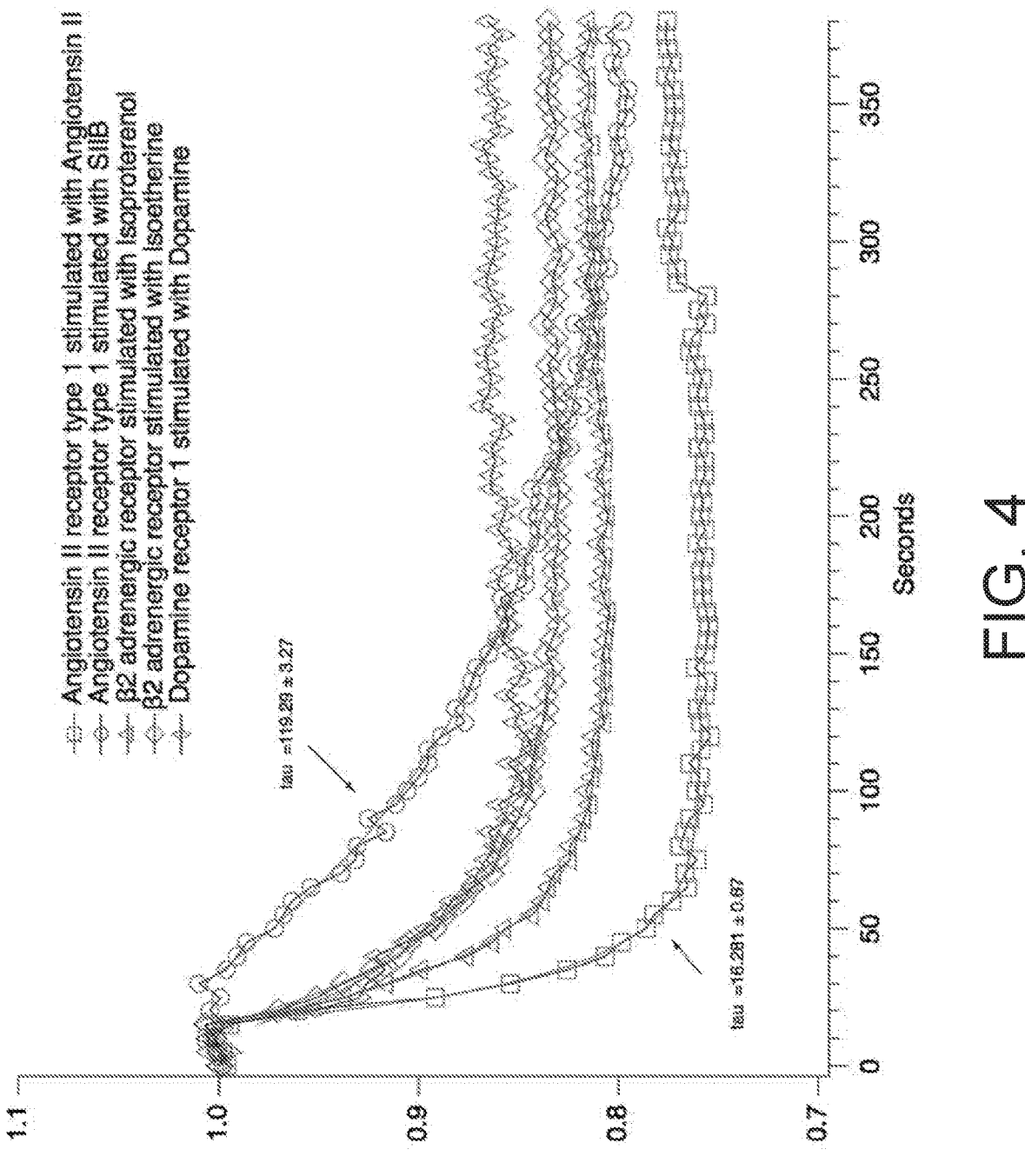
FIG. 4 is a graph showing changes in the normalized fluorescence over time for HEK293T cells co-transfected with the green fluorescent BArr 5A biosensor and a G-protein coupled receptor (angiotensin II receptor, beta2 adrenergic receptor, or DI receptor for dopamine), following stimulation with different agonists.

FIG. 4 shows a graph of the normalized fluorescence for each of the drug-treated, transfected cells. The kinetics of the BArr 5A biosensor's response is different for different receptors or for different ligands acting at the same receptor. In particular, the addition of Angiotensin II produced a very fast response (tau=16 s) following the activation of the Angiotensin II receptor type 1. The biased agonist SII, however, acting at the same receptor produced a much slower response (tau=119 s). This illustrates one way in which the sensor can be used to identify biased agonists.

Example 2: Simultaneous Detection of Gq Signaling (DAG) and Arrestin Signaling Biased agonists acting at a GPCR can activate two very different sets of second messengers. In one case the receptor can activate the canonical G-protein pathway, while in the other it can activate arrestin signaling.

It is important to note that translocation assays can be difficult to interpret, because the activation of a GPCR always recruits arrestin to the cell surface as a part of receptor inactivation and turn over. In fact, arrestin translocation has been used as an unbiased way to "de orphanize" receptors (Oakley et al. 2006; Oakley and Hudson 2008).

In this experiment, HEK293T cells were transiently transfected with plasmids encoding the Angiotensin II receptor type 1 (AT1), the green fluorescent arrestin sensor BArr L1-3 B8 (SEQ ID NO: 56), and red fluorescent sensor for diacylglycerol (DAG).

Figures 5A, 5B:
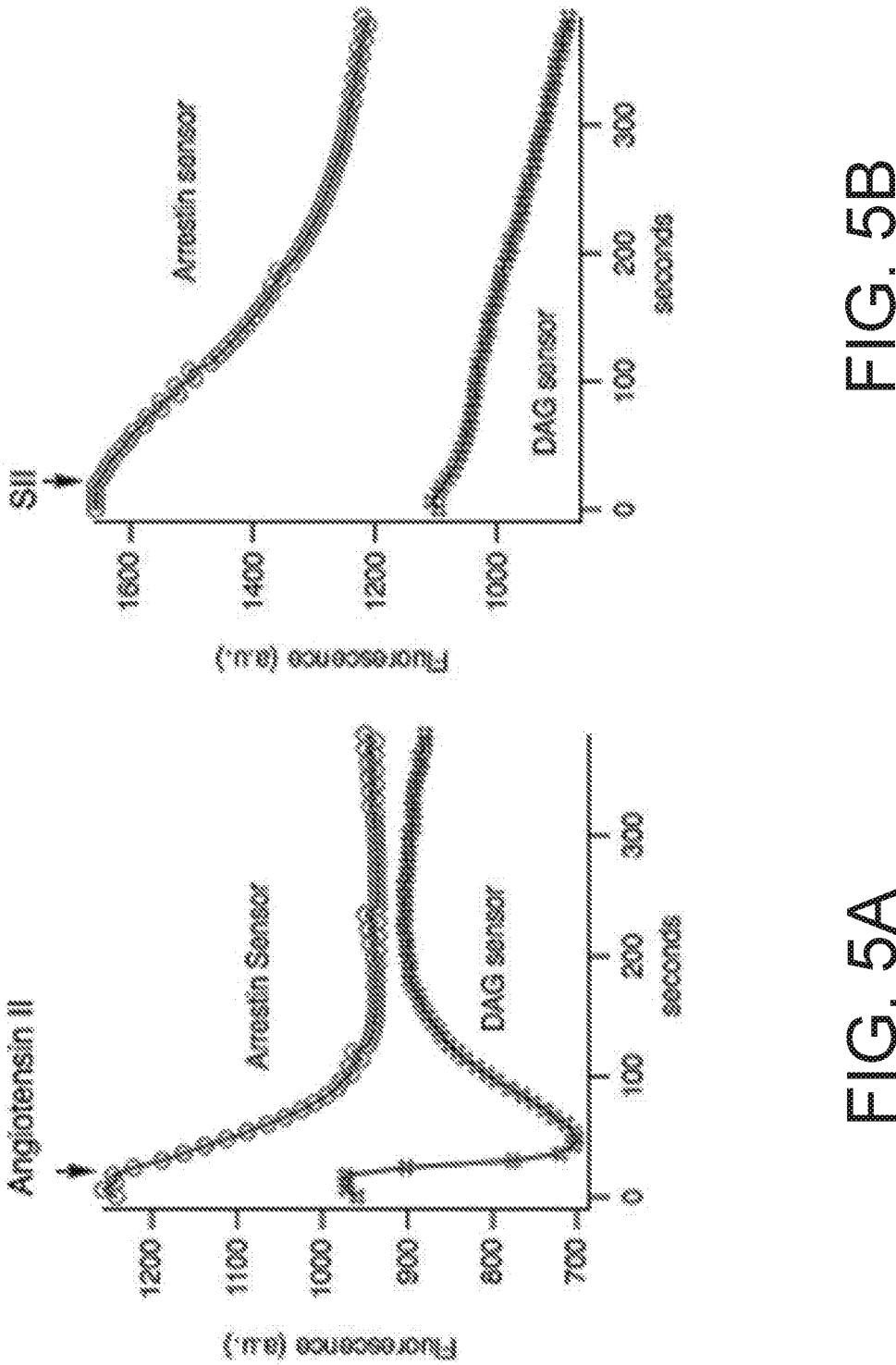
FIG. 5A is a graph showing changes in fluorescence over time for HEK293T cells co-transfected with the angiotensin II receptor, the green fluorescent BArr L1-3 B8 biosensor, and a red biosensor for diacylglycerol (DAG), following stimulation with the agonist angiotensin II.
FIG. 5B is a graph showing changes in fluorescence over time for HEK293T cells co-transfected with the angiotensin II receptor, the green fluorescent BArr L1-3 B8 biosensor, and a red biosensor for diacylglycerol (DAG), following stimulation with the arrestin-biased agonist SII.

FIGS. 5A and SB show changes in green (arrestin biosensor) and red (DAG biosensor) fluorescence over time for AT1-expressing cells treated with either Angiotensin II or with SII. In FIG. 5A, Angiotensin II triggers both a rapid response in the arrestin sensor as well as a rapid increase in DAG, indicated by the loss of red fluorescence. This shows that the receptor activated the Gq G-protein, which in turn activates phospholipase C and produces DAG. Simultaneously, angiotensin II activates the arrestin sensor, with a significant decrease in green fluorescence. This is in contrast with treatment by SII. As seen in FIG. 5B, the biased agonist SII produced a very slow response in the arrestin sensor and no detectable response in the DAG sensor, other than the photo-bleaching caused by the imaging. This result is consistent with SII signaling predominantly through the arrestin pathway.

Example 3: Simultaneous Detection of Gs Signaling and Arrestin Signaling on 96-Well Plates To determine whether the arrestin sensor signal is sufficient for use on automated, fluorescence plate readers, HEK293T cells were plated in a 96 well dish, and transfected with a mixture of plasmids designed to express the beta-2 adrenergic receptor (ADBR2), a red fluorescent cAMP sensor (cADDis, Montana Molecular, Bozeman, MT, USA), and the green fluorescent arrestin sensor (BArr L1-3B8; SEQ ID NO: 56). The plate was scanned for several minutes to establish the baseline, and then different drugs were added to different wells, and the red and green fluorescent signals were collected for each well over time.

Figures 6A, 6B:
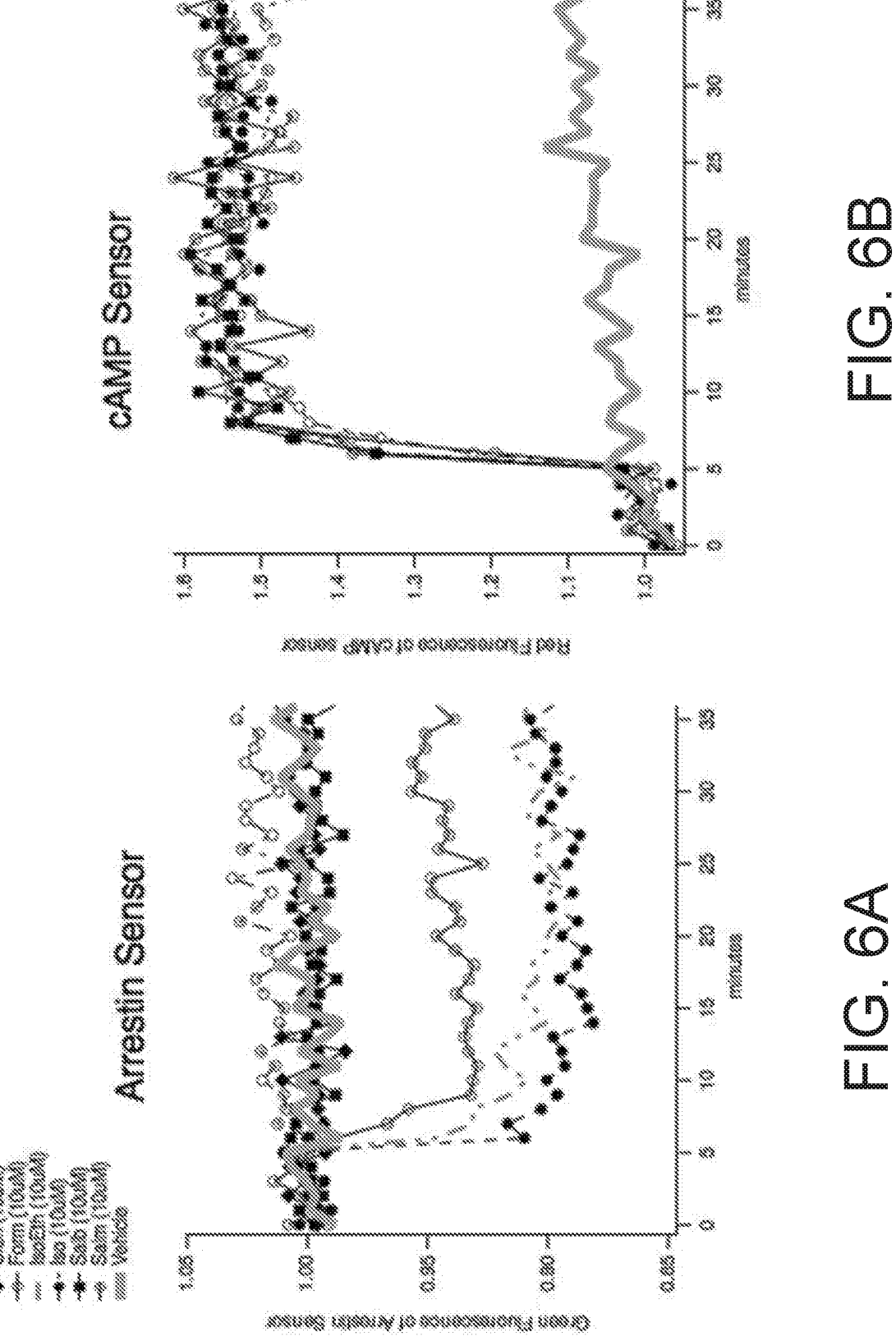
FIG. 6A is a graph showing changes in fluorescence over time for HEK293T cells co-transfected with the beta2 adrenergic receptor, the green fluorescent BArr L1-3 B8 biosensor, and a red biosensor for cyclic adenosine monophosphate (cAMP), following stimulation with various agonists. The graph shows only the green fluorescence changes for the BArr L1-3 B8 biosensor.
FIG. 6B is a graph showing changes in fluorescence over time for HEK293T cells co-transfected with the beta2 adrenergic receptor, the green fluorescent BArr L1-3 B8 biosensor, and a red biosensor for cyclic adenosine monophosphate (cAMP), following stimulation with various agonists. The graph shows only the red fluorescence changes for the CAMP biosensor.

FIGS. 6A and 6B show changes in green (arrestin biosensor) and red (cAMP biosensor) fluorescence over time for ADBR2-expressing cells treated with clenbuterol (10 µM), formoterol (10 µM), isoetharine (10 µM), isoproterenol (10 µM), salbutomol (10 µM), and salmeterol (10 µM). FIG. 6A shows changes in the green fluorescence of the arrestin sensor following drug treatment, while FIG. 6B shows changes in the red fluorescence of the CAMP sensor following drug treatment.

The vehicle alone produced no change in either the green or red fluorescence (gray solid line). Isoproterenol at 10 µM concentration produced a robust change in fluorescence in both the arrestin sensor and cAMP sensor channels. Isoetharine at 10 µM also produced similar responses, while formoterol produced a smaller signal in the arrestin sensor. These three agonists (isoproterenol, isoetharine, and formoterol) stimulate both the Gs and arrestin pathways. The biased agonists salbutamol and salmeterol produced no change in the fluorescence of the arrestin sensor and a large change in the fluorescence of the CAMP sensor, indicating that these do not stimulate the arrestin signaling, but do stimulate the Gs pathway.

Figure 7B:
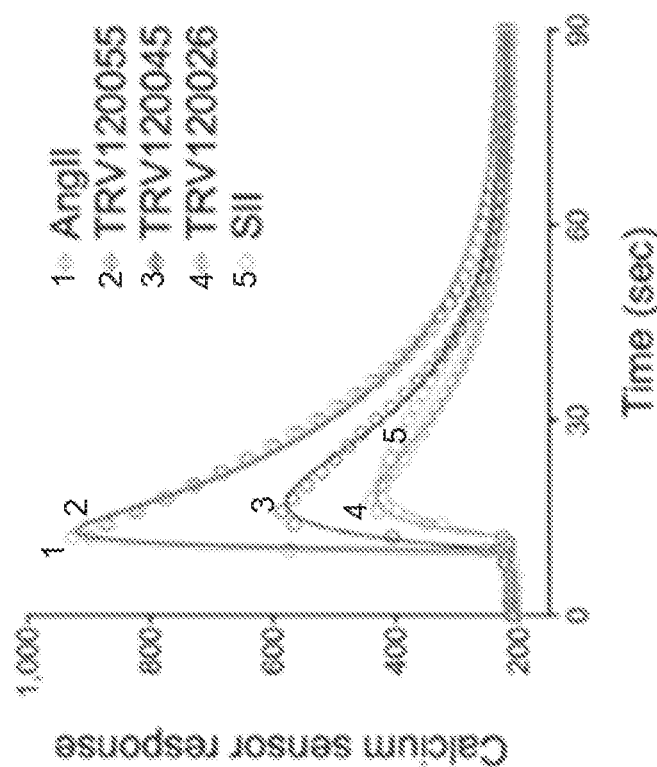
FIG. 7B is a graph showing changes in fluorescence over time for HEK293T cells co-transfected with the angiotensin II receptor, the green fluorescent BArr L1-3 B8 biosensor, and a red biosensor for $Ca^{2+}$, following stimulation with a series of peptides with known degrees of bias against the angiotensin receptor. The graph shows the red fluorescence changes for the $Ca^{2+}$ sensor.
Figure 7A:
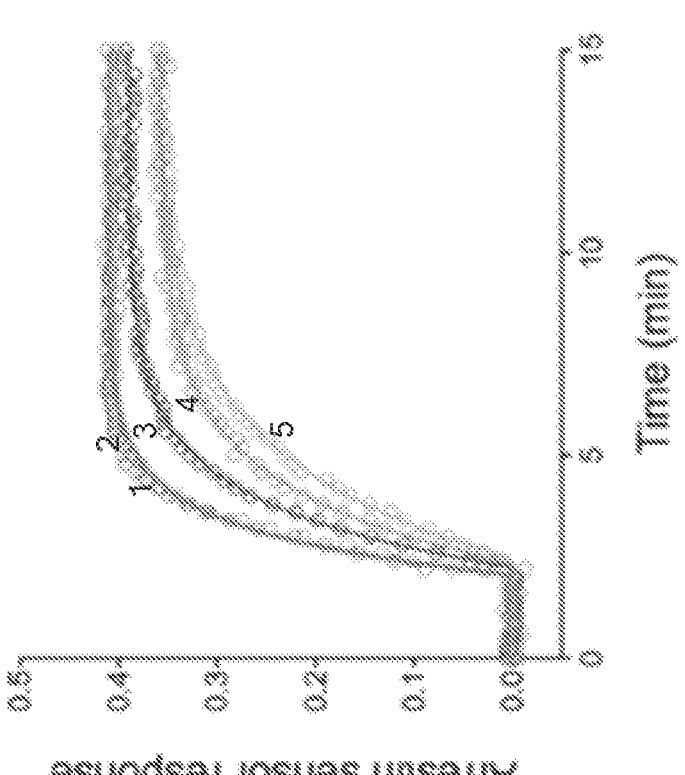
FIG. 7A is a graph showing changes in fluorescence over time for HEK293T cells co-transfected with the angiotensin II receptor, the green fluorescent BArr L1-3 B8 biosensor, and a red biosensor for $Ca^{2+}$, following stimulation with a series of peptides with known degrees of bias against the angiotensin receptor. The graph shows the green fluorescence changes for the Barr L1-3 B8 sensor.

FIG. 7A shows changes in fluorescence over time for HEK293T cells co-transfected with the angiotensin II receptor, the green fluorescent BArr L1-3 B8 biosensor, and a red biosensor for $Ca^{2+}$, following stimulation with angiotensin II and SII, and a series of peptides with known degrees of bias against the angiotensin receptor. The peptides tested are three trevena (TRV) peptides. The arrestin sensor response is measured over a 15 minute time span. The different ligands produce different responses over time, where Angiotensin II and TRV120055 produce the fastest response, and the SII substrate the slowest response.

FIG. 7B shows the changes in fluorescence for the $Ca^{2+}$ biosensor over time in response to angiotensin II and SII, and a series of peptides, measured over a 90 second time interval. The substrates differ in the peak fluorescence responses generated as well as the kinetics of a change in fluorescence intensity over time.

Figure 8:
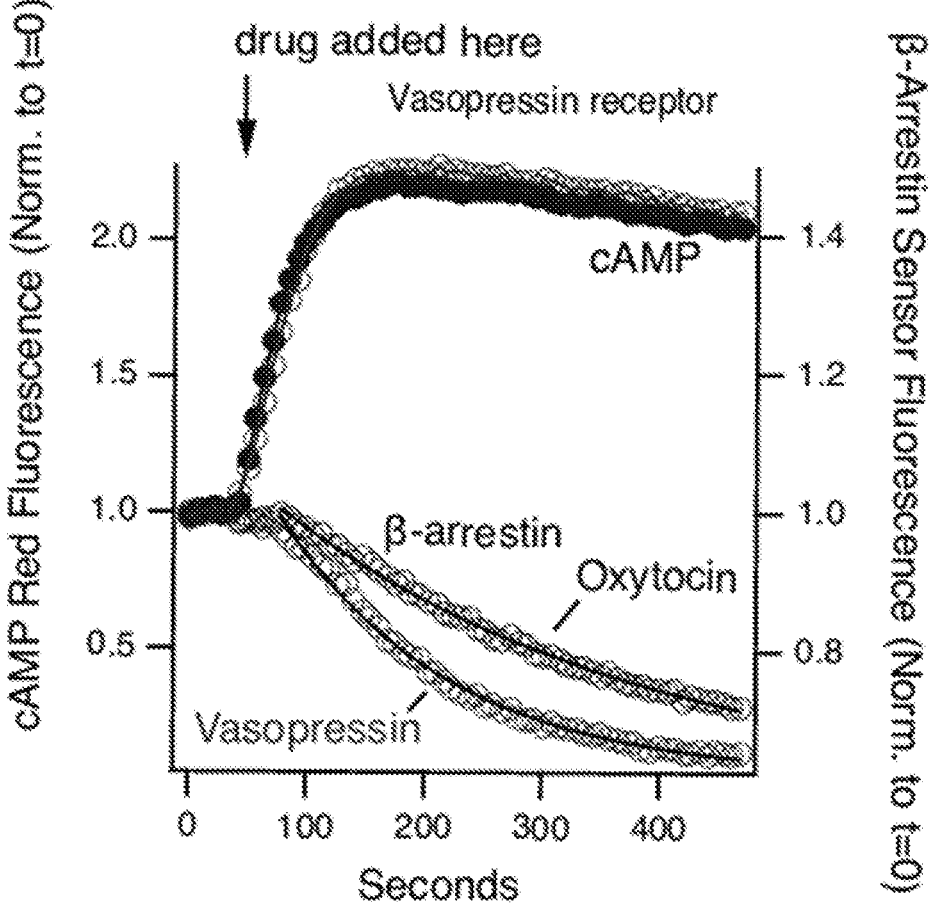
FIG. 8 is a graph showing changes in fluorescence over time for HEK293T cells co-transfected with angiotensin II receptor, the green fluorescent BArr L1-3 B8 biosensor, and a red biosensor for cyclic adenosine monophosphate (cAMP), following stimulation with various vasopressin ligands. The cAMP response is expressed on the first Y-axis, the beta-arrestin response on the second Y-axis.

FIG. 8 is a graph showing changes in fluorescence over time for HEK293T cells co-transfected with angiotensin II receptor, the green fluorescent BArr L1-3 B8 biosensor, and a red biosensor for cyclic adenosine monophosphate (cAMP), following stimulation with two vasopressin ago-
nists, vasopressin and oxytocin. The cAMP red fluorescence
response is shown on the left Y-axis, and the green beta-
arrestin response is shown on the right Y-axis. Vasopressin
and oxytocin are biased agonists at the vasopressin receptor.
Both agonists cause the same cAMP response while the beta arrestin signaling is significantly slower in the case of
oxytocin as compared to vasopressin.

The foregoing description is intended to illustrate but not
to limit the scope of the disclosure, which is defined by the
scope of the appended claims. Other embodiments are
within the scope of the following claims.

What is claimed is:

1. A nucleic acid encoding a fusion protein, wherein the fusion protein consists of an arrestin protein, a linker, and a single circularly permuted fluorescent protein;

wherein the fusion protein undergoes a change in fluorescence upon association with an intracellular portion of a G-protein-coupled receptor, wherein the circularly permuted fluorescent protein is at least 95% identical to SEQ ID NO: 5, and wherein the linker consists of an amino acid sequence selected from the group consisting of Gly, Pro-Ser-His, Met-Arg-Gly, SEQ ID NO: 46, SEQ ID NO: 57, and Asn-Val.

2. A vector comprising the nucleic acid encoding the fusion protein of claim 1.

3. A cell comprising the vector of claim 2.

4. A cell comprising the nucleic acid encoding the fusion protein of claim 1.

5. A kit comprising the nucleic acid encoding the fusion protein of claim 1.

6. A method for measuring arrestin signaling in a cell, the method comprising:

exposing a cell comprising the nucleic acid encoding the fusion protein of claim 1 to light having an excitation wavelength of the fusion protein, and measuring change in the fluorescence over time from the cell at the emission wavelength of the fluorescent protein.

7. A method for comparing the effects of molecules on a G-protein coupled receptor, the method comprising:

a) contacting a cell comprising the nucleic acid encoding the fusion protein of claim 1 with a molecule that binds a G-protein coupled receptor;

b) exposing said cell to light having an excitation wavelength of the fusion protein; and c) measuring change in the fluorescence over time from the cell at the emission wavelength of the fusion protein.

8. A method of determining a more optimum time for measuring arrestin signaling in a cell, the method comprising:

a) exposing a cell comprising the nucleic acid encoding the fusion protein of claim 1 to light having an excitation wavelength of the fusion protein; and b) measuring change in the fluorescence from the cell over time at the emission wavelength of the fusion protein at two or more time points, wherein the time point that shows the greater difference between a control result and a result generated by contacting the cell with a molecule that binds a G-protein coupled receptor is the more optimum time for measuring arrestin signaling in the cell.

9. A method for measuring bias of arrestin and G-protein signaling in a cell, the method comprising:

a) exposing a cell comprising the nucleic acid encoding the fusion protein of claim 1 and a cell comprising a biosensor that detects G-protein signaling that fluoresces at a wavelength distinct from the fusion protein, to light having an excitation wavelength of the fusion protein, b) measuring change in the fluorescence over time from the cell comprising the nucleic acid encoding the fusion protein of claim 1 at the emission wavelength of the fusion protein, c) measuring change in the fluorescence over time from the cell comprising a biosensor that detects G-protein signaling at the wavelength that is distinct from the wavelength at which the fusion protein fluoresces, d) comparing each measured fluorescence to a respective standard, and e) comparing the change in fluorescence of the fluorescence of the emission wavelength of the fusion protein in relation to its respective standard to the change in the fluorescence of the emission wavelength of the biosensor that detects G-protein signaling.

10. A fusion protein consisting of an arrestin protein, a linker, and a single circularly permuted fluorescent protein, wherein the fusion protein undergoes a change in fluorescence upon association with an intracellular portion of a G-protein-coupled receptor, wherein the circularly permuted fluorescent protein is at least 95% identical to SEQ ID NO: 5, and wherein the linker consists of an amino acid sequence selected from the group consisting of Gly, Pro-Ser-His, Met-Arg-Gly, SEQ ID NO: 46, SEQ ID NO: 57, and Asn-Val.

\* \* \* \* \*